United States Patent [19]
Chong et al.

[11] Patent Number: 6,018,019
[45] Date of Patent: Jan. 25, 2000

[54] SYNTHETIC HAEMOPHILUS INFLUENZAE CONJUGATE VACCINE

[75] Inventors: Pele Chong, Richmond Hill; Ali Kandil, Willowdale; Charles Sia, Thornhill; Michel Klein, Willowdale, all of Canada

[73] Assignee: Connaught Laboratories Limited, Willowdale, Canada

[21] Appl. No.: 08/256,839

[22] PCT Filed: Feb. 3, 1993

[86] PCT No.: PCT/CA93/00041

§ 371 Date: Oct. 3, 1994

§ 102(e) Date: Oct. 3, 1994

[87] PCT Pub. No.: WO93/15205

PCT Pub. Date: Aug. 5, 1993

[30] Foreign Application Priority Data

Feb. 3, 1992 [GB] United Kingdom .................. 9202219

[51] Int. Cl.[7] .................................................. A61K 38/12
[52] U.S. Cl. ......................... 530/324; 530/325; 530/326; 530/327; 435/851; 424/185.1; 424/190.1; 424/256.1
[58] Field of Search ........................ 435/851; 424/185.1, 424/190.1, 256.1; 530/326, 327, 325, 324

[56] References Cited

FOREIGN PATENT DOCUMENTS

| 0281673 | 9/1988 | European Pat. Off. ......... C12N 15/00 |
| 0320289 | 6/1989 | European Pat. Off. ......... C12N 15/00 |
| 0389925 | 10/1990 | European Pat. Off. .......... C07K 3/12 |
| 88/04932 | 7/1988 | WIPO ............................. A61K 35/66 |
| 90/02557 | 3/1990 | WIPO ............................. A61K 35/66 |
| 95/03069 | 2/1995 | WIPO ............................. A61K 39/102 |

OTHER PUBLICATIONS

Munson et al, "Molecular Cloning, Expression, and Primary Sequence of Outer Membrane Protein P2 of *Haemophilus influenzae* Type b", *Infection and Immunity*, vol. 57, No. 1(Jan. 1989), pp. 88–94.

Hansen et al, "Structural and Antigenic Conservation of the P2 Porin Protein Among Strains of *Haemophilus influenzae* Type b", *Infection and Immunity*, vol. 57, No. 11(Nov. 1989), pp. 3270–3275.

Martin et al, "Mapping of B–Cell Epitopes on the Outer Membrane P2 Porin Protein of *Haemophilus influenzae* by Using Recombinant Proteins and Synthetic Peptides", *Infection and Immunity*, vol. 59, No. 4 (Apr. 1991), pp. 1457–1464.

Hamel et al, "Localization of Conserved B–Cell Epitopes Among Encapsulated and Non–Encapsulated *Haemophilus influenzae* P2 Porin Proteins Using Synthetic Peptides", *Journal Of General Microbiology*, vol. 138, Part 1(Jan. 1992), pp. 161–168.

Jemmerson "Effects of Conformation, Amino Acid Sequence, and Carrier Coupling on the Immunological Recognition of Peptide and Protein Antigens" in: Zegers et al., *Immunological Recognition of Peptides in Medicine and Biology* (New York, CRC, 1995), pp. 213–225.

*Primary Examiner*—Jeffrey Stucker
*Attorney, Agent, or Firm*—Sim & McBurney

[57] ABSTRACT

The present invention provides immunogenic synthetic peptides which are useful alone or in PRP-conjugates in vaccines against *Hemophilus influenza* infection. Modifications are possible within the scope of the invention.

5 Claims, 28 Drawing Sheets

SYNTHETIC PEPTIDES USED IN SYNTHETIC PRP TRIMER CONJUGATION

HIBP1-4   YAKAQVERNAGLIADSVKDNQITSALSTQC

CHIBP1-4  CYAKAQVERNAGLIADSVKDNQITSALSTQ

COMP2-8   CDIVAKIAYGRTNYKYNESDEHKQQLNG

MAP(COMP2-8)

CP6-6     CVKGYLAGYLAGKGVDAGKLGTVSYG

P24EC     GPKEPFRDYVDRFYKC

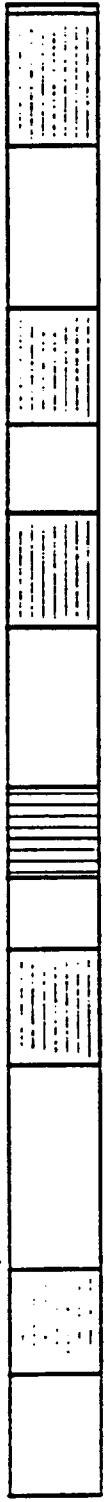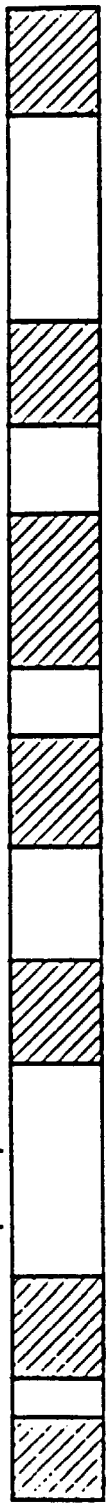
FIG. 5.

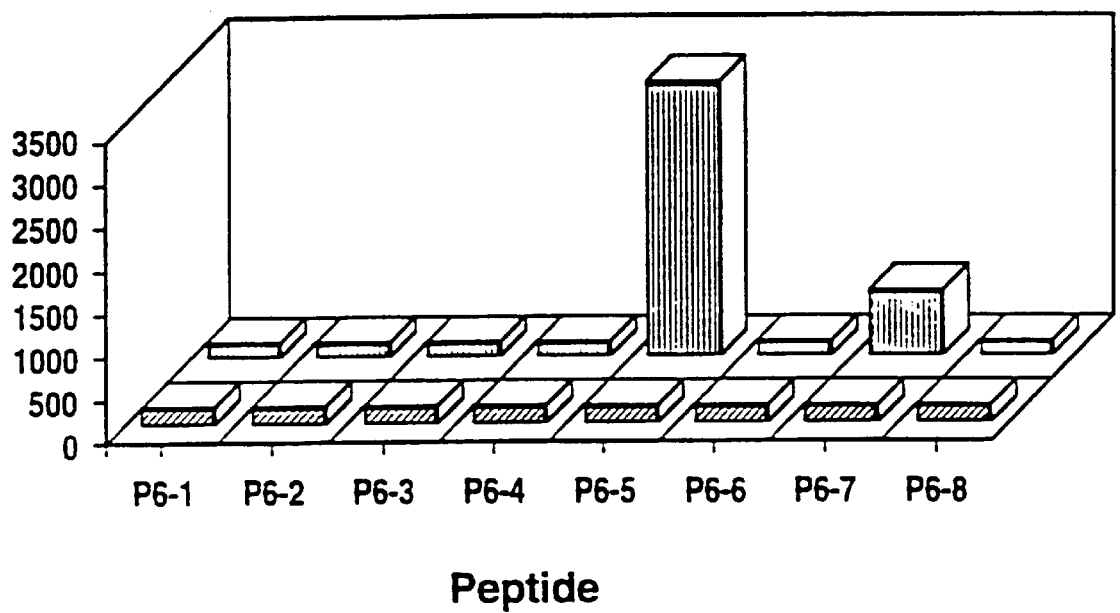
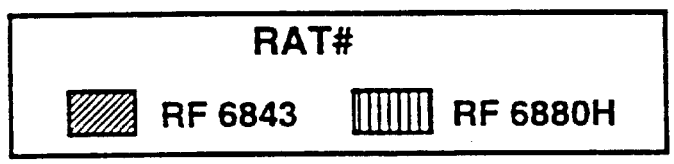
FIG. 8B.

HAEMOPHILUS P6 PEPTIDE ANTIBODY ELISA
RABBIT ANTISERUM
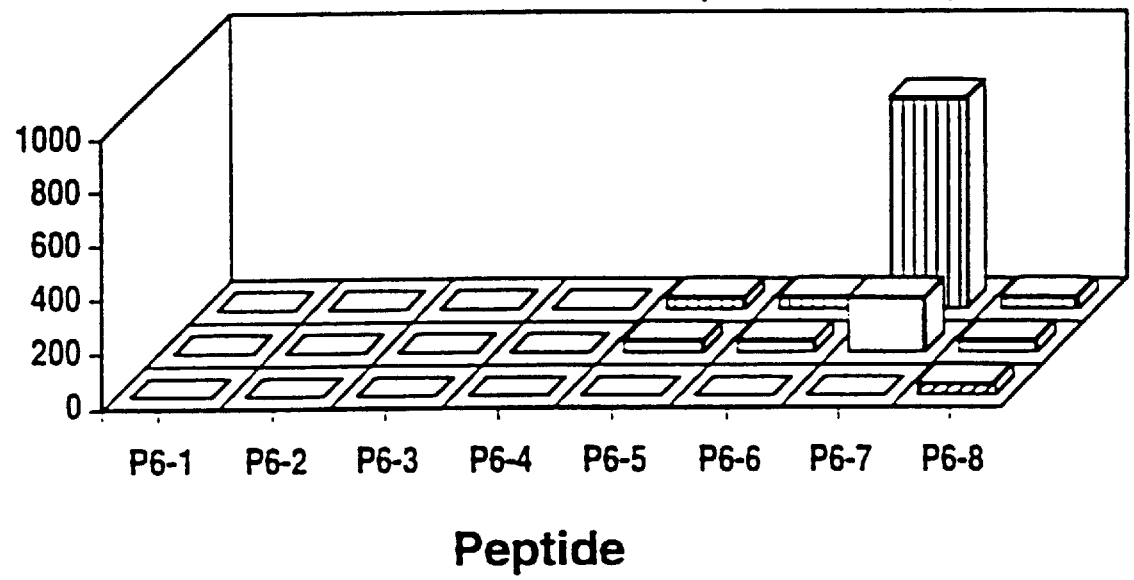
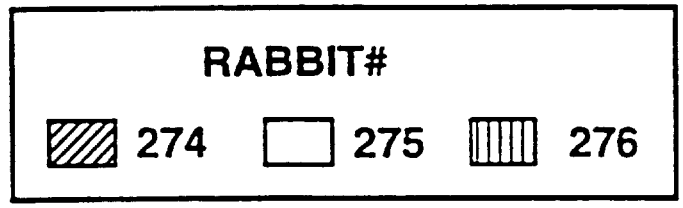
FIG. 8C.

(13) R=H, REPEATING UNIT
(14) R=DMT, ANCHORING UNIT

Scheme 1

Scheme 2

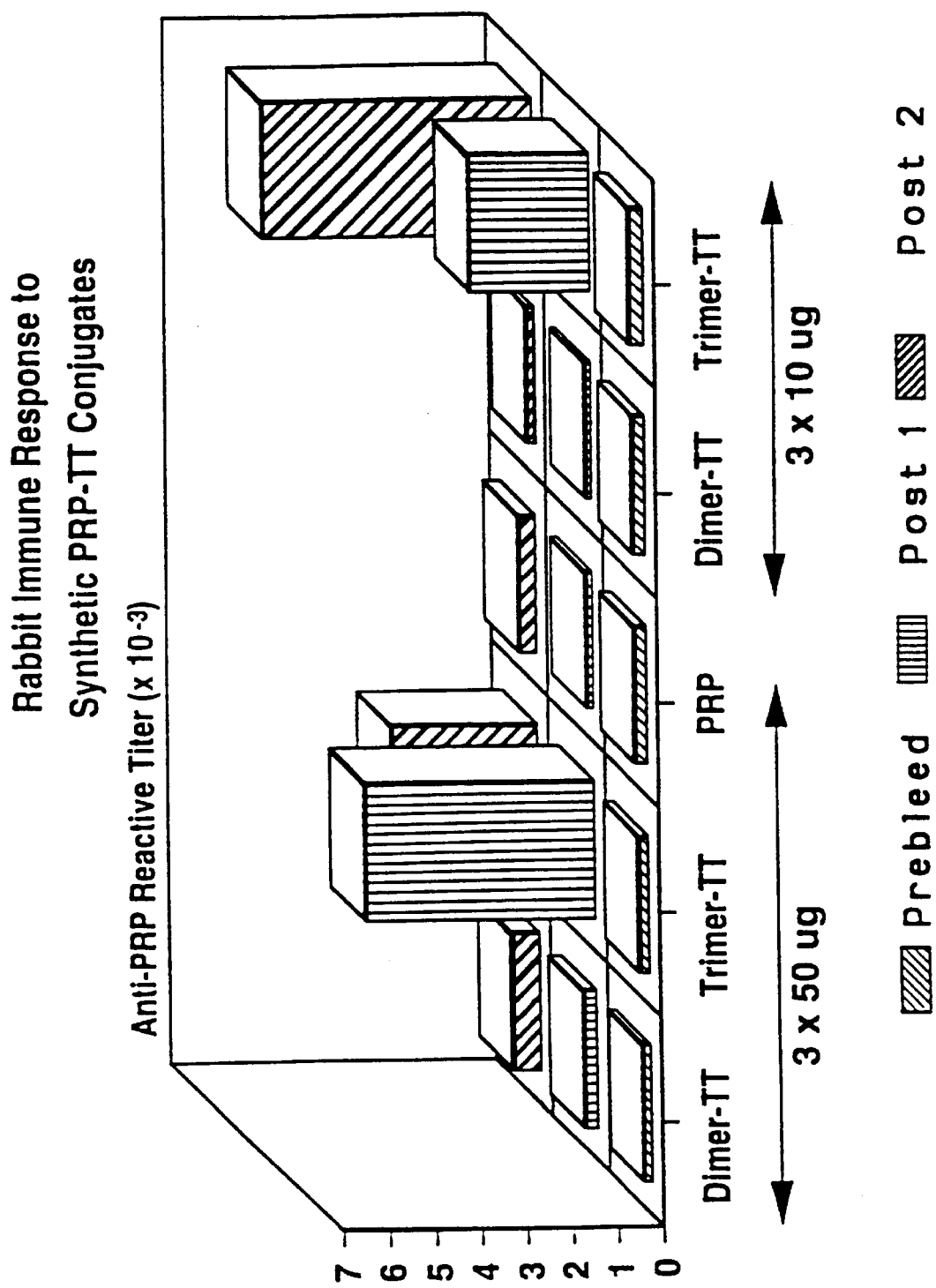

SEQUENCE LISTING (1) GENERAL INFORMATION:

(iii) NUMBER OF SEQUENCES: 56

(2) INFORMATION FOR SEQ ID NO: 1:

(i) SEQUENCE CHARACTERISTICS:
       (A) LENGTH: 29 amino acids
       (B) TYPE: amino acid
       (C) STRANDEDNESS: single
       (D) TOPOLOGY: linear (xi) SEQUENCE DESCRIPTION: SEQ ID NO: 1:

Ala Ala Phe Gln Leu Ala Glu Val Ser Thr Ser Gly Leu Gly Arg Ala
1               5                   10                  15

Tyr Ala Gly Glu Ala Ala Ile Ala Asp Asn Ala Ser Val
            20                  25

(2) INFORMATION FOR SEQ ID NO: 2:

(i) SEQUENCE CHARACTERISTICS:
       (A) LENGTH: 29 amino acids
       (B) TYPE: amino acid
       (C) STRANDEDNESS: single
       (D) TOPOLOGY: linear (xi) SEQUENCE DESCRIPTION: SEQ ID NO: 2:

Gly Asp Val Thr Ser Tyr Ala Gln Ile Ile Thr Asn Gln Ile Gly Met
1               5                   10                  15

Lys Ala Ile Lys Asp Gly Ser Ala Ser Gln Arg Asn Val
            20                  25

(2) INFORMATION FOR SEQ ID NO: 3:

(i) SEQUENCE CHARACTERISTICS:
       (A) LENGTH: 35 amino acids
       (B) TYPE: amino acid
       (C) STRANDEDNESS: single
       (D) TOPOLOGY: linear (xi) SEQUENCE DESCRIPTION: SEQ ID NO: 3:

Val Asn Asp Lys Phe Ala Leu Gly Ala Gly Met Asn Val Asn Phe Gly
1               5                   10                  15

Leu Lys Ser Glu Tyr Asp Asp Ser Tyr Asp Ala Gly Val Phe Gly Gly
            20                  25                  30

Lys Thr Asp
        35

(2) INFORMATION FOR SEQ ID NO: 4:

(i) SEQUENCE CHARACTERISTICS:
       (A) LENGTH: 29 amino acids
       (B) TYPE: amino acid
       (C) STRANDEDNESS: single
       (D) TOPOLOGY: linear (xi) SEQUENCE DESCRIPTION: SEQ ID NO: 4:

Tyr Ala Lys Ala Gln Val Glu Arg Asn Ala Gly Leu Ile Ala Asp Ser
1               5                   10                  15

Val Lys Asp Asn Gln Ile Thr Ser Ala Leu Ser Thr Gln
            20                  25

(2) INFORMATION FOR SEQ ID NO: 5:

(i) SEQUENCE CHARACTERISTICS:
            (A) LENGTH: 29 amino acids
            (B) TYPE: amino acid
            (C) STRANDEDNESS: single
            (D) TOPOLOGY: linear (xi) SEQUENCE DESCRIPTION: SEQ ID NO: 5:

Ala Leu Ser Thr Gln Gln Glu Phe Arg Asp Leu Lys Lys Tyr Leu Pro
 1               5                  10                  15

Ser Lys Asp Lys Ser Val Val Ser Leu Gln Asp Arg Ala
                20                  25

(2) INFORMATION FOR SEQ ID NO: 6:

(i) SEQUENCE CHARACTERISTICS:
            (A) LENGTH: 28 amino acids
            (B) TYPE: amino acid
            (C) STRANDEDNESS: single
            (D) TOPOLOGY: linear (xi) SEQUENCE DESCRIPTION: SEQ ID NO: 6:

Ala Gly Val Met Tyr Gln Phe Asn Glu Ala Asn Arg Ile Gly Leu Ala
 1               5                  10                  15

Tyr His Ser Lys Val Asp Ile Asp Phe Ala Asp Arg
                20                  25

(2) INFORMATION FOR SEQ ID NO: 7:

(i) SEQUENCE CHARACTERISTICS:
            (A) LENGTH: 36 amino acids
            (B) TYPE: amino acid
            (C) STRANDEDNESS: single
            (D) TOPOLOGY: linear (xi) SEQUENCE DESCRIPTION: SEQ ID NO: 7:

Ile Asp Phe Ala Asp Arg Thr Ala Thr Ser Leu Glu Ala Asn Val Ile
 1               5                  10                  15

Lys Glu Gly Lys Lys Gly Asn Leu Thr Phe Thr Leu Pro Asp Tyr Leu
                20                  25                  30

Glu Leu Ser Gly
            35

(2) INFORMATION FOR SEQ ID NO: 8:

(i) SEQUENCE CHARACTERISTICS:
            (A) LENGTH: 34 amino acids
            (B) TYPE: amino acid
            (C) STRANDEDNESS: single
            (D) TOPOLOGY: linear (xi) SEQUENCE DESCRIPTION: SEQ ID NO: 8:

Leu Glu Leu Ser Gly Phe His Gln Leu Thr Asp Lys Leu Ala Val His
 1               5                  10                  15

Tyr Ser Tyr Lys Tyr Thr His Trp Ser Arg Leu Thr Lys Leu His Ala
                20                  25                  30

Ser Phe (2) INFORMATION FOR SEQ ID NO: 9:

(i) SEQUENCE CHARACTERISTICS:
            (A) LENGTH: 25 amino acids
            (B) TYPE: amino acid
            (C) STRANDEDNESS: single
            (D) TOPOLOGY: linear (xi) SEQUENCE DESCRIPTION: SEQ ID NO: 9:

Lys Leu His Ala Ser Phe Glu Asp Gly Lys Lys Ala Phe Asp Lys Glu
 1               5                  10                  15

Leu Gln Tyr Ser Asn Asn Ser Arg Val
         20                  25

(2) INFORMATION FOR SEQ ID NO: 10:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO: 10:

Leu Tyr Glu Lys Leu Thr Leu Arg Ala Gly Ile Ala Tyr Asp Gln Ala
1                5                  10                  15

Ala Ser Arg His His Arg Ser Ala Ala Ile Pro Asp Thr Asp Arg Thr
                20                  25                  30

(2) INFORMATION FOR SEQ ID NO: 11:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO: 11:

Leu Ser Val Asp Leu Gly Tyr Ala Tyr Leu Lys Gly Lys Lys Val His
1                5                  10                  15

Phe Lys Glu Val Lys Thr Ile Gly Asp Lys Arg Thr Leu
                20                  25

(2) INFORMATION FOR SEQ ID NO: 12:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 12:

Leu Phe Lys Thr Ala Gln Phe Ser Thr Gly Gly Val Tyr Ile Asp Ser
1                5                  10                  15

Arg Ile Asn Met Asn Gly Asp Val Thr Ser
                20                  25

(2) INFORMATION FOR SEQ ID NO: 13:

(i) SEQUENCE CHARACTERISTICS:
        (A) LENGTH: 38 amino acids
        (B) TYPE: amino acid
        (C) STRANDEDNESS: single
        (D) TOPOLOGY: linear (xi) SEQUENCE DESCRIPTION: SEQ ID NO: 13:

Phe Lys Glu Val Lys Thr Ile Gly Asp Lys Arg Thr Leu Thr Leu Asn
1                5                  10                  15

Thr Thr Ala Asn Tyr Thr Ser Gln Ala His Ala Asn Leu Tyr Gly Leu
                20                  25                  30

Asn Leu Asn Tyr Ser Phe
        35

(2) INFORMATION FOR SEQ ID NO: 14:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO: 14:

Phe Lys Glu Ala Gln Gln Ala Ala Gly Gly Phe Ile Thr Thr Thr Ala
1               5                   10                  15

Asn Tyr Thr Ser Gln Ala His Ala Asn Leu Tyr Gly Leu Asn Leu Asn
                20                  25                  30

Tyr Ser Phe
        35

(2) INFORMATION FOR SEQ ID NO: 15:

(i) SEQUENCE CHARACTERISTICS:
        (A) LENGTH: 39 amino acids
        (B) TYPE: amino acid
        (C) STRANDEDNESS: single
        (D) TOPOLOGY: linear (xi) SEQUENCE DESCRIPTION: SEQ ID NO: 15:

Asp Ser Val Lys Asp Asn Asp Ile Thr Ser Ala Leu Ser Thr Gln Gln
1               5                   10                  15

Glu Phe Arg Asp Leu Lys Lys Tyr Leu Pro Ser Lys Asp Lys Ser Val
                20                  25                  30

Val Ser Leu Gln Asp Arg Ala
        35

(2) INFORMATION FOR SEQ ID NO: 16:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 16:

Ala Val Val Tyr Asn Asn Glu Gly Thr Asn Val Glu Leu Gly
1               5                   10

(2) INFORMATION FOR SEQ ID NO: 17:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 17:

Gly Thr Asn Val Glu Leu Gly Gly Arg Leu Ser Ile
1               5                   10

(2) INFORMATION FOR SEQ ID NO: 18:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO: 18:

Leu Ser Ile Ile Ala Glu Gln Ser Asn Ser Thr Val Asp Asn Gln Lys
1               5                   10                  15

(2) INFORMATION FOR SEQ ID NO: 19:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 19:

Val Asp Asn Gln Lys Gln Gln His Gly Ala Leu Arg Asn Gln Gly Ser
1               5                   10                  15

Arg Phe His Ile Lys Ala Thr His Asn Phe Gly Asp
                20                  25

(2) INFORMATION FOR SEQ ID NO: 20:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO: 20:

Phe Gly Asp Gly Phe Tyr Ala Gln Gly Tyr Leu Glu Thr Arg Phe Val
1               5                   10                  15

Thr Lys Ala Ser Glu Asn Gly Ser Asp Asn Phe Gly Asp
                20                  25

(2) INFORMATION FOR SEQ ID NO: 21:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 21:

Phe Gly Asp Ile Thr Ser Lys Tyr Ala Tyr Val Thr Leu Gly Asn Lys
1               5                   10                  15

Ala Phe Gly Glu Val Lys Leu Gly Arg Ala Lys Thr
                20                  25

(2) INFORMATION FOR SEQ ID NO: 22:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 22:

Gly Arg Ala Lys Thr Ile Ala Asp Gly Ile Thr Ser Ala Glu Asp Lys
1               5                   10                  15

Glu Tyr Gly Val Leu Asn Asn Ser Asp Tyr Ile Pro
                20                  25

(2) INFORMATION FOR SEQ ID NO: 23:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 23:

Ser Asp Tyr Ile Pro Thr Ser Gly Asn Thr Val Gly Tyr Thr Phe Lys
1               5                   10                  15

Gly Ile Asp Gly Leu Val Leu Gly Ala Asn
                20                  25

(2) INFORMATION FOR SEQ ID NO: 24:

(i) SEQUENCE CHARACTERISTICS:
        (A) LENGTH: 27 amino acids
        (B) TYPE: amino acid
        (C) STRANDEDNESS: single (D) TOPOLOGY: linear (xi) SEQUENCE DESCRIPTION: SEQ ID NO: 24:

Gly Ala Asn Tyr Leu Leu Ala Gln Lys Arg Glu Gly Ala Lys Gly Glu
1               5                   10                  15

Asn Lys Arg Pro Asn Asp Lys Ala Gly Glu Val
            20                  25

(2) INFORMATION FOR SEQ ID NO: 25:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 25:

Ala Gly Glu Val Arg Ile Gly Glu Ile Asn Gly Ile Gln Val Gly
1               5                   10                  15

Ala Lys Tyr Asp Ala Asn Asp Ile Val Ala
            20                  25

(2) INFORMATION FOR SEQ ID NO: 26:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 26:

Asp Ile Val Ala Lys Ile Ala Tyr Gly Arg Thr Asn Tyr Lys Tyr Asn
1               5                   10                  15

Glu Ser Asp Glu His Lys Gln Gln Leu Asn Gly
            20                  25

(2) INFORMATION FOR SEQ ID NO: 27:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 27:

Gly Val Leu Ala Thr Leu Gly Tyr Arg Phe Ser Asp Leu Gly Leu Leu
1               5                   10                  15

Val Ser Leu Asp Ser Gly Tyr Ala Lys Thr
            20                  25

(2) INFORMATION FOR SEQ ID NO: 28:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO: 28:

Tyr Ala Lys Thr Lys Asn Tyr Lys Ile Lys His Glu Lys Arg Tyr Phe
1               5                   10                  15

Val Ser Pro Gly Phe Gln Tyr Glu Leu
            20                  25

(2) INFORMATION FOR SEQ ID NO: 29:

(i) SEQUENCE CHARACTERISTICS:
        (A) LENGTH: 27 amino acids (B) TYPE: amino acid
        (C) STRANDEDNESS: single
        (D) TOPOLOGY: linear (xi) SEQUENCE DESCRIPTION: SEQ ID NO: 29:

Tyr Glu Leu Met Glu Asp Thr Asn Val Tyr Gly Asn Phe Lys Tyr Glu
1               5                   10                  15

Arg Thr Ser Val Asp Gln Gly Glu Lys Thr Arg
            20                  25

(2) INFORMATION FOR SEQ ID NO: 30:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO: 30:

Gly Glu Lys Thr Arg Glu Gln Ala Val Leu Phe Gly Val Asp His Lys
1               5                   10                  15

Leu His Lys Gln Leu Leu
            20

(2) INFORMATION FOR SEQ ID NO: 31:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO: 31:

Lys Gln Leu Leu Thr Tyr Ile Glu Gly Ala Tyr Ala Arg Thr Arg Thr
1               5                   10                  15

Thr (2) INFORMATION FOR SEQ ID NO: 32:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 32:

Ala Arg Thr Arg Thr Thr Glu Thr Gly Lys Gly Val Lys Thr Glu Lys
1               5                   10                  15

Glu Lys Ser Val Gly Val Gly Leu Arg Val Tyr Phe
            20                  25

(2) INFORMATION FOR SEQ ID NO: 33:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 33:

Gly Ala Asn Tyr Leu Leu Ala Gln Lys Arg Glu Gly Ala Lys Met Ala
1               5                   10                  15

Asn Lys Leu Pro Asn Asn Lys Ala Gly Glu Val
            20                  25

(2) INFORMATION FOR SEQ ID NO: 34:

(i) SEQUENCE CHARACTERISTICS:

(A) LENGTH: 27 amino acids
(B) TYPE: amino acid
(C) STRANDEDNESS: single
(D) TOPOLOGY: linear (xi) SEQUENCE DESCRIPTION: SEQ ID NO: 34:

```
Gly Ala Asn Tyr Leu Leu Ala Gln Lys Arg Glu Gly Ala Lys Gly Glu
1               5                   10                  15
Asn Lys Gln Pro Asn Asp Lys Ala Gly Glu Val
            20                  25
```

(2) INFORMATION FOR SEQ ID NO: 35:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO: 35:

```
Cys Ser Ser Ser Asn Asn Asp Ala Ala Gly Asn Gly Ala Ala Gln Thr
1               5                   10                  15
Phe Gly Gly Tyr Ser Val
            20
```

(2) INFORMATION FOR SEQ ID NO: 36:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO: 36:

```
Gly Tyr Ser Val Ala Asp Leu Gln Gln Arg Tyr Asn Thr Val Tyr Phe
1               5                   10                  15
Gly Phe Asp Lys Tyr Asp Ile
            20
```

(2) INFORMATION FOR SEQ ID NO: 37:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO: 37:

```
Gly Phe Asp Lys Tyr Asp Ile Thr Gly Glu Tyr Val Gln Ile Leu Asp
1               5                   10                  15
Ala His Ala Ala Tyr Leu Asn Ala
            20
```

(2) INFORMATION FOR SEQ ID NO: 38:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO: 38:

```
Ala Tyr Leu Asn Ala Thr Pro Ala Ala Lys Val Leu Val Glu Gly Asn
1               5                   10                  15
Thr Asp Glu Arg Gly Thr Pro Glu
            20
```

(2) INFORMATION FOR SEQ ID NO: 39:

```
   (i) SEQUENCE CHARACTERISTICS:
       (A) LENGTH: 24 amino acids
       (B) TYPE: amino acid
       (C) STRANDEDNESS: single
       (D) TOPOLOGY: linear (xi) SEQUENCE DESCRIPTION: SEQ ID NO: 39:

Arg Gly Thr Pro Glu Tyr Asn Ile Ala Leu Gly Gln Arg Arg Ala Asp
1               5                   10                  15

Ala Val Lys Gly Tyr Leu Ala Gly
            20

(2) INFORMATION FOR SEQ ID NO: 40:

(i) SEQUENCE CHARACTERISTICS:
       (A) LENGTH: 25 amino acids
       (B) TYPE: amino acid
       (C) STRANDEDNESS: single
       (D) TOPOLOGY: linear (xi) SEQUENCE DESCRIPTION: SEQ ID NO: 40:

Val Lys Gly Tyr Leu Ala Gly Tyr Leu Ala Gly Lys Gly Val Asp Ala
1               5                   10                  15

Gly Lys Leu Gly Thr Val Ser Tyr Gly
            20                  25

(2) INFORMATION FOR SEQ ID NO: 41:

(i) SEQUENCE CHARACTERISTICS:
       (A) LENGTH: 30 amino acids
       (B) TYPE: amino acid
       (C) STRANDEDNESS: single
       (D) TOPOLOGY: linear (xi) SEQUENCE DESCRIPTION: SEQ ID NO: 41:

Gly Thr Val Ser Tyr Gly Glu Glu Lys Pro Ala Val Leu Gly His Asp
1               5                   10                  15

Glu Ala Ala Tyr Ser Lys Asn Arg Arg Ala Val Leu Ala Tyr
            20                  25                  30

(2) INFORMATION FOR SEQ ID NO: 42:

(i) SEQUENCE CHARACTERISTICS:
       (A) LENGTH: 43 amino acids
       (B) TYPE: amino acid
       (C) STRANDEDNESS: single
       (D) TOPOLOGY: linear (xi) SEQUENCE DESCRIPTION: SEQ ID NO: 42:

Val Lys Thr Ile Gly Asp Lys Arg Thr Leu Thr Leu Asn Thr Cys Ala
1               5                   10                  15

Arg Thr Arg Thr Thr Glu Thr Gly Lys Gly Val Lys Thr Glu Lys Glu
            20                  25                  30

Lys Ser Val Gly Val Gly Leu Arg Val Tyr Phe
            35                  40

(2) INFORMATION FOR SEQ ID NO: 43:

(i) SEQUENCE CHARACTERISTICS:
       (A) LENGTH: 43 amino acids
       (B) TYPE: amino acid
       (C) STRANDEDNESS: single
       (D) TOPOLOGY: linear (xi) SEQUENCE DESCRIPTION: SEQ ID NO: 43:

Val Lys Thr Ile Gly Asp Lys Asn Thr Leu Thr Leu Asn Thr Phe Gly
1               5                   10                  15
```

Asp Gly Phe Tyr Ala Gln Gly Tyr Leu Glu Thr Arg Phe Val Thr Lys
            20                  25                  30

Ala Ser Glu Asn Gly Ser Asn Phe Gly Asp Cys
            35                  40

(2) INFORMATION FOR SEQ ID NO: 44:

(i) SEQUENCE CHARACTERISTICS:
        (A) LENGTH: 42 amino acids
        (B) TYPE: amino acid
        (C) STRANDEDNESS: single
        (D) TOPOLOGY: linear (xi) SEQUENCE DESCRIPTION: SEQ ID NO: 44:

Val Lys Thr Ile Gly Asp Lys Asn Thr Leu Thr Leu Asn Thr Cys Gly
1               5                   10                  15

Ala Asn Tyr Leu Leu Ala Gln Lys Arg Glu Gly Ala Lys Gly Glu Asn
            20                  25                  30

Lys Arg Pro Asn Asp Lys Ala Gly Glu Val
            35                  40

(2) INFORMATION FOR SEQ ID NO: 45:

(i) SEQUENCE CHARACTERISTICS:
        (A) LENGTH: 42 amino acids
        (B) TYPE: amino acid
        (C) STRANDEDNESS: single
        (D) TOPOLOGY: linear (xi) SEQUENCE DESCRIPTION: SEQ ID NO: 45:

Val Lys Thr Ile Gly Asp Lys Arg Thr Leu Thr Leu Asn Thr Asp Ile
1               5                   10                  15

Val Ala Lys Ile Ala Tyr Gly Arg Thr Asn Tyr Lys Tyr Asn Glu Ser
            20                  25                  30

Asp Glu His Lys Gln Gln Leu Asn Gly Cys
            35                  40

(2) INFORMATION FOR SEQ ID NO: 46:

(i) SEQUENCE CHARACTERISTICS:
        (A) LENGTH: 40 amino acids
        (B) TYPE: amino acid
        (C) STRANDEDNESS: single
        (D) TOPOLOGY: linear (xi) SEQUENCE DESCRIPTION: SEQ ID NO: 46:

Val Lys Thr Ile Gly Asp Lys Arg Thr Leu Thr Leu Asn Thr Tyr Ala
1               5                   10                  15

Lys Thr Lys Asn Tyr Lys Ile Lys His Glu Lys Arg Tyr Phe Val Ser
            20                  25                  30

Pro Gly Phe Gln Tyr Glu Leu Cys
            35                  40

(2) INFORMATION FOR SEQ ID NO: 47:

(i) SEQUENCE CHARACTERISTICS:
        (A) LENGTH: 55 amino acids
        (B) TYPE: amino acid
        (C) STRANDEDNESS: single
        (D) TOPOLOGY: linear (xi) SEQUENCE DESCRIPTION: SEQ ID NO: 47:

Gly Tyr Leu Glu Thr Arg Phe Val Thr Lys Ala Ser Glu Asn Gly Ser
1               5                   10                  15

Asp Phe Lys Glu Val Lys Thr Ile Gly Asp Lys Arg Thr Leu Thr Leu
            20                  25                  30

Asn Thr Thr Ala Asn Tyr Thr Ser Gln Ala His Ala Asn Leu Tyr Gly
         35                  40                  45

Leu Asn Leu Asn Tyr Ser Phe
         50                  55

(2) INFORMATION FOR SEQ ID NO: 48:

(i) SEQUENCE CHARACTERISTICS:
        (A) LENGTH: 53 amino acids
        (B) TYPE: amino acid
        (C) STRANDEDNESS: single
        (D) TOPOLOGY: linear (xi) SEQUENCE DESCRIPTION: SEQ ID NO: 48:

Ala Lys Gly Glu Asn Lys Arg Pro Asn Asp Lys Ala Gly Glu Val Phe
1               5                  10                  15

Lys Glu Val Lys Thr Ile Gly Asp Lys Arg Thr Leu Thr Leu Asn Thr
         20                  25                  30

Thr Ala Asn Tyr Thr Ser Gln Ala His Ala Asn Leu Tyr Gly Leu Asn
         35                  40                  45

Leu Asn Tyr Ser Phe
         50

(2) INFORMATION FOR SEQ ID NO: 49:

(i) SEQUENCE CHARACTERISTICS:
        (A) LENGTH: 54 amino acids
        (B) TYPE: amino acid
        (C) STRANDEDNESS: single
        (D) TOPOLOGY: linear (xi) SEQUENCE DESCRIPTION: SEQ ID NO: 49:

Ala Arg Thr Arg Thr Thr Glu Thr Gly Lys Gly Val Lys Thr Glu Lys
1               5                  10                  15

Phe Lys Glu Val Lys Thr Ile Gly Asp Lys Arg Thr Leu Thr Leu Asn
         20                  25                  30

Thr Thr Ala Asn Tyr Thr Ser Gln Ala His Ala Asn Leu Tyr Gly Leu
         35                  40                  45

Asn Leu Asn Tyr Ser Phe
         50

(2) INFORMATION FOR SEQ ID NO: 50:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO: 50:

Gly Pro Lys Glu Pro Phe Arg Asp Tyr Val Asp Arg Phe Tyr Lys
1               5                  10                  15

(2) INFORMATION FOR SEQ ID NO: 51:

(i) SEQUENCE CHARACTERISTICS:
        (A) LENGTH: 29 amino acids
        (B) TYPE: amino acid
        (C) STRANDEDNESS: single
        (D) TOPOLOGY: linear (v) FRAGMENT TYPE: C-terminal (xi) SEQUENCE DESCRIPTION: SEQ ID NO: 51:

Tyr Ala Lys Ala Gln Val Glu Arg Asn Ala Gly Leu Ile Ala Asp Ser
1               5                  10                  15

Val Lys Asp Asn Gln Ile Thr Ser Ala Leu Ser Thr Gln (2) INFORMATION FOR SEQ ID NO: 52:

(i) SEQUENCE CHARACTERISTICS:
        (A) LENGTH: 29 amino acids
        (B) TYPE: amino acid
        (C) STRANDEDNESS: single
        (D) TOPOLOGY: linear (v) FRAGMENT TYPE: N-terminal (xi) SEQUENCE DESCRIPTION: SEQ ID NO: 52:

Tyr Ala Lys Ala Gln Val Glu Arg Asn Ala Gly Leu Ile Ala Asp Ser
1               5                   10                  15

Val Lys Asp Asn Gln Ile Thr Ser Ala Leu Ser Thr Gln
            20                  25

(2) INFORMATION FOR SEQ ID NO: 53:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 53:

Asp Ile Val Ala Lys Ile Ala Tyr Gly Arg Thr Asn Tyr Lys Tyr Asn
1               5                   10                  15

Glu Ser Asp Glu His Lys Gln Gln Leu Asn Gly
            20                  25

(2) INFORMATION FOR SEQ ID NO: 54:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 54:

Asp Ile Val Ala Lys Ile Ala Tyr Gly Arg Thr Asn Tyr Lys Tyr Asn
1               5                   10                  15

Glu Ser Asp Glu His Lys Gln Gln Leu Asn Gly
            20                  25

(2) INFORMATION FOR SEQ ID NO: 55:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO: 55:

Val Lys Gly Tyr Leu Ala Gly Tyr Leu Ala Gly Lys Gly Val Asp Ala
1               5                   10                  15

Gly Lys Leu Gly Thr Val Ser Tyr Gly
            20                  25

(2) INFORMATION FOR SEQ ID NO: 56:

(i) SEQUENCE CHARACTERISTICS:
        (A) LENGTH: 15 amino acids
        (B) TYPE: amino acid
        (C) STRANDEDNESS: single (D) TOPOLOGY: linear (xi) SEQUENCE DESCRIPTION: SEQ ID NO: 56:

```
Gly Pro Lys Glu Pro Phe Arg Asp Tyr Val Asp Arg Phe Tyr Lys
1               5                   10                  15
```

SYNTHETIC HAEMOPHILUS INFLUENZAE CONJUGATE VACCINE

FIELD OF INVENTION

The present invention relates to synthetic vaccines against *Haemophilus influenzae* (Hi) infection. In particular, the invention relates to the use of potent T-helper cell determinants (THDs) and B-cell epitopes (BEs) of the outer membrane proteins (OMPs) P1, P2 and P6 of Hi, covalently linked to synthetic oligosaccharides containing repeating units of polyribosylribitol phosphate (sPRP) to form immunogenic synthetic PRP-peptide conjugate vaccines that can elicit high titers of anti-PRP and anti-OMP antibodies in mammals.

BACKGROUND TO THE INVENTION

*Haemophilus influenzae* type b (Hib) is a major cause of bacterial meningitis in children under five years of age (refs. 1, 2. The literature references are identified at the end of this disclosure). The bacterium is protected from phagocytosis by a polysaccharide capsule that is a repeating polymer of polyribosyl ribitol phosphate (PRP). Antibodies induced against the capsular polysaccharide of the organism are protective (ref. 3). Effective conjugate vaccines in which PRP is linked to different carrier proteins such as diphtheria toxoid (PRP-D), tetanus toxoid (PRP-T), CRM 197 (HbOC) and the outer membrane protein of *Neisseria meninaitidis* have been developed (refs. 4, 5). However, these conjugate vaccines do not protect against other invasive encapsulated *H. influenzae* type a and c strains and, more importantly, against non-encapsulated non-typeable *H. influenzae* strains that are one of the common causes of otitis media for which there is no vaccine. Therefore, the inclusion of selected non-encapsulated *H. influenzae* immunogens in current Hib vaccines is necessary to develop a universal Hi vaccine.

Granoff and Munson (ref. 6) have reported that antibodies directed against Hib outer membrane proteins (OMP) P1, P2 and P6 were protective in the infant rat model of bacteremia. Therefore, a promising strategy for designing a universal *H. influenzae* vaccine with enhanced protective ability would be to use either purified OMPs or their protective epitopes as additional immunogens and carriers for PRP. The gene coding for P1 has been cloned from several different Hib subtypes (refs. 7, 8). The comparative analysis of P1 protein sequences from these Hib isolates revealed the existence of three hypervariable regions. Indeed, the P1-specific MAbs reported by Hansen's group recognize only 50% of the Hib isolates tested (refs. 7, 9). For the P2 protein, although the nucleotide sequences of the P2 gene isolated from two different Hib subtypes (1H and 3L) were found to be identical (refs. 10, 11), some amino acid variability was found among the P2 sequences of two other Hib subtypes (2L and 6U) (ref. 11). In contrast, analysis of antigenic determinants, gene sequences and restriction fragment length polymorphisms experiments indicated that the P6 protein was highly conserved among all strains of Hi (ref. 12).

Recent studies showed that a murine P1-specific monoclonal antibody (MAb 7C8) and rabbit antisera raised against purified P1 from either typeable or non-typeable *H. influenzae* strains were protective in animal models (refs. 9, 13, 14). Murphy and Bartos (ref. 15) also reported that a monoclonal antibody recognizing a surface-exposed epitope of a non-typeable *H. influenzae* P2 protein had bactericidal activity in vitro. Anti-P1 and anti-P2 monoclonal antibodies were found to cross-react with typeable and non-typeable strains of *H. influenzae* (refs. 16 to 18). However, there are still serious concerns with the use of whole native Hib OMPs as an efficacious universal vaccine against both typeable and non-typeable Hi. Firstly, children who recover from otitis media caused by non-typeable Hi generally develop bactericidal antibodies against variable antigens, such as P2 and lipooligosaccharides. Secondly, the P1 and P2 cross-protective epitopes described above have not yet been identified. Thirdly, it was reported (ref. 12) that the epitope (s) recognized by anti-P6 bactericidal antibodies are expressed in small amounts on the bacterial surface, and recurrent infections may thus be possible. Fourthly, little is known about the role of cellular immune responses to OMPs. The immunodominant T-helper cell epitopes of Hi OMPs have not been characterized. Therefore, the identification of the functional T-helper cell epitopes and the conserved, surface-exposed and/or protective B-cell epitopes of the P1, P2 and P6 proteins is necessary to determine whether these epitopes can elicit immune responses against Hi infection.

Methods for inducing immunity against disease are constantly improving and the current trend is to use smaller and well defined materials as antigens. The objective is to eliminate the potential side-effects of certain native immunogens, while preserving their immunogenicity and ability to confer protection against disease. Recent studies have indicated that immunization of experimental animals with synthetic peptides representing specific regions of viral or bacterial proteins can induce immune responses against the parent proteins, and neutralize their biological functions (refs. 19 to 22). Thus, synthetic peptides are potential candidate antigens for the production of inexpensive and safe vaccines against infectious diseases. Recent progress in fundamental immunology has revealed that good and effective immunogens should contain two distinct functional antigenic determinants (epitopes). One epitope (T-cell epitope) is designed to be presented in the appropriate MHC class II antigen context to the immune system and induce T-helper cell activity. The other epitope (B-cell epitope) must be recognized by a cognate B-cell antigen receptor to elicit antibody production (refs. 23 to 26). Therefore, in order to produce a potent and efficacious synthetic vaccine, both functional T-helper and B-cell epitopes must be included in the synthetic construct.

Synthetic PRP dimer, trimer and tetramer have been synthesized, purified and conjugated to carrier proteins for animal immunogenicity studies (refs. 27, 28). These studies showed that synthetic PRP trimer-protein conjugates in the presence of strong adjuvants such as complete Freund's adjuvant (CFA) could elicit anti-PRP antibody responses in experimental animals.

Instead of using conventional heterologous carrier proteins, our strategy utilizes synthetic peptides containing immunodominant epitopes from Hi OMPs as additional antigens and as carriers for PRP to develop the first generation of fully synthetic PRP-peptide conjugate vaccines with enhanced protective ability and autologous T-cell priming. Such vaccines also have other potential advantages over the existing vaccines in which PRP is conjugated to a foreign protein (diphtheria toxoid (PRP-D), or tetanus toxoid (PRP-T), or CRM197 (HbOC), or OMP of *Neisseria menincitidis*). Firstly, the use of synthetic Hi vaccines should help reduce the amount of D or T in any future multivalent combined vaccines, thus minimizing the potential risk of hyperimmunization against these carrier proteins. Secondly, PRP may be coupled to a conserved protective epitope to produce a vaccine against both invasive Hi disease and otitis media.

| ABBREVIATIONS AND DEFINITIONS | |
|---|---|
| $CRM_{197}$ | a non-toxic protein antigenically cross-reactive with diphtheria toxin |
| Hi | *Haemophilus influenzae* |
| Hib | *Haemophilus influenzae* type B |
| MAP | multiple antigen peptide |
| MBS | m-maleimidobenzoyl-N-hydroxysuccinimide |
| OMP | outer membrane protein |
| PEG | polyethylene glycol monomethyl ether |
| PRP | polyriboseribitol phosphate |

ASPECTS OF THE INVENTION

One aspect of the present invention is directed towards the provision of immunogenic synthetic conjugate vaccines comprising synthetic PRP oligomers and antigenic determinants of Hi outer membrane proteins.

The present invention, in another aspect, is directed towards the provision of synthetic PRP-peptide conjugate vaccines comprising a defined length of synthetic PRP oligomers.

A further aspect of the present invention is directed towards the provision of a chemical process that efficiently produces synthetic PRP with chemically reactive functional groups allowing for their site-directed conjugation to an antigenic determinant of Hi outer membrane proteins, using polyethylene glycol monomethyl ether (PEG) as solid support.

The present invention, in a yet further aspect of the invention is directed towards the provision of a method which can be used to optimize the immunogenicity of the synthetic PRP-peptide conjugates, selecting the correct orientation of sugar moieties with respect to the T-cell epitope.

An additional aspect of the present invention is directed towards the provision of a chemical process that can enhance the immunogenicity of carbohydrates, using multiple antigen peptide system (MAPs) containing antigenic determinants of Hib as carriers to increase the density of carbohydrate moeities in synthetic PRP-peptide conjugates.

The present invention, in yet an additional aspect, is directed towards the provision of a universal Hi vaccine comprising immunogenic synthetic PRP-peptide conjugates and cross-protective Hi antigens.

A yet another aspect of the present invention is directed towards the provision of a new generation of polyvalent vaccines comprising immunogenic synthetic PRP-peptide conjugates, and Hi antigens combined with other vaccines, such as DTP-polio, *Neisseria meningitidis* serotype A, B, C, abd W, and *S. pneumoniae* serotype 6B, 14, 19F and 23F.

The present invention, in a further aspect, is directed towards the provision of a synthetic PRP-peptide conjugate that can be used in a diagnostic immunoassay to detect the presence of anti-Hib antibodies, for example, anti-PRP and anti-OMP antibodies.

A yet further apsect of the present invention is directed towards the provision of a mixture of PRP-specific and OMP-specific antibodies as a component in a diagnostic immunoassay kit to detect the presence of typeable or non-typeable Hi strains in biological specimens.

SUMMARY OF INVENTION

The present invention relates to the provision of immunogens and candidate vaccines made of peptides containing the amino acid sequences of various antigenic determinants (T-helper cell and B-cell epitopes) of the outer membrane proteins (P1, P2 and P6) of Hib. Synthetic vaccines comprising one or more of these peptides that can be administrated either as free peptides, or covalently coupled to synthetic PRP oligomers as synthetic glycoconjugate vaccines and/or linked to a lipidic moiety to enhance their immunogenicity, are disclosed.

In one aspect of the present invention, there is provided a synthetic peptide having an amino acid sequence corresponding to at least one antigenic determinant of at least one protein of *Haemophilus influenzae*, preferably an outer membrane protein of *Haemophilus influenzae* type b.

In one embodiment, the present invention comprises an essentially pure form of peptide containing at least one amino acid sequence corresponding to a conserved antigenic determinant of the Hi P1 protein, which peptide is capable of eliciting polyclonal antibodies in mammals that can recognize Hi in vitro. These P1-specific polyclonal antibodies can be used as a component of test kits for detecting the presence of Hi in a biological sample. The peptides can have, for example, the amino acid sequences corresponding to amino acids 1 to 29, 39 to 64, 103 to 137, 165 to 193, 189 to 218, 226 to 253, 248 to 283, 307 to 331, 400 to 437 and 179 to 218 of the mature P1 protein of Hib MinnA strain, respectively, as set forth in Table 1 below (SEQ ID NOS: 1, 12, 3, 4, 5, 6, 7, 9, 13 or 14 and 15 respectively) or any portion or variant thereof which retains immunogenicity.

In another embodiment, the present invention comprises an essentially pure form of peptide containing at least one amino acid sequence corresponding to a conserved antigenic determinant of the P2 protein, which peptide is capable of eliciting polyclonal antibodies in mammals that can recognize Hi in vitro. These P2-specific polyclonal antibodies can be used as a component of test kits for detecting the presence of Hi in biological samples. The peptides can have, for example, the amino acid sequences corresponding to amino acids 1 to 14, 125 to 150, 241 to 265, 263 to 289, 285 to 306, 302 to 319, and 314 to 341 of the mature P2 protein of the Hib MinnA strain, respectively, as set forth in Table 2 below (SEQ ID NOS: 16, 23, 28, 29, 30, 31 and 32 respectively) or any portion or variant thereof which retains immunogenicity.

In another embodiment, the present invention comprises an essentially pure form of peptide containing at least one amino acid sequence corresponding to an antigenic determinant of the P6 protein, which peptide is capable of eliciting polyclonal antibodies against Hi in mammals. These P6-specific polyclonal antibodies should be useful in test kits for detecting the presence of Hi in any biological sample. The peptides can have, for example, the amino acid sequences corresponding to amino acids 1 to 22, 19 to 41, 35 to 58, 54 to 77, 73 to 96, 90 to 114 and 109 to 134 of the mature P6 protein of the Hib MinnA strain, respectively, as set forth in Table 3 below (SEQ ID NOS: 35 to 41 respectively) or any portion or variant thereof which retains immunogenicity.

In another embodiment, the present invention comprises at least one P1 peptide that contains at least one amino acid sequence corresponding to an immunodominant linear B-cell epitope of the P1 protein. These epitopes can be used as target antigens in diagnostic kits to detect the presence of anti-Hi antibodies for example, protective antibodies. The peptides can have, for example, the amino acid sequence corresponding to amino acids 39 to 64, 103 to 137, 165 to 193, 248 to 283, 307 to 331, 400 to 437 and 179 to 218 of the mature P1 protein of the Hib MinnA strain, respectively, as set forth in Table 1 below (SEQ ID NOS: 12, 3, 4, 7, 9, 13 or 14 and 15 respectively) or any portion or variant thereof which retains immunogenicity.

In another embodiment, the present invention comprises at least one P2 peptide that contains at least one amino acid sequence corresponding to an immunodominant linear B-cell epitope of P2. These epitopes can be used as target antigens in diagnostic kits to detect the presence of anti-Hi antibodies for example, protective antibodies. The peptides can have, for example, the amino acid sequences corresponding to amino acids 53 to 81, 148 to 174, 241 to 265 and 314 to 342 of the mature P2 protein of the Hib MinnA strain, respectively, as set forth in Table 2 below (SEQ ID NOS: 20, 24, 28 and 32 respectively) or any portion or variant thereof which retains immunogenicity.

In another embodiment, the present invention comprises at least one P6 peptide that contain at least one amino acid sequence corresponding to an immunodominant linear B-cell epitope of P6. These epitopes can be used as target antigens in diagnostic kits to detect the presence of anti-Hi antibodies for example, protective antibodies. The peptides can have, for example, the amino acid sequences corresponding to amino acids 73 to 96, 90 to 114 and 109 to 134 of the mature P6 protein of the Hib MinnA strain, respectively, as set forth in Table 3 below (SEQ ID NOS: 39, 40 and 41 respectively), or any portion or variant thereof which retains immunogenicity.

In another embodiment, the present invention comprises peptides that have been identified as immunodominant T-cell epitopes of P1. These peptides can be used as autologous carriers for PRP, or as carriers for autologous and heterologous B-cell epitopes. The peptides can have, for example, the amino acid sequence corresponding to amino acids 39 to 64, 226 to 253, 339 to 370 and 400 to 437 of the mature P1 protein of the Hib MinnA strain, respectively, as set forth in Table 1 below (SEQ ID NOS: 12, 6, 10 and 13 or 14 respectively), or any portion or variant thereof which retains immunogenicity.

In another embodiment, the present invention comprises peptides that have been identified as immunodominant T-cell epitopes of P2. These peptides can be used as autologous carriers for PRP, or as carriers for autologous and heterologous B-cell epitopes. The peptides can have, for example, the amino acid sequences corresponding to amino acids 125 to 150, 193 to 219, 219 to 244 and 241 to 265 of the mature P2 protein of the Hib MinnA strain, respectively, as set forth in Table 2 below (SEQ ID NOS: 23, 26, 27 and 28 respectively), or any portion or variant thereof which retains immunogenicity.

In another embodiment, the present invention comprises peptides that have been identified as immunodominant T-cell epitopes of P6. These peptides can be used as autologous carriers for PRP, or as carriers for autologous and heterologous B-cell epitopes. The peptides can have, for example, the amino acid sequences corresponding to amino acids 19 to 41, 35 to 58, 73 to 96 and 109 to 134 of the mature P6 protein of the Hib MinnA strain, respectively, as set forth in Table 3 below (SEQ ID NOS: 36, 37, 39 and 41 respectively), or any portion or variant thereof which retains immunogenicity.

In another aspect, therefore, the present invention provides an immunogenic conjugate, comprising a synthetic peptide having an amino acid sequence corresponding to at least one immunodominant T-cell epitope of at least one protein of *Haemophilus influenzae* linked to at least one synthetic B-cell epitope.

In another aspect of the present invention, there is provided a highly efficient chemical synthesis process to prepare synthetic PRP oligomers. This process was a combination of solid/liquid-phase synthesis using polyethylene glycol monomethyl ether (PEG) as solid support. The solid-phase support contains high number of chemically reactive functional groups ranging from about 200 to 500 μmol/g of support, as compared to the about 30 to 35 μmoles of reactive groups per g of conventional supports, such as controlled pore glass. Only stoichiometric amounts of synthetic PRP repeating unit in each coupling cycle, as compared to a 5 to 10 fold molar excess in the conventional solid-phase synthesis. In addition, the present novel process is fast, cost-effective and simple to scale-up for commercial applications, in contrast to solution-phase synthesis which is laborious, expensive and time-consuming.

The product of this process aspect of the invention comprises a chemically reactive synthetic PRP oligosaccharide represented by the following formula:

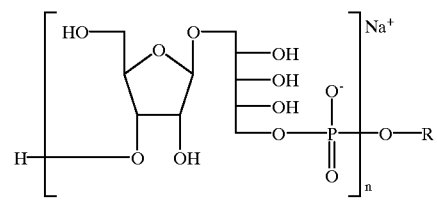

where n is an integer, preferably from 3 to 20, and R is a linker fragment defined by —CH$_2$—(CH$_2$)$_m$—X, wherein m is an integer, preferably from 3 to 5, inclusive, and X is a chemically reactive functional group, such as —CH$_2$NH$_2$, —CH$_2$SH, or an amino-reactive group, such as an halogen, methanesulfonyl, trifluoromethanesulfonyl, or toluenesulfonyl, and the like, or a photoactivatable group, such as phenyl azide, nitrophenyl, benzylphenyl, and the like. The reactive functional group permits the synthetic PRP to be linked to other molecules.

In a further aspect of the invention, there is provided an immunogenic conjugate, comprising a synthetic carbohydrate antigen linked to at least one synthetic T-cell epitope. The carbohydrate antigen may be derived from bacterial material, particularly a synthetic riboseribitol phosphate (PRP) oligomer.

In yet another embodiment, the present invention provides an immunogenic synthetic PRP-peptide conjugate vaccine, that is capable of inducing high titer of anti-PRP antibodies in mammals. The synthetic PRP-carrier conjugate vaccine contains a molecule of the formula:

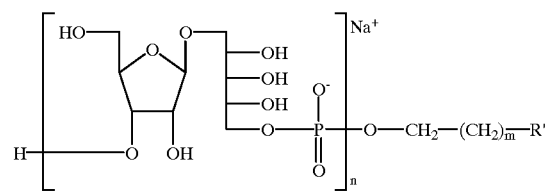

wherein n and m are as defined above and R' is a synthetic peptide containing at least one T-helper cell epitope, for example, a human T-cell epitope containing the amino acid sequence GPKEPFRDYVDRFYK (SEQ ID NO: 50) from the HIV-1 gag protein p24, or a T-cell epitope from Hi OMP. The carrier may be a peptide containing both a T-helper and B-cell epitopes.

In another embodiment, the present invention comprises an immunogenic synthetic glycoconjugate of a synthetic PRP oligomer of defined length and the Hib P1 peptide containing T- and/or T-B epitopes. The size of the synthetic PRP oligomer is at least three repeating units of PRP, but preferably six PRP repeating units. The peptides can have, for example, the amino acid sequences corresponding to amino acids 39 to 64, 165 to 193, 189 to 218, 226 to 253, 339 to 370 and 400 to 437 of the P1 protein of the Hib MinnA strain, respectively, as set forth in Table 1 below (SEQ ID NOS: 12, 4, 5, 6, 10 and 13 or 14 respectively), or any portion or variant thereof which retains immunogenicity.

In another embodiment, the present invention comprises an immunogenic synthetic glycoconjugate of a synthetic PRP oligomer of defined length and a P2 peptide containing T- and/or T-B epitopes. The size of the synthetic PRP oligomer is at least three repeating units of PRP, but preferably six PRP repeating units. The peptides can have, for example, the amino acid sequences corresponding to amino acids 125 to 150, 193 to 219, 219 to 244 and 241 to 265 of the mature P2 protein of the Hib MinnA strain, respectively, as set forth in Table 2 below (SEQ ID NOS: 23, 26, 27 and 28 respectively), or any portion or variant thereof which retains immunogenicity.

In another embodiment, the present invention comprises an immunogenic synthetic glycoconjugate of a synthetic PRP oligomer of defined length and a P6 peptide containing T- and/or T-B epitopes. The size of the synthetic PRP oligomer is at least three repeating units of PRP, but preferably six PRP repeating units. The peptides can have, for example, the amino acid sequences corresponding to amino acids 19 to 41, 35 to 58, 73 to 96 and 109 to 134 of the mature P6 protein of the Hib MinnA strain, respectively, as set forth in Table 3 (SEQ ID NOS: 36, 37, 39 and 41), or any portion or variant thereof which retains immunogenicity.

In another embodiment, the present invention provides the concept that the immunogenicity of a carbohydrate antigen, for example synthetic PRP, can be enhanced using a multiple antigen peptide system (MAPs) containing functional T-helper cell epitopes as carrier to increase the carbohydrate density within the synthetic glycopeptide conjugate. The MAPs can contain, for example (FIG. 1), the sequence DIVAKIAYGRTNYKYNESDEHKQQLNG (SEQ ID NO: 26) corresponding to amino acid 193–219 of the P2 protein of the Hib MinnA strain, or any portion thereof.

In another embodiment, the present invention comprises a synthetic PRP-lipopeptide (or a mixture of synthetic PRP-lipopeptides) conjugate that is capable of inducing cell-mediated and humoral immune responses against Hi in mammals. The lipopeptide can have, for example, the sequence Tripalmityl-CSSYAKAQVERNAGLIADSVKDNQITSALSTQC (SEQ ID NO: 43), corresponding to amino acids 165 to 193 of the P1 protein of the Hib MinnA strain, or any portion thereof.

In another embodiment, the present invention comprises immunogenic chimeric peptide vaccines that consist of identified T-B epitopes of either Hib P1 or P2 or P6, and can be used to immunize mammals against Hi infection. The peptides can have, for example, the sequences VKTIGD-KRTLTLNTCARTRTTETGKGVKTEKEKS-VGVGLRVYF (SEQ ID NO: 42), VKTIGDKNTLTLNTF-GDGFYAQGYLETRFVTKASENGSNFGDC (SEQ ID NO: 43), VKTIGDKNTLTLNTCGANYLLAQKRE-GAKGENKRPNDKAGEV (SEQ ID NO: 44), VKTIGD-KRTLTLNTDIVAKIAYGRTNYKYNESDEHKQQLNGC (SEQ ID NO: 45), VKTIGDKRTLTLNTYAKT-KNYKIKHEKRYFVSPGFQYELC (SEQ ID NO: 46), GYLETRFVTKASENGSDFKEVKTIGD-KRTLTLNTTANYTSQAHANLYGLNLNYSF (SEQ ID NO: 47), AKGENKRPNDKAGEVFKEVKTIGD-KRTLTLNTTANYTSQAHANLYGLNLNYSF (SEQ ID NO: 48) and ARTRTTETGKGVKTEKFKEVKTIGD-KRTLTLNTTANYTSQAHANLYGLNLNYSF (SEQ ID NO: 49) or any portion or variant thereof which retains immunogenicity. Peptides of the invention can also have sequence corresponding to the analogous regions of Hi isolates other than MinnA.

The novel synthetic peptides and conjugates provided herein may be formulated into a vaccine against disease caused by a pathogen, particularly *Haemoohilus influenzae*, comprising at least one synthetic peptide and/or at least one synthetic conjugate, as described herein, and a physiological carrier therefor. The vaccine may be used for immunizing a host against the pathogenic disease by administering to a host an effective amount of the vaccine.

The vaccine may further comprise at least one other immunogenic and/or immunostimulating molecule. The invention also includes a method of immunizing a host against Hi infection, by administering to the host an effective amount of the vaccine.

Peptides described in the invention can be further either modified with lipids as lipopeptides or linked to synthetic PRP (and/or polymerized) as synthetic lipoglycopeptide conjugates to produce alternate vaccines.

The vaccines can be used to immunize against Hi infection when administered to mammals, for example, by the intramuscular or parenteral route, or when delivered to the mucosal surface using microparticles, capsules, liposomes and targeting molecules, such as toxins and antibodies.

The present invention further includes a live vector for antigen delivery containing a gene coding for an amino acid sequence of any of the synthetic peptides provided herein. The live vector may be a viral vector, such as poxviral, adenoviral, polioviral and retroviral viral vector. The live vector may be a bacterial vector, such as salmonella and mycobacteria. The live vector may be incorporated into a vaccine comprising the same and a physiologically-acceptable carrier.

As noted earlier, the synthetic peptides provided herein may be used as diagnostic reagents in a method of detecting infection by *Haemophilus influenzae*. Antibodies raised against any of the synthetic peptide and conjugates described herein are included in the present invention.

| Peptide | SEQ ID NO: |
| --- | --- |
| HIBP1-4 | 51 |
| CHIBP1-4 | 52 |
| COMP2-8 | 53 |
| MAP(COMP2-8) | 54 |
| CP6-6 | 55 |
| PZ4EC | 56 |

Figure 2A:
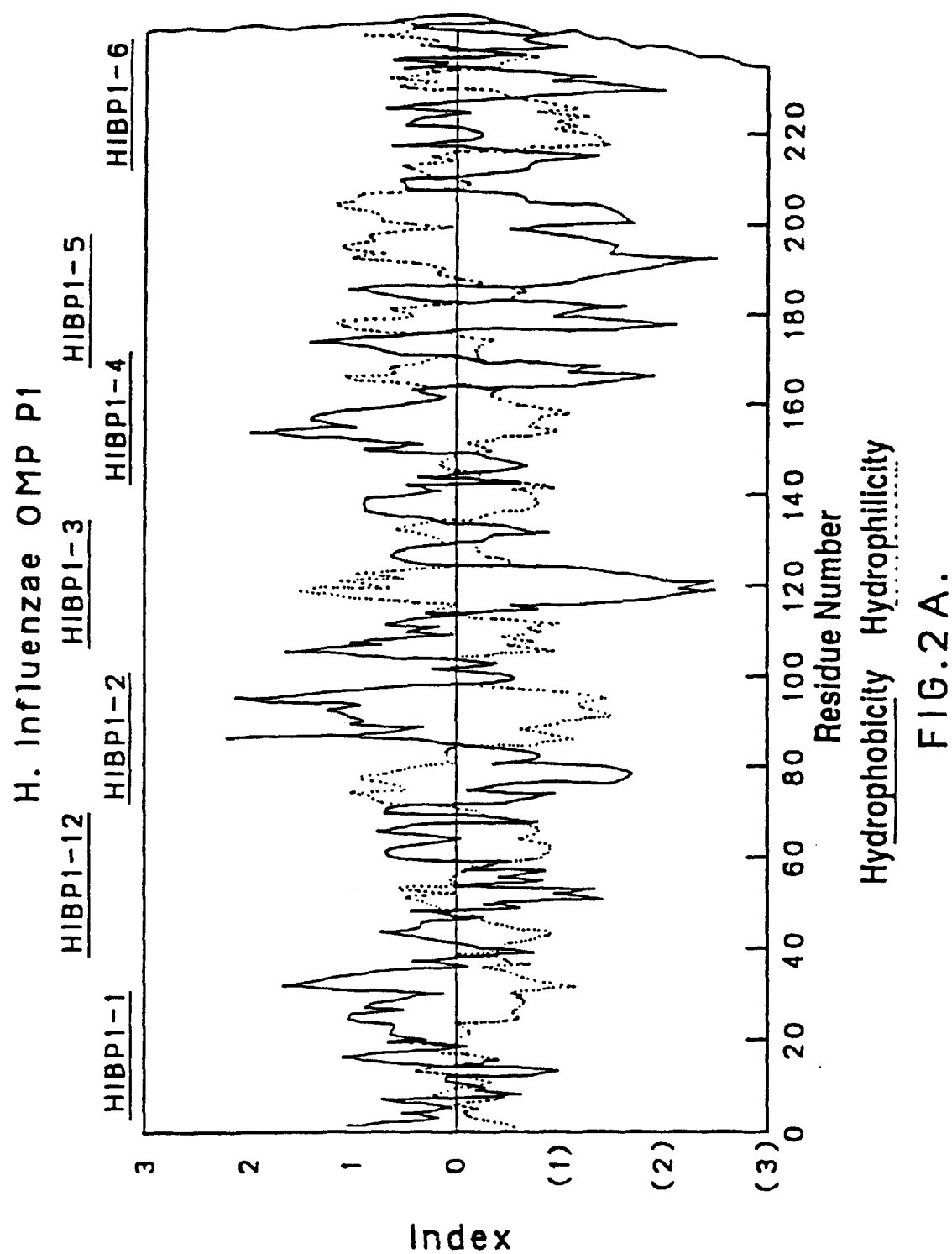
Figure 2B:
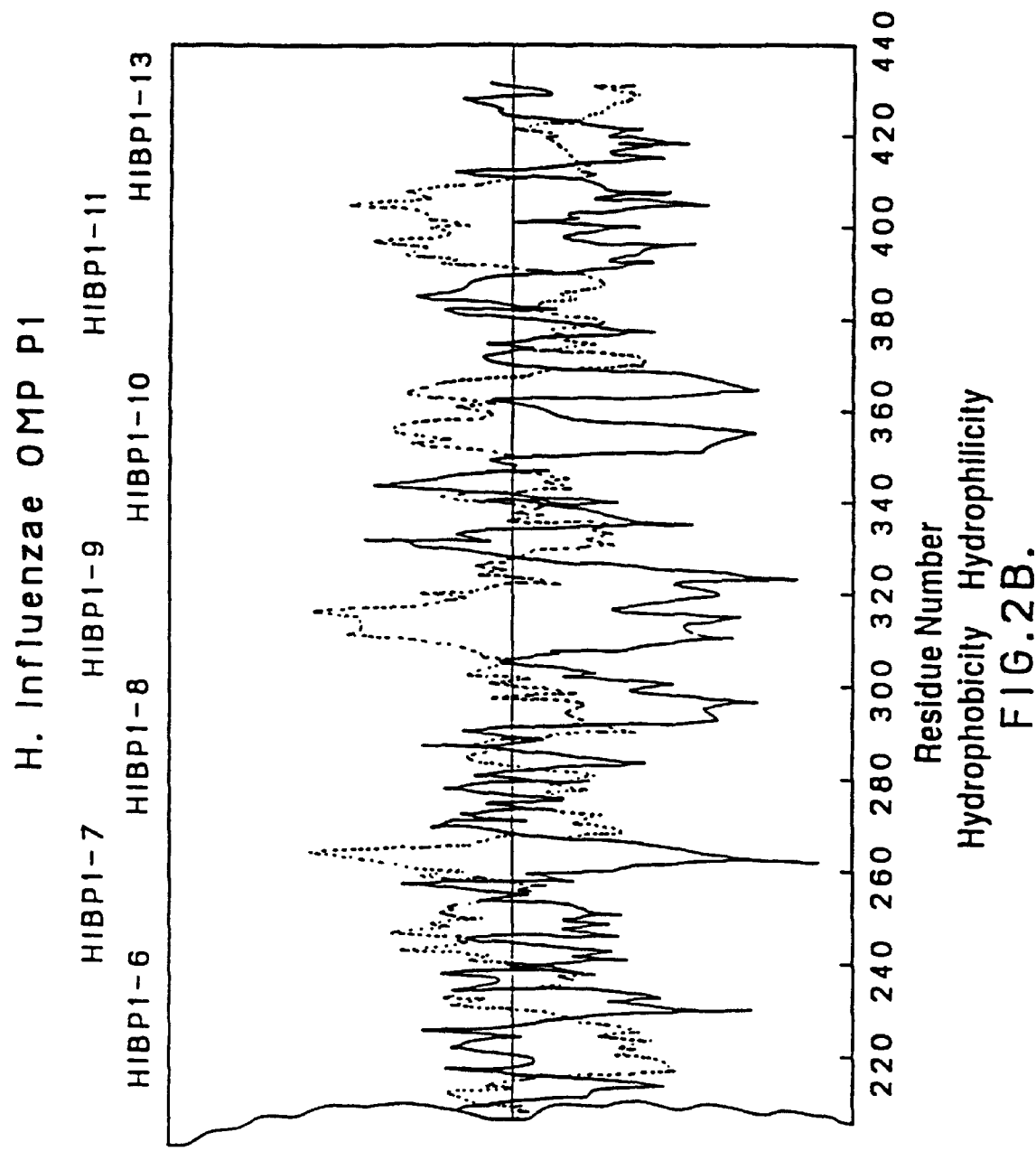
Figure 3A:
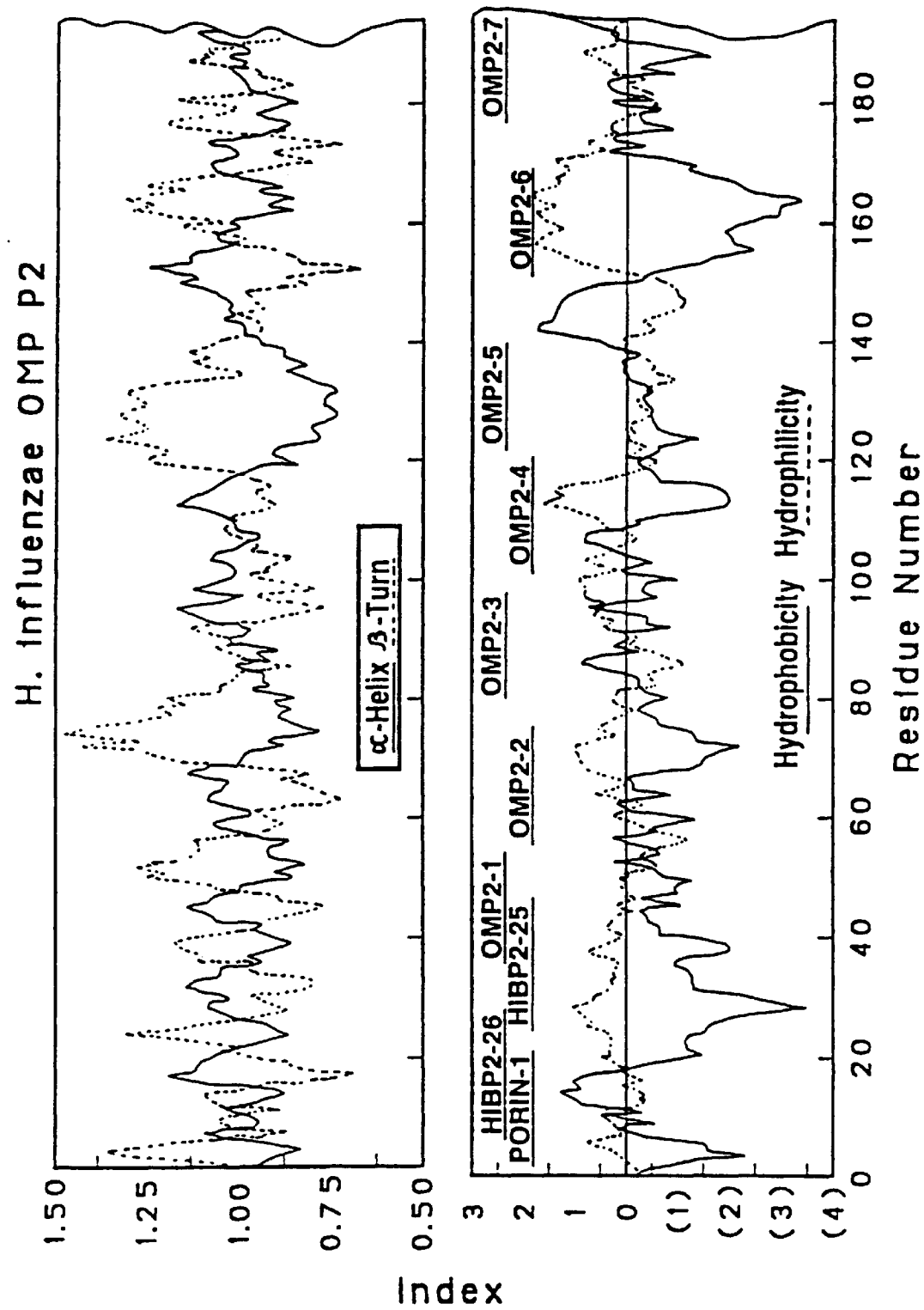
Figure 3B:
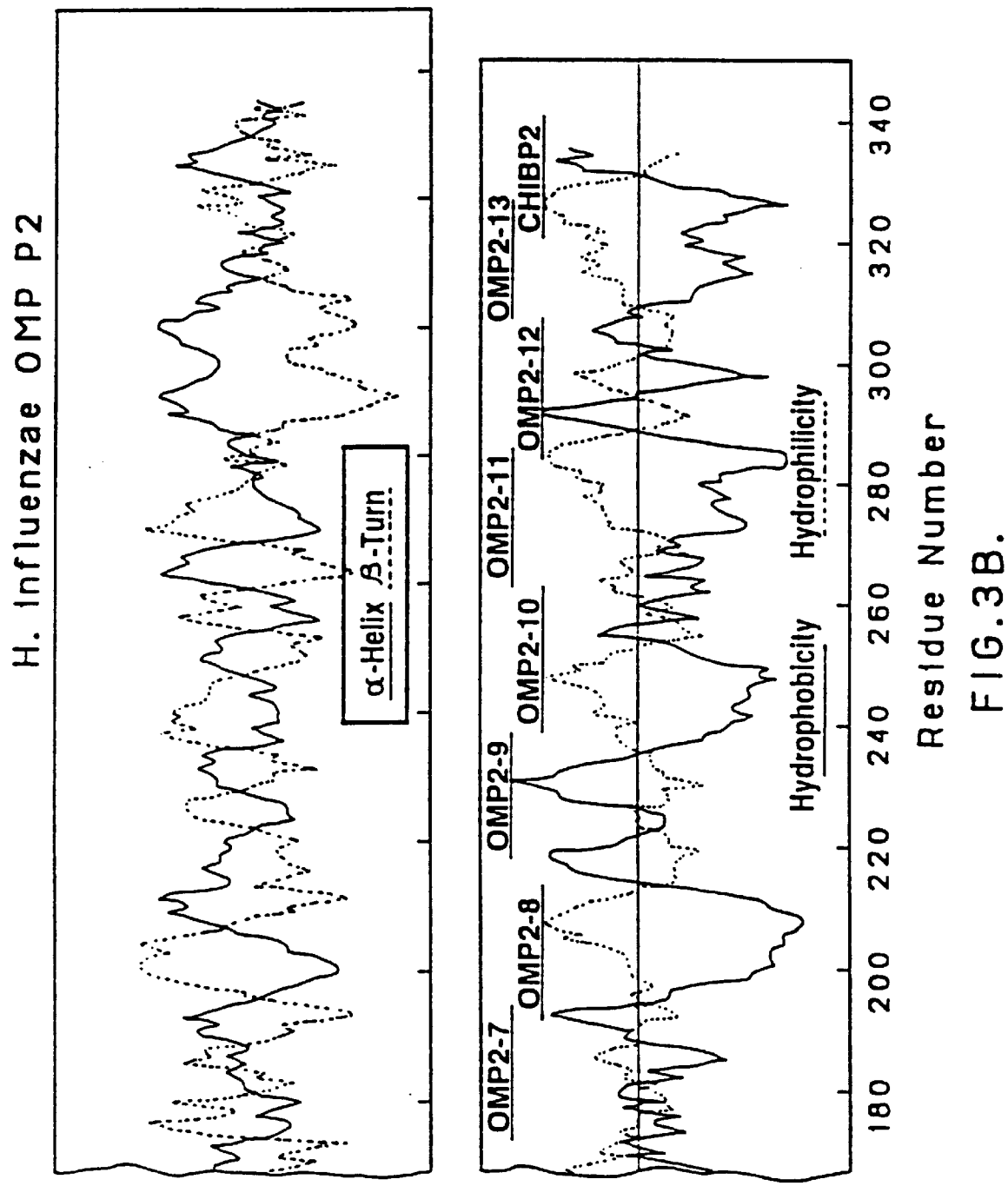
Figure 4:
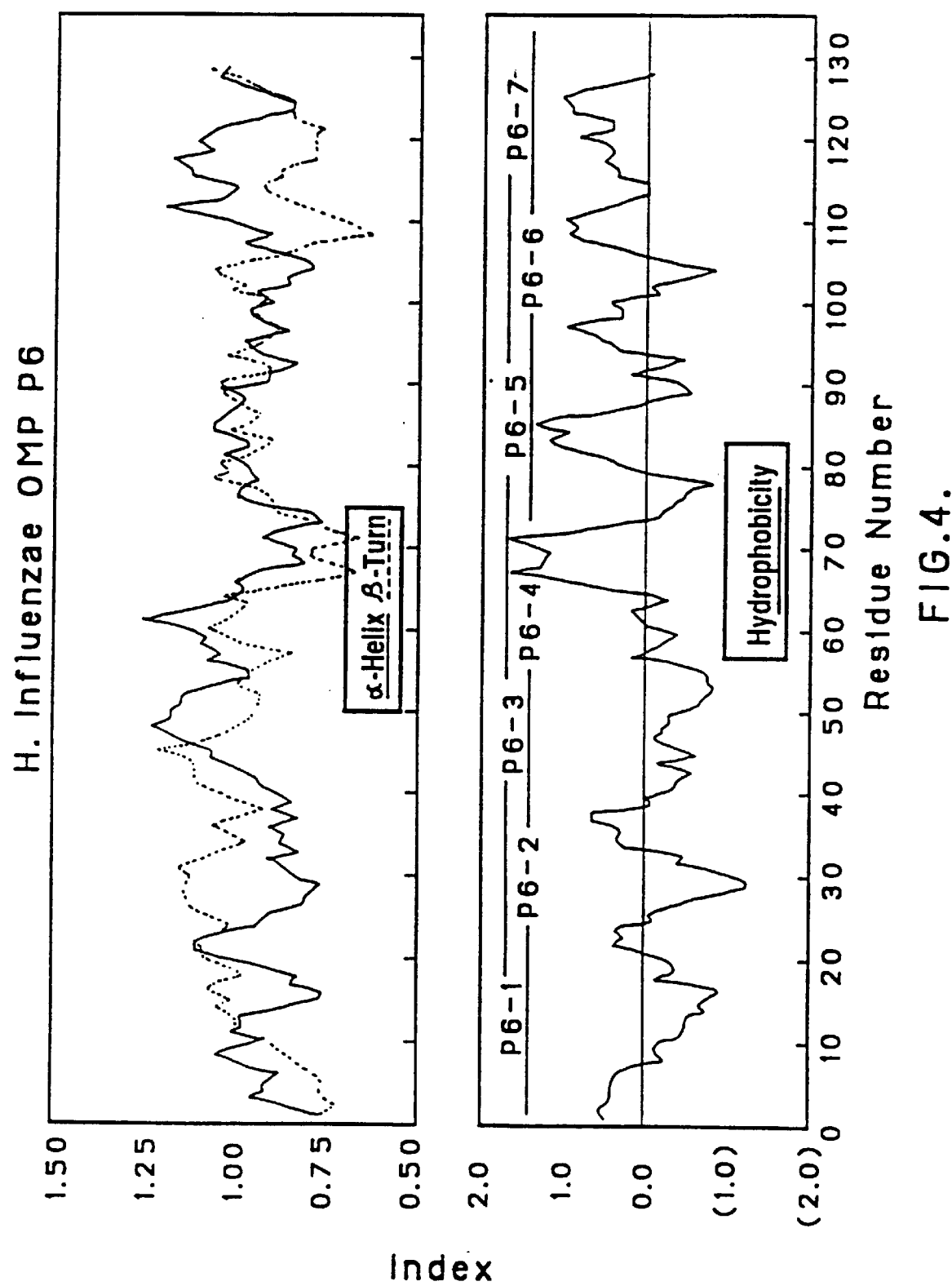
Figure 6:
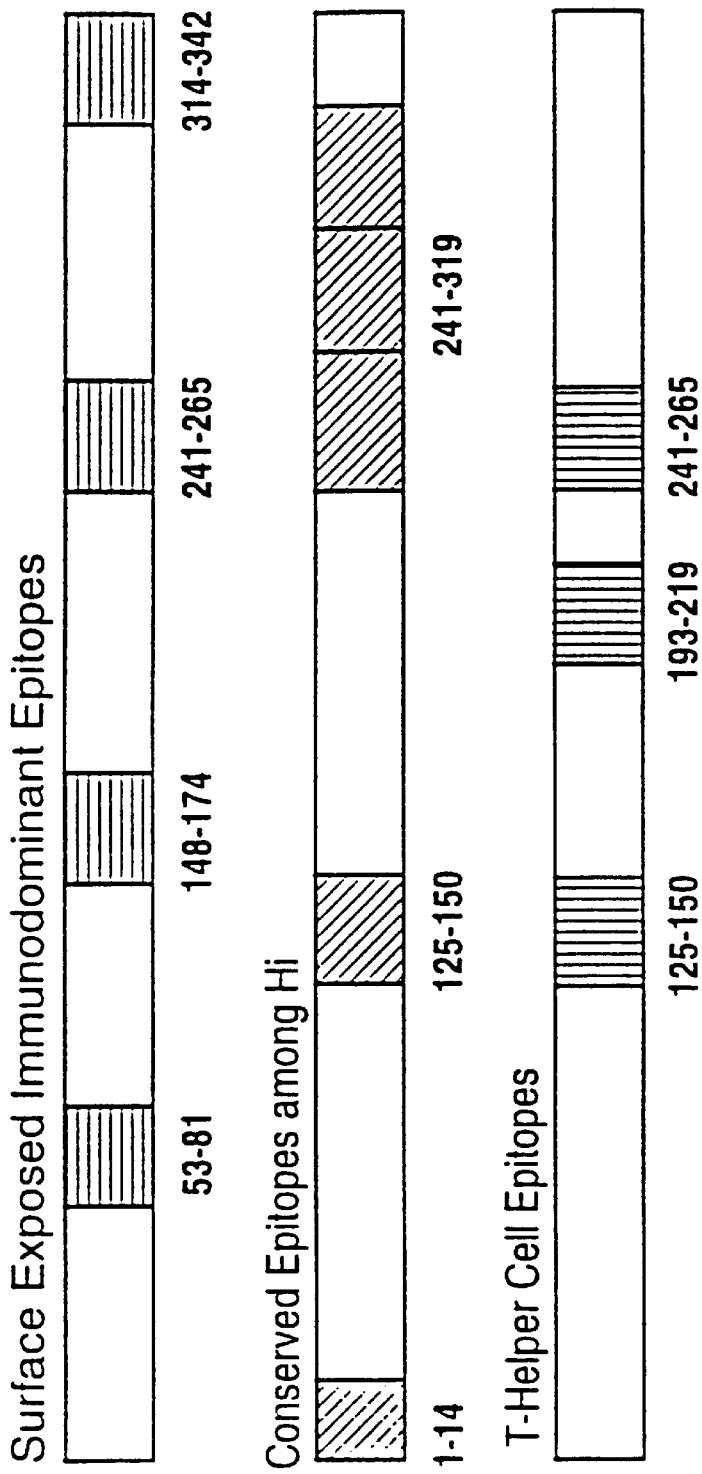
Figure 7:
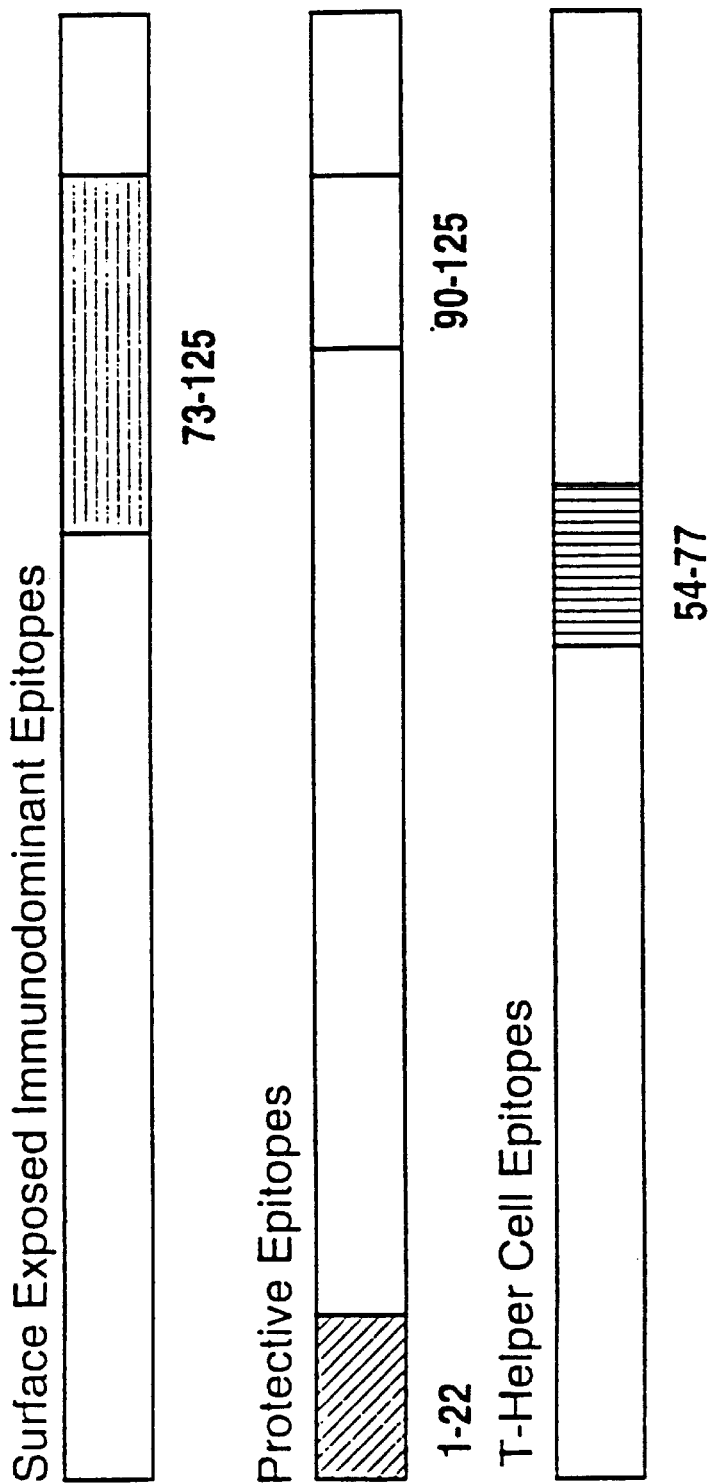
Figure 8A:
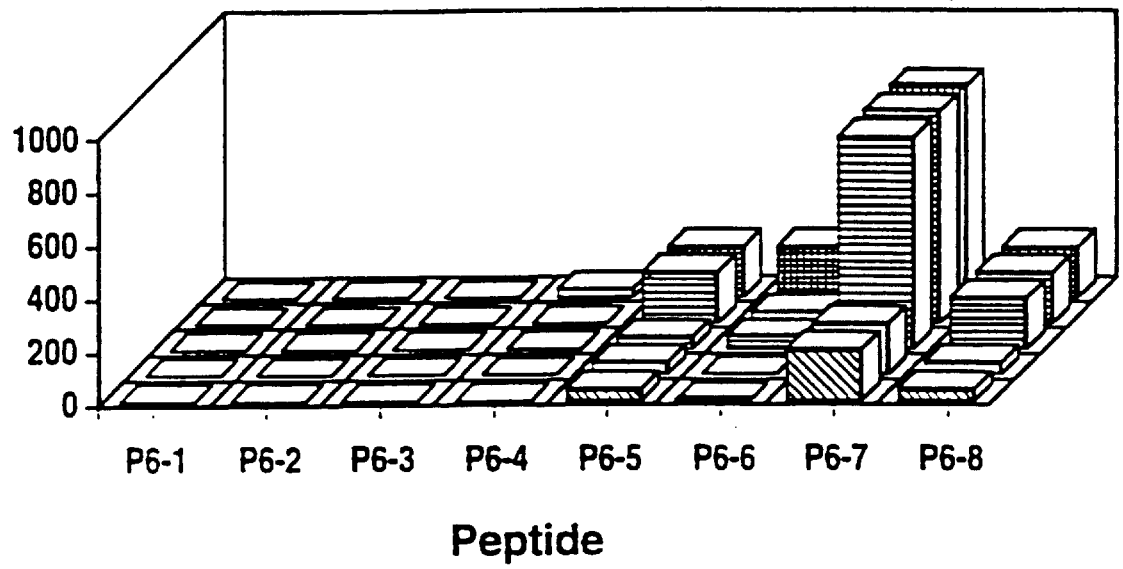
Figure 9:
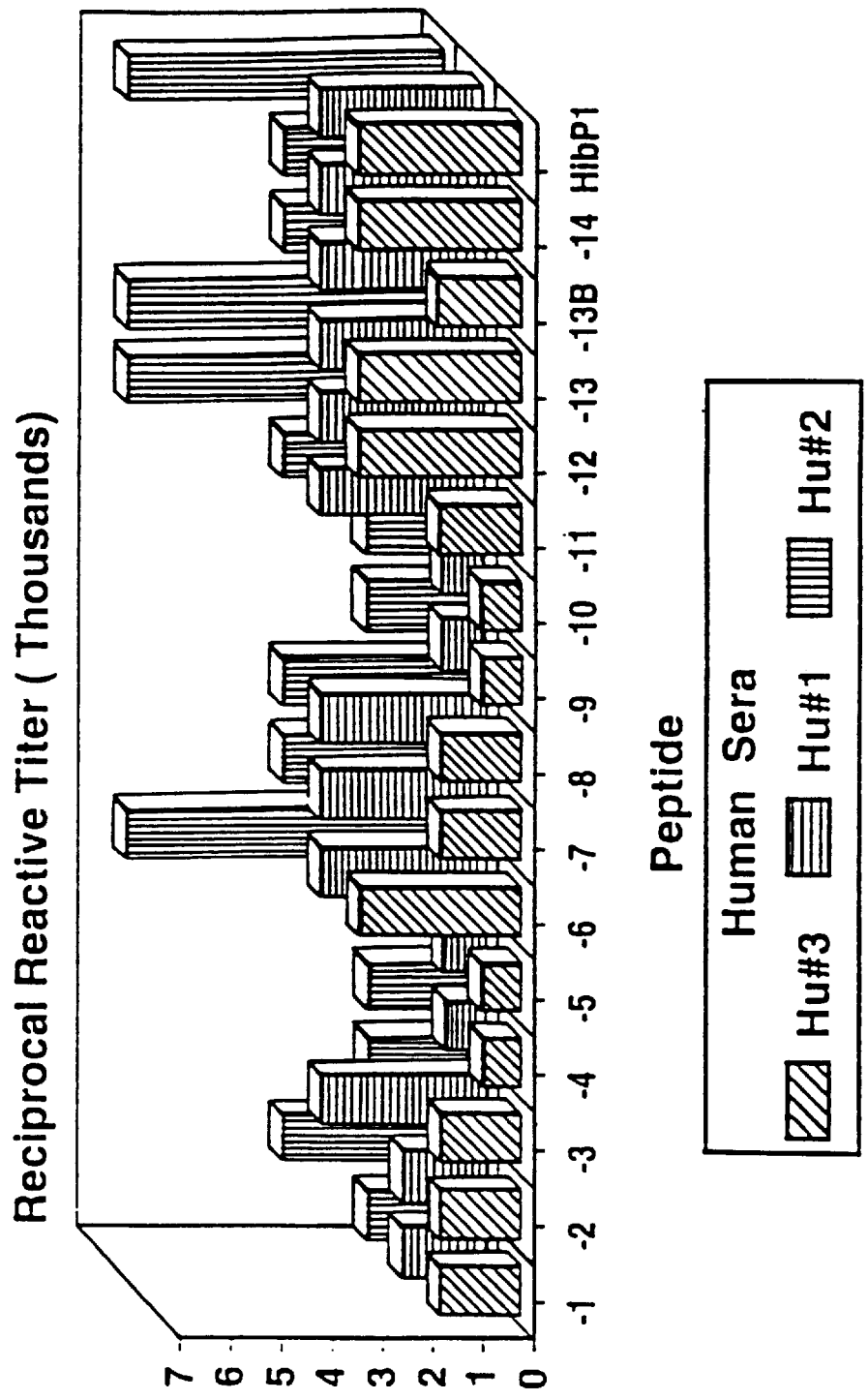
Figure 10:
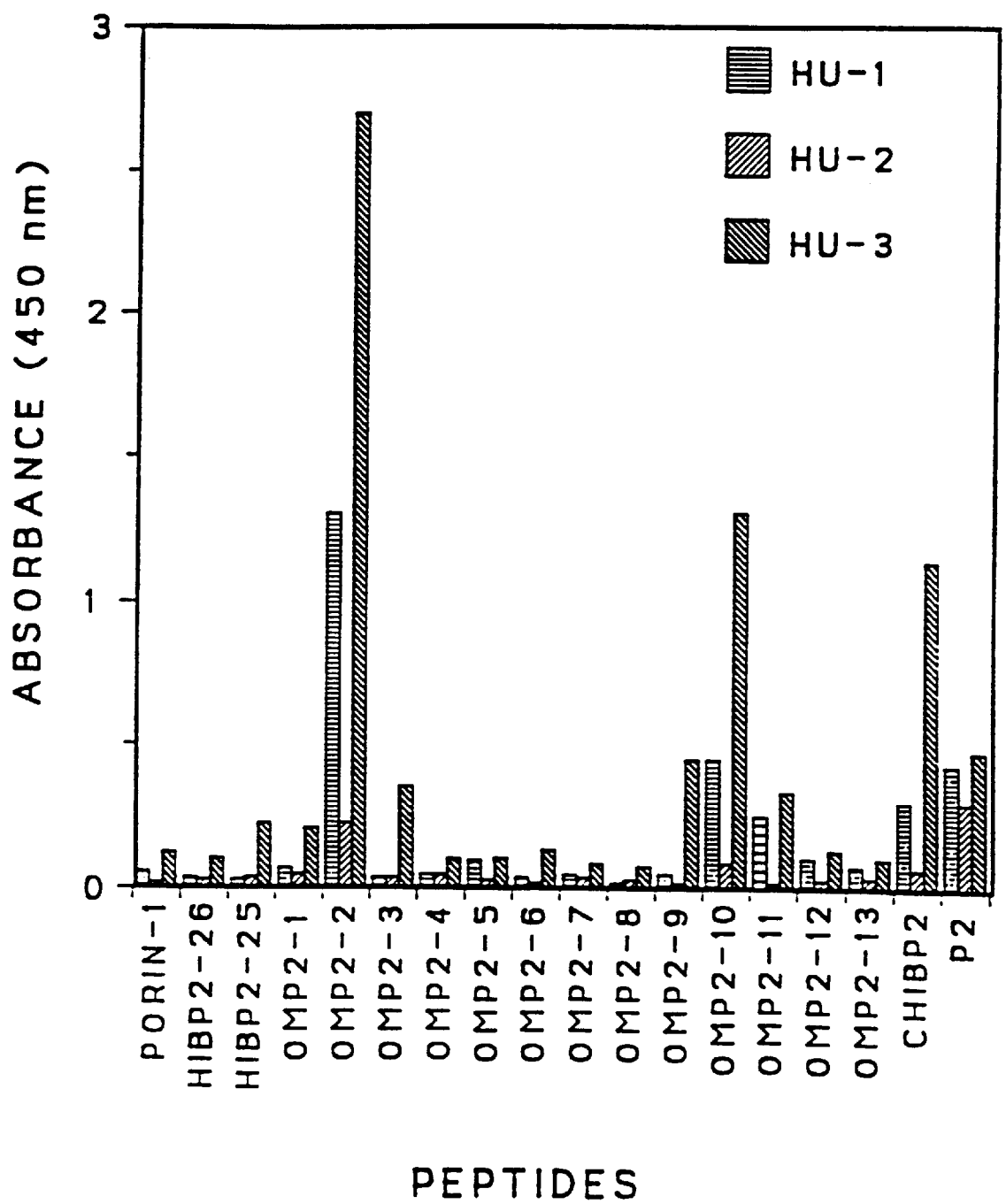
Figure 11A:
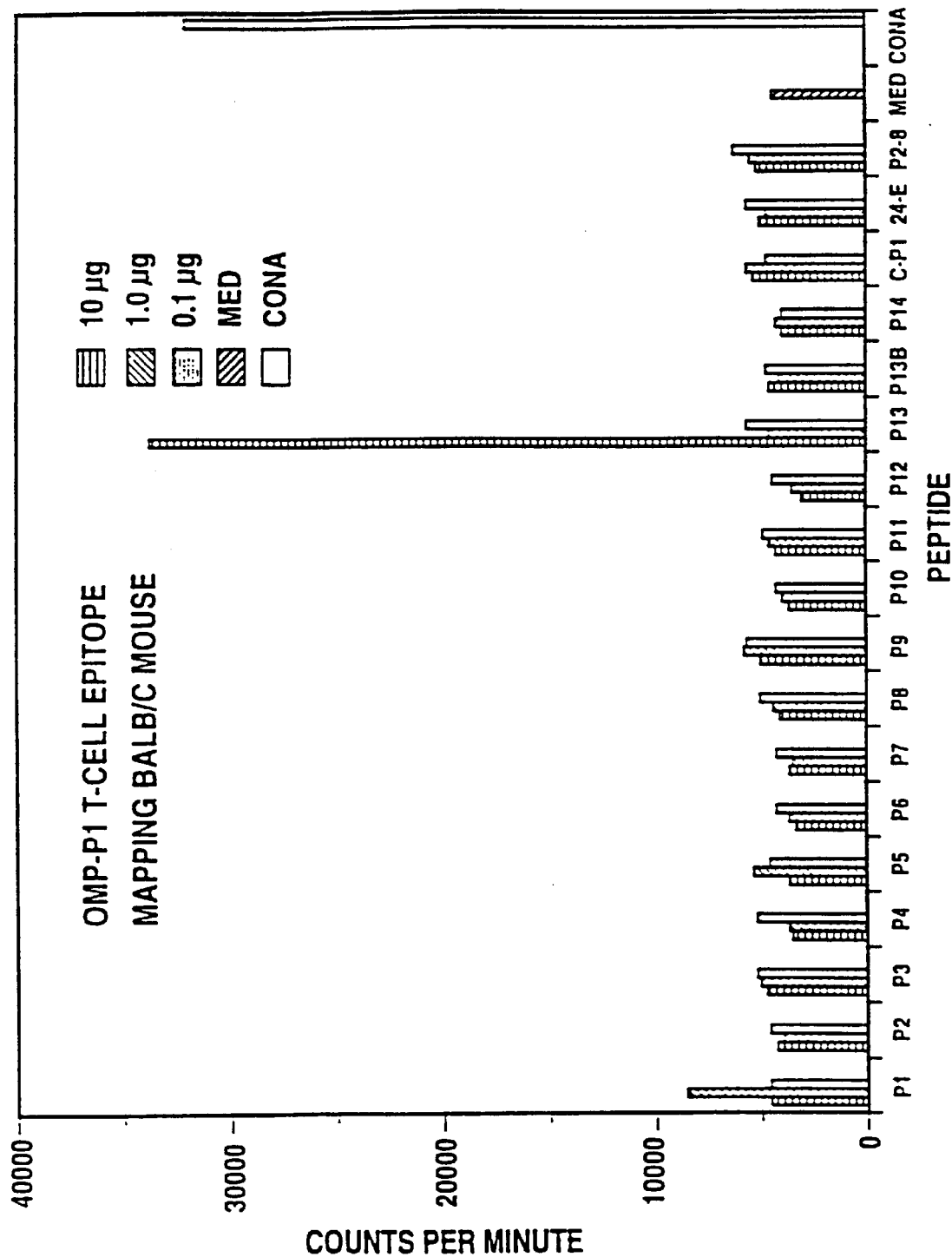
Figure 11B:
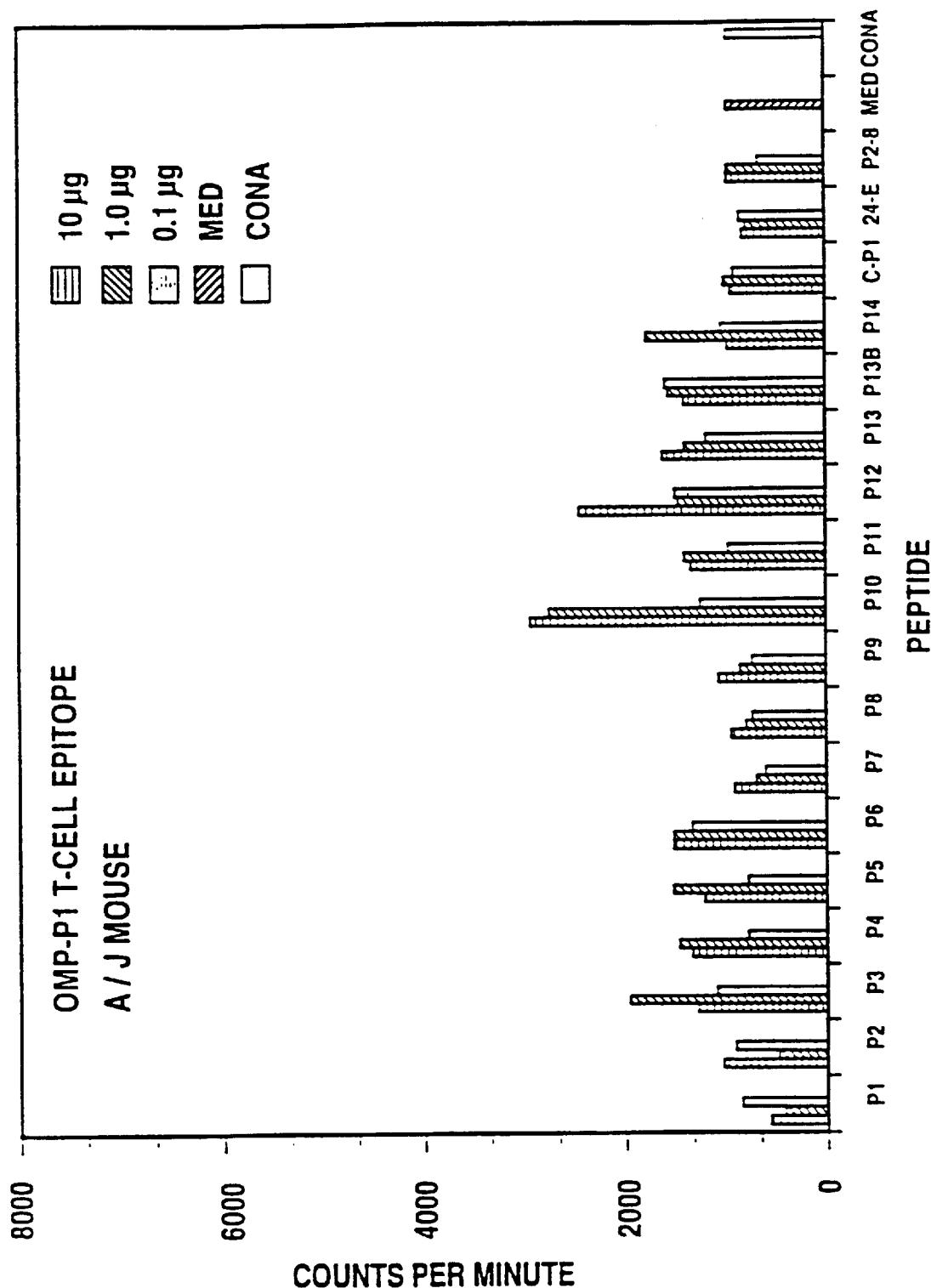
Figure 11C:
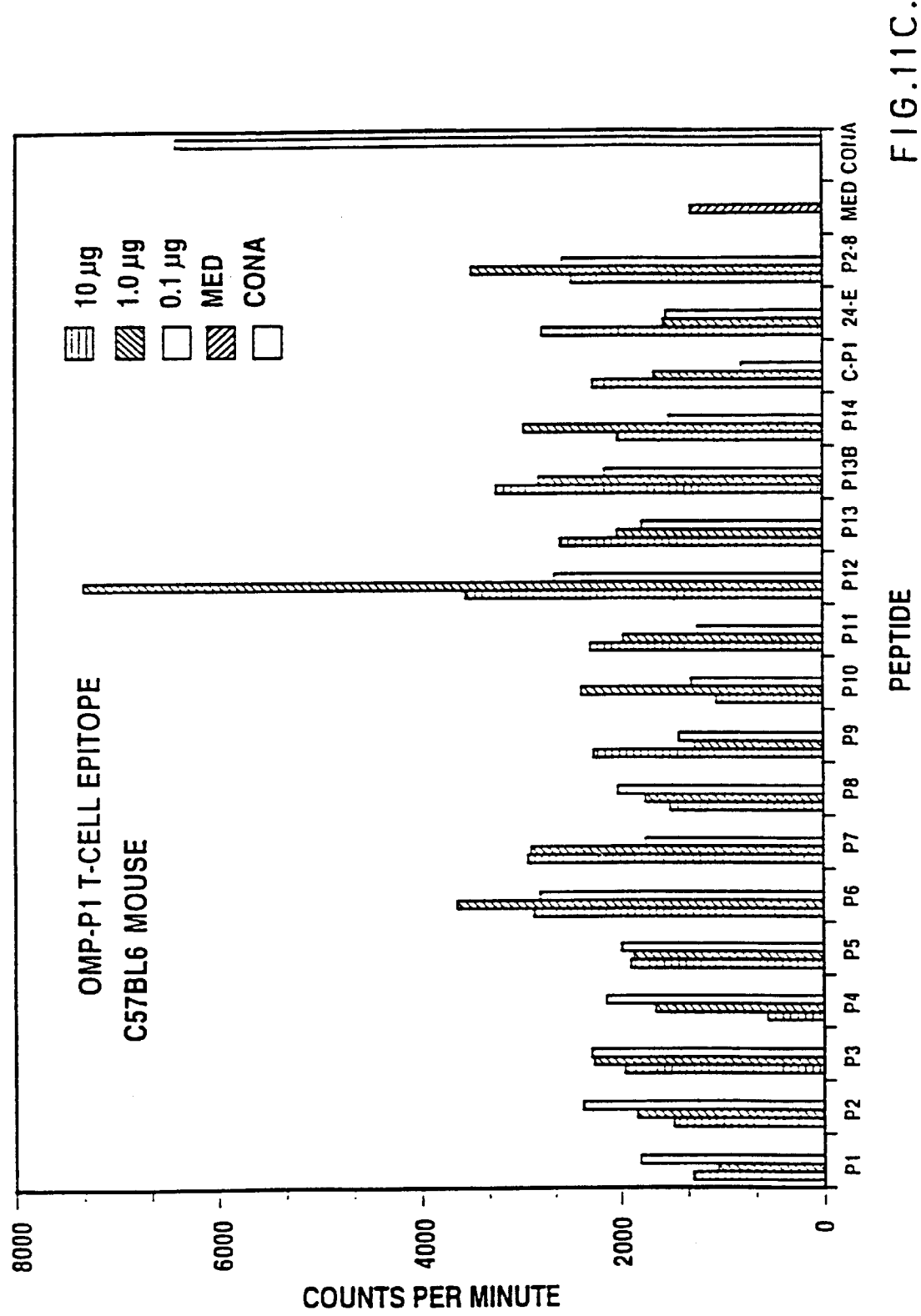
Figure 12A:
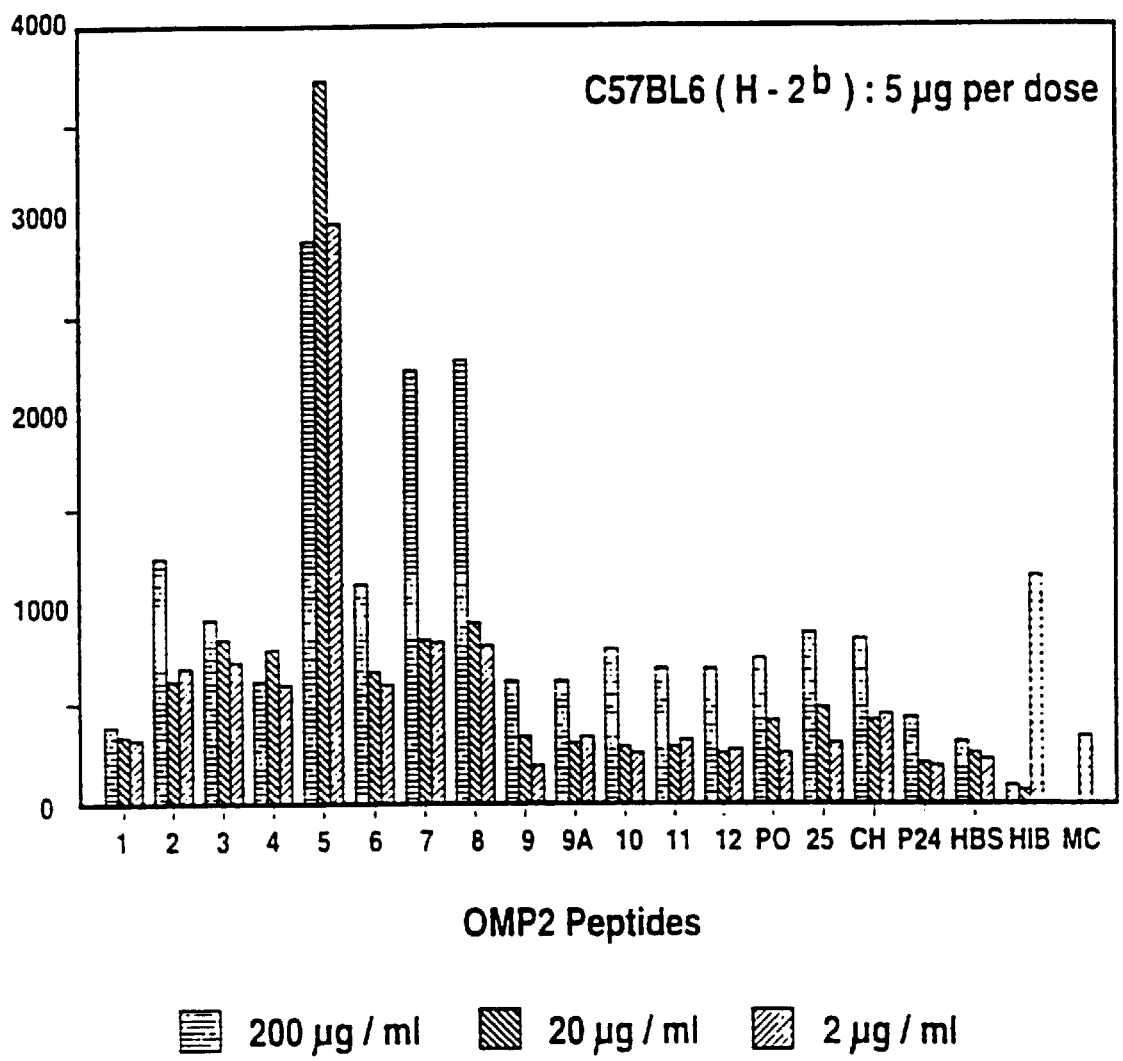
Figure 12B:
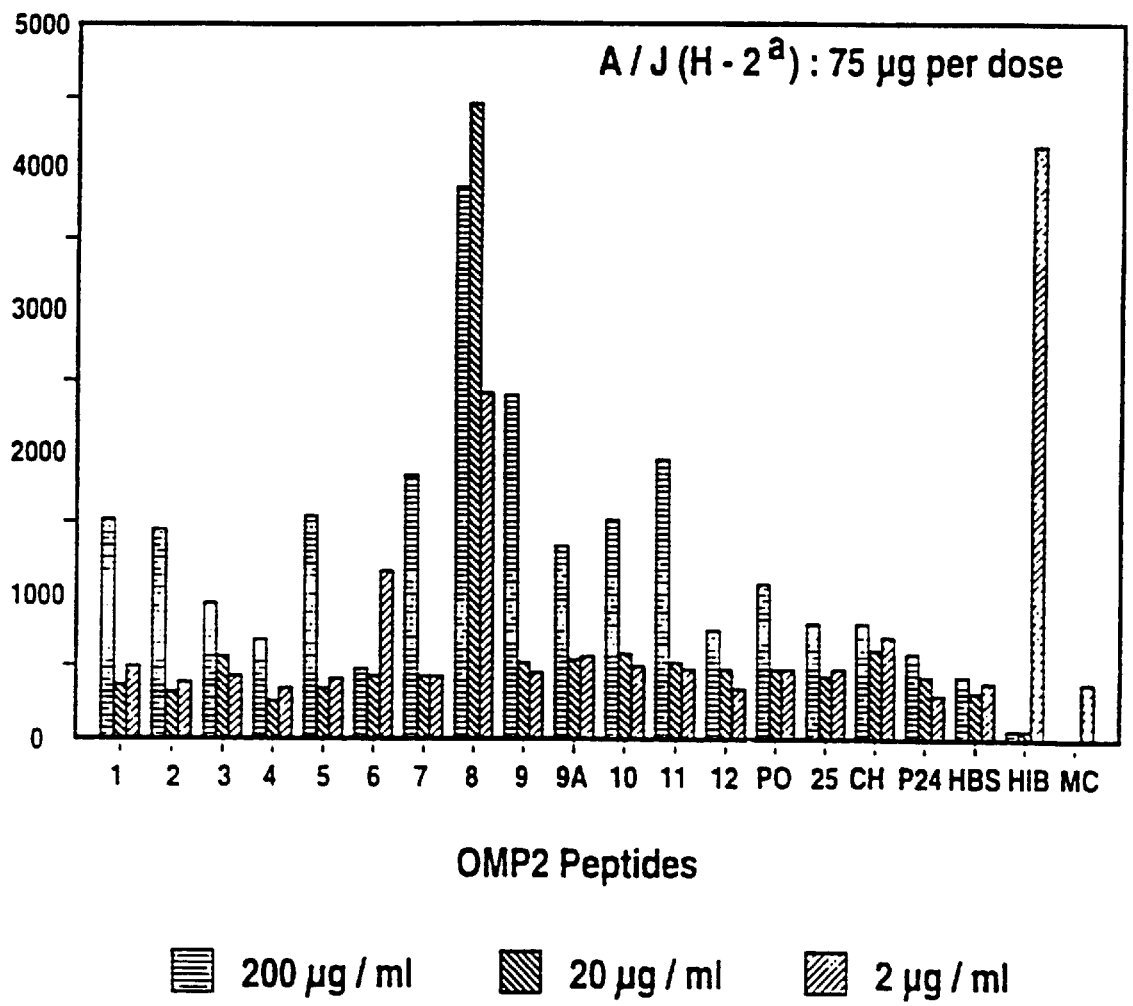
Figure 12C:
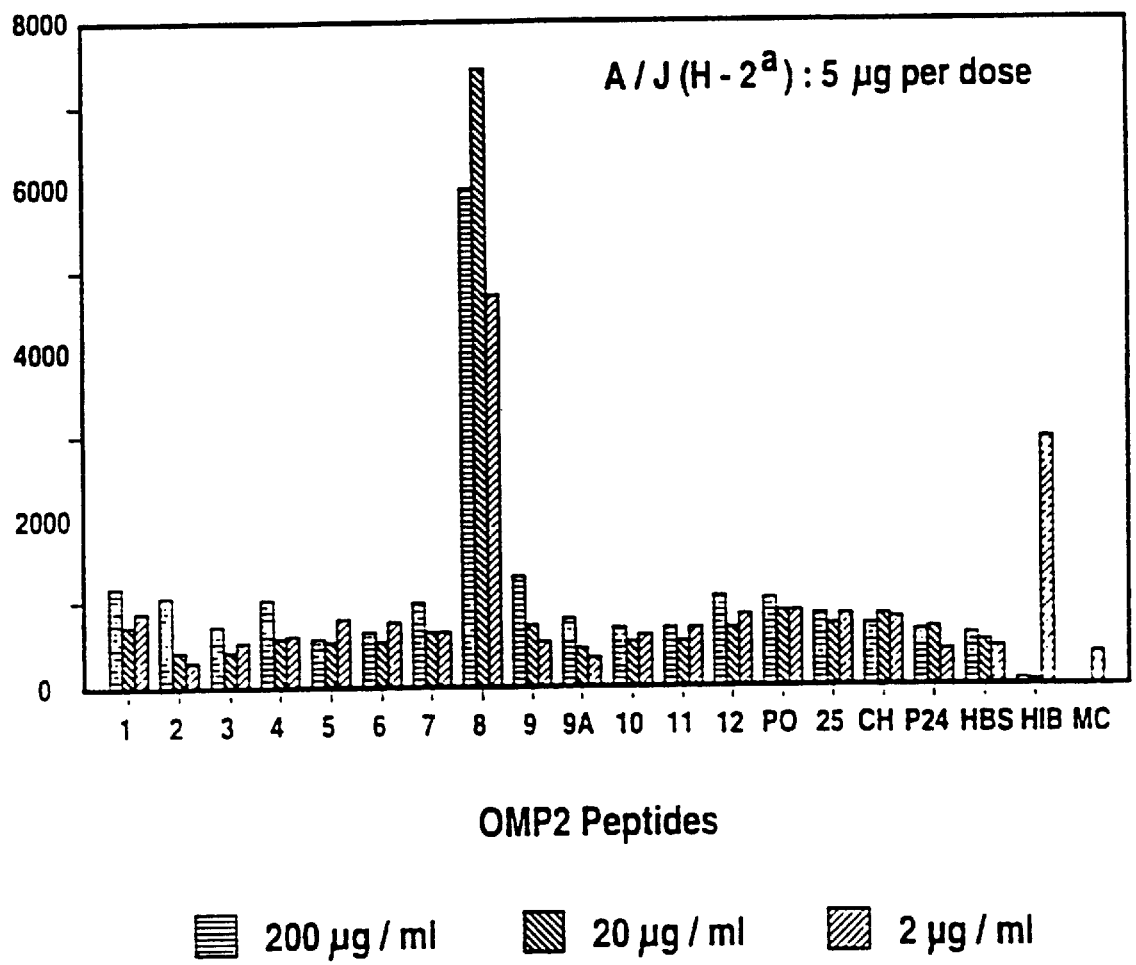
Figure 13A:
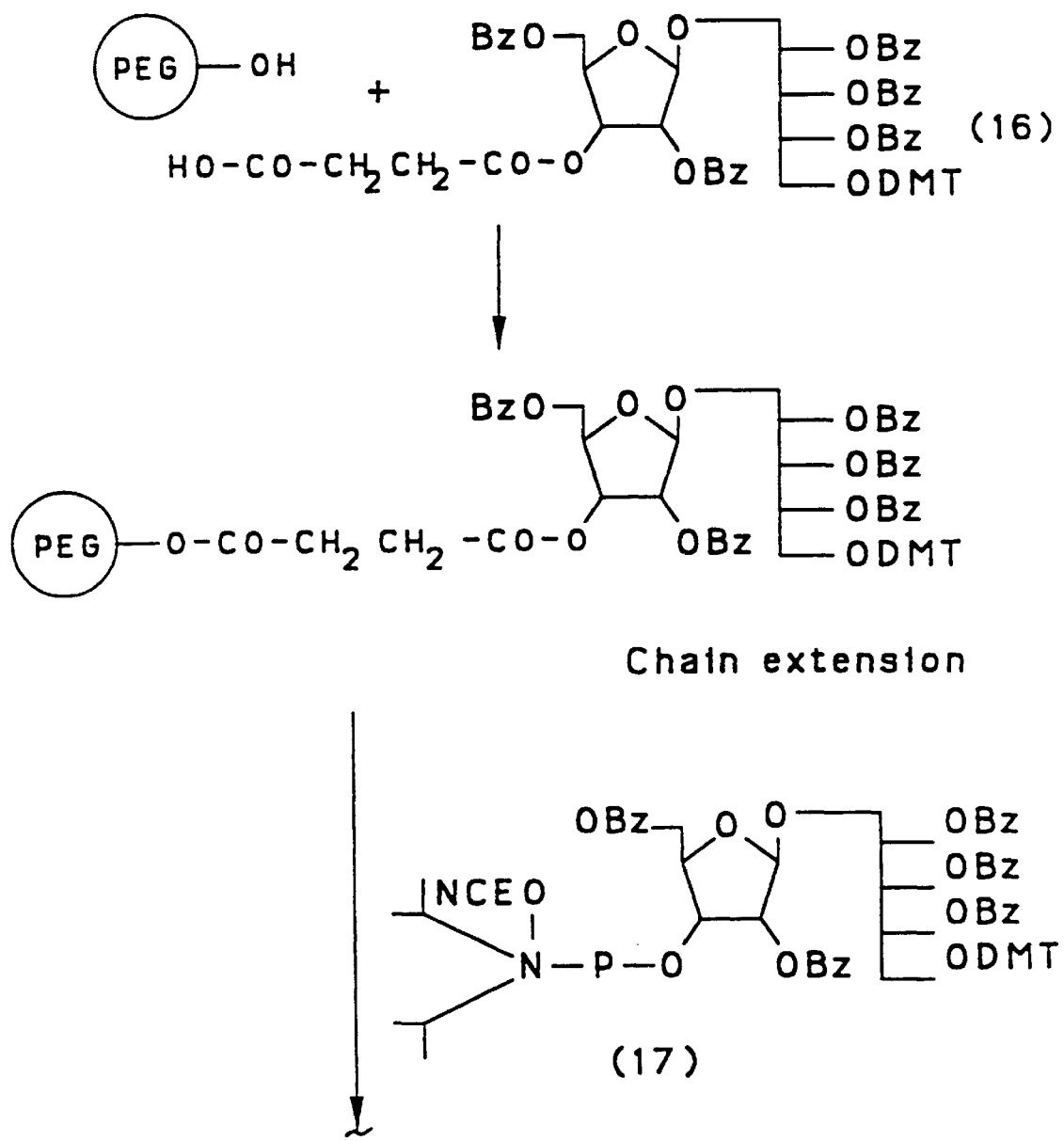
Figure 13B:
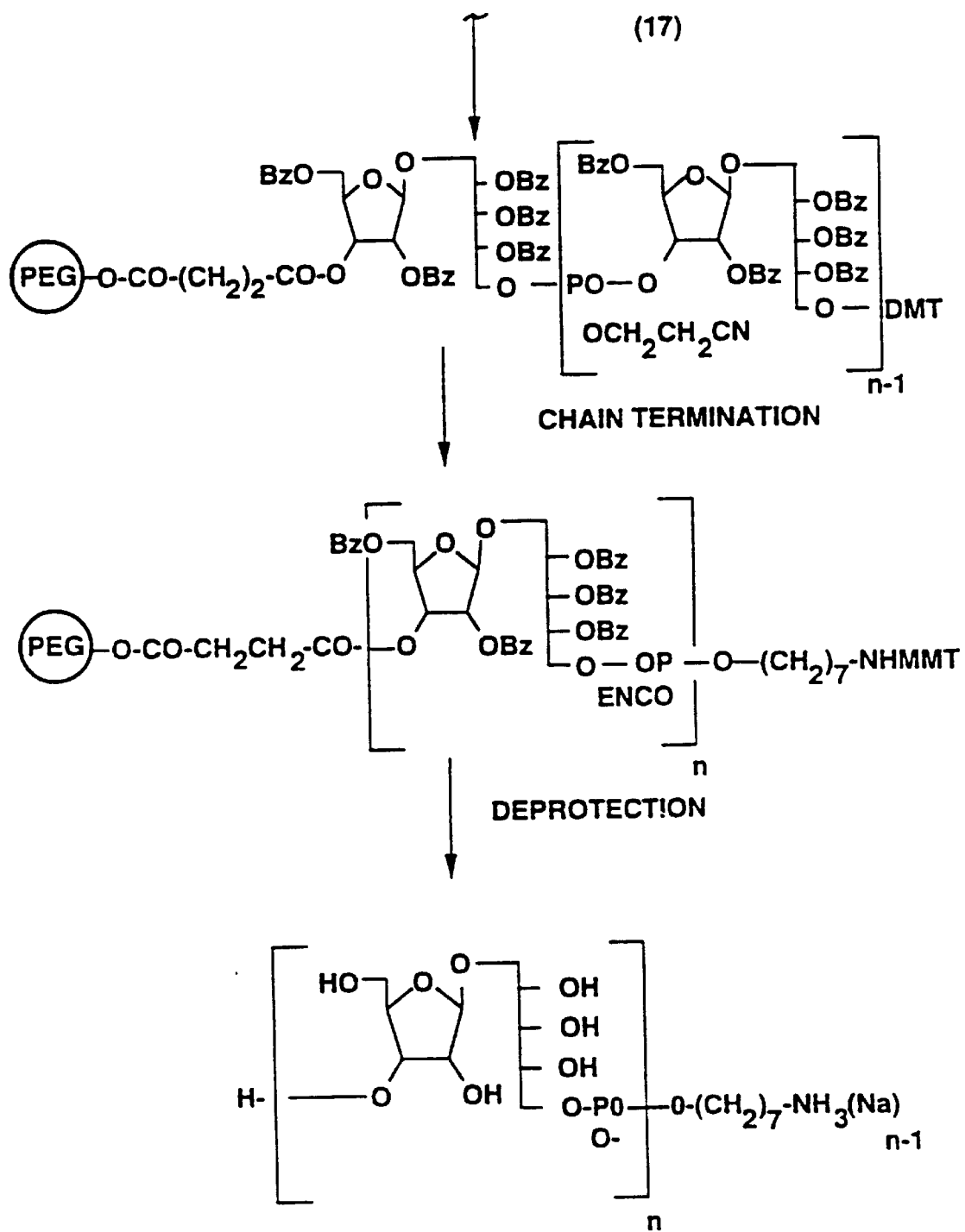
Figure 14A:
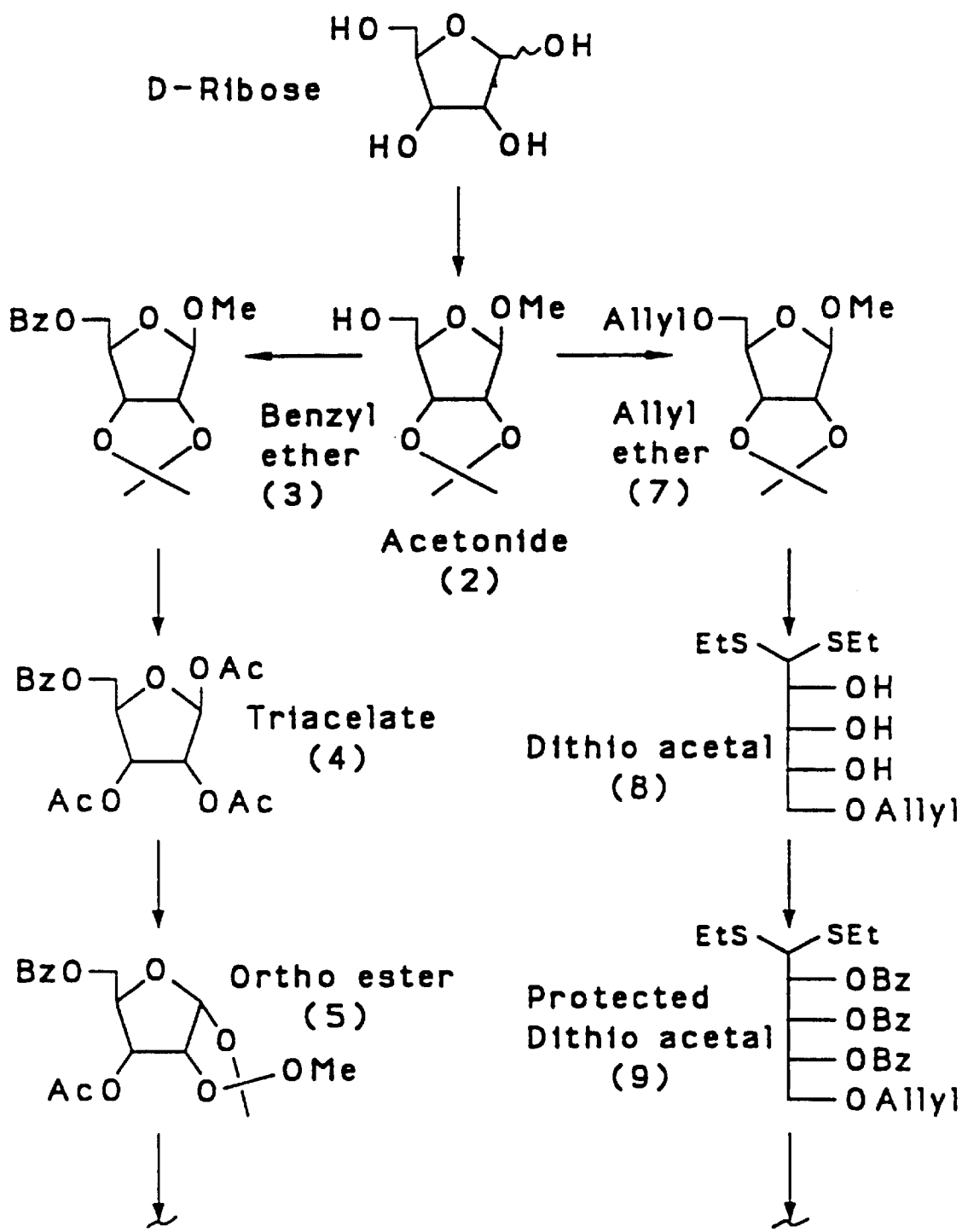
Figure 14B:
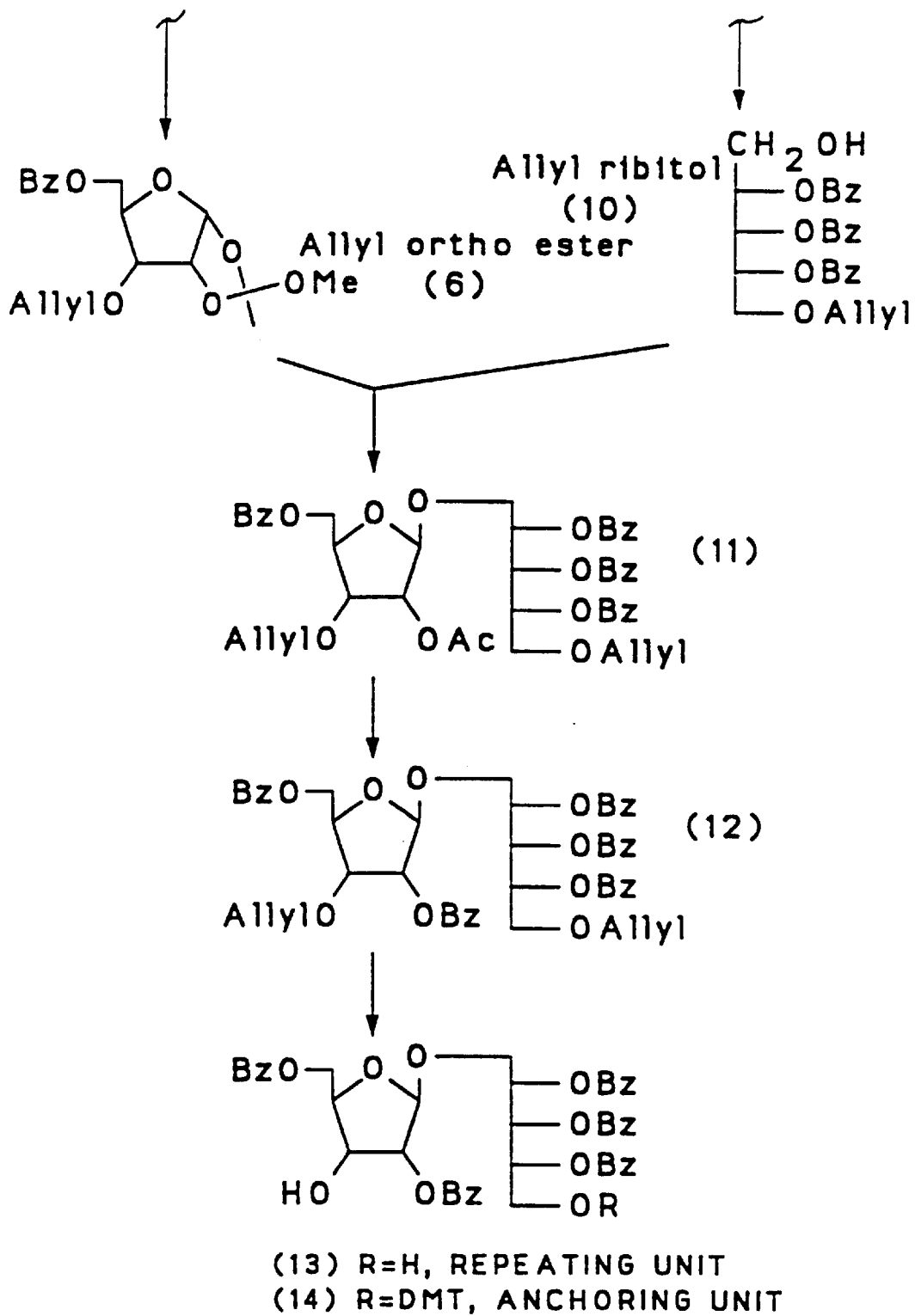
Figure 14C:
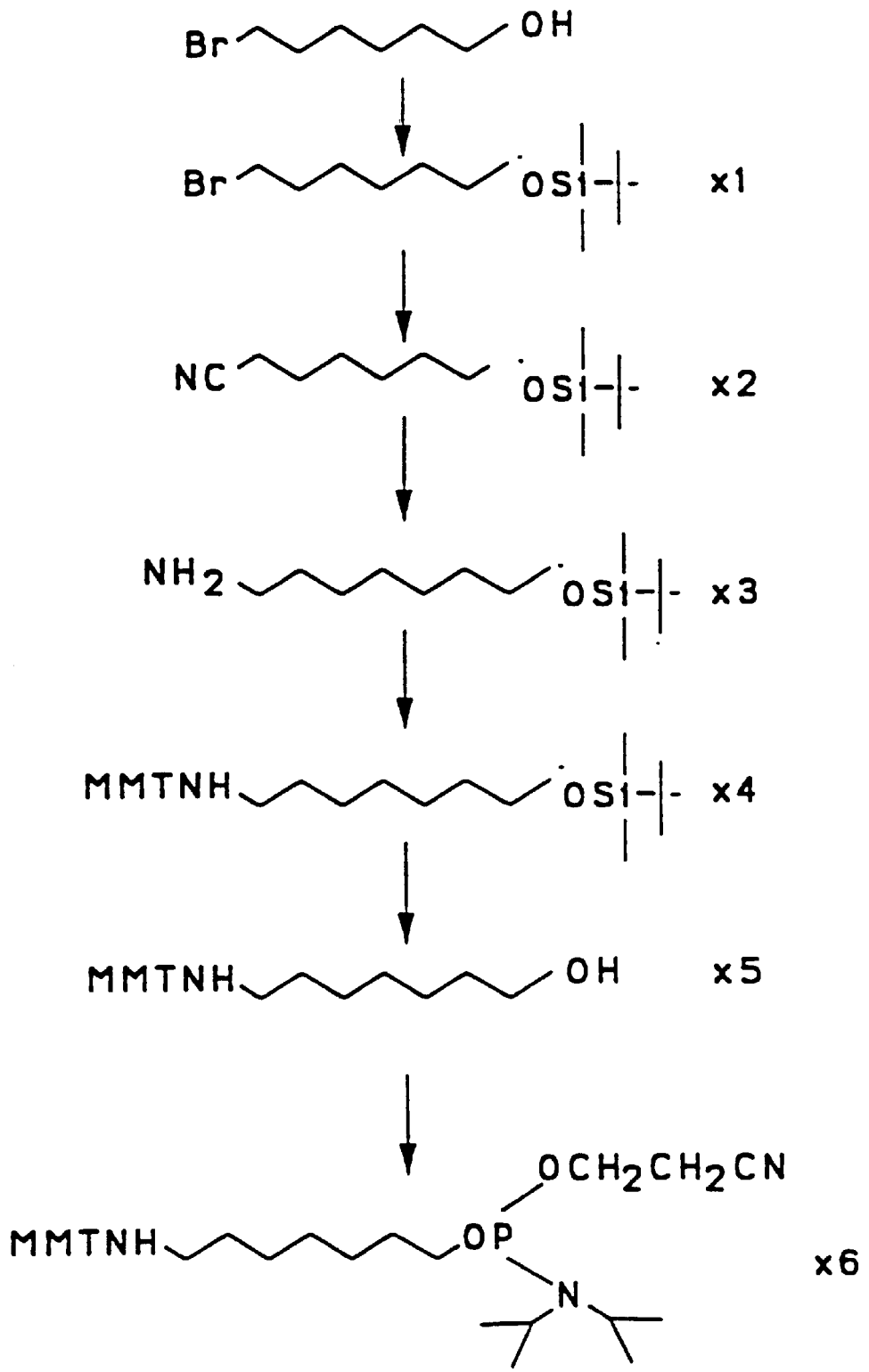
Figure 16:
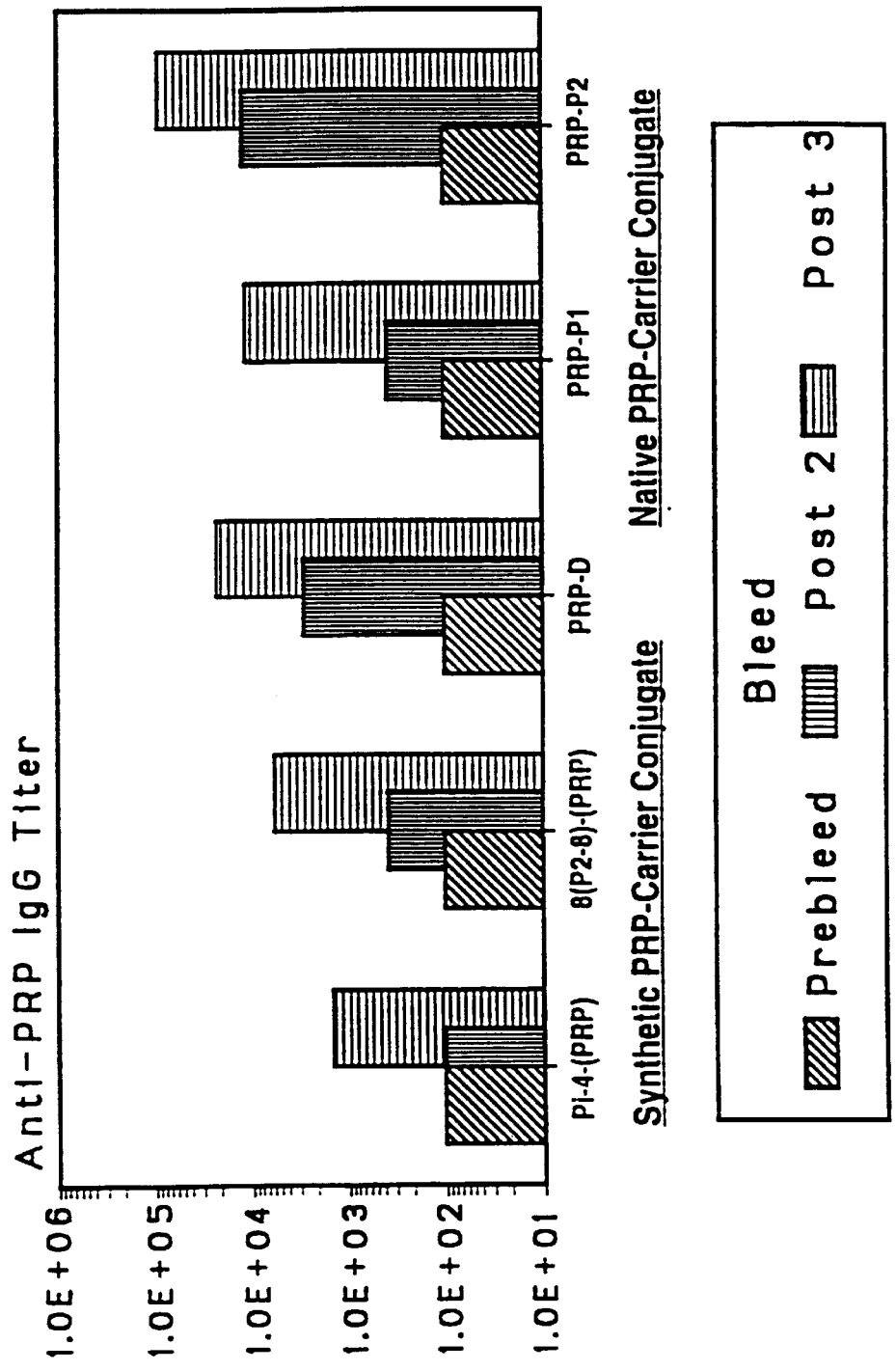
Figure 17:
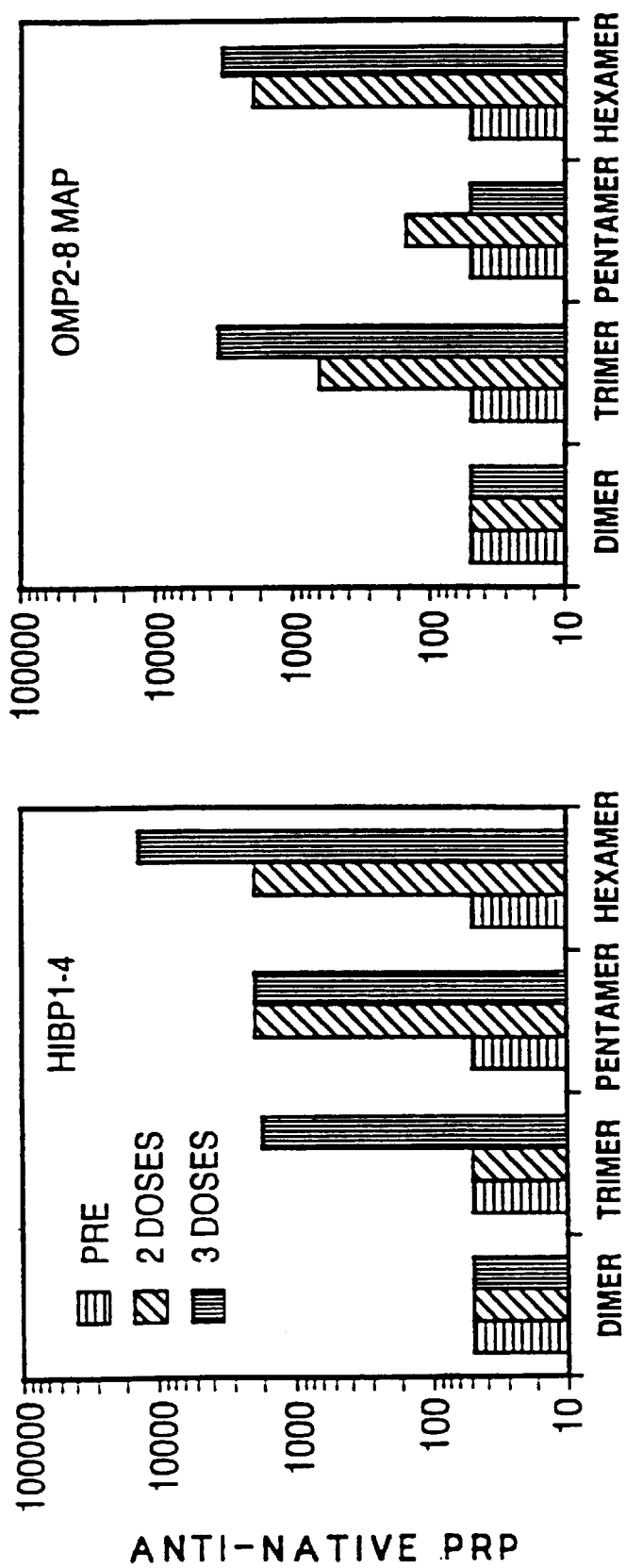

FIGS. 2A and 2B show the predictive structure of the OMP P1 by conventional structural analysis algorithms. Hydrophilicity plots predicted by Hopp (ref. 30). The values are derived from the average of heptapeptide windows and are plotted at the midpoint of each segment;

FIGS. 3A, 3B and 4, each comprising upper and lower panels show respectively, the predictive structure of the OMP P2 and P6 by conventional structural analysis algorithms. The upper panel, secondary structure analysis of the local average α-helix and β-turn potentials according to Chou and Fasman (ref. 29). The lower panel, hydrophilicity plots predicted by Hopp and Woods (ref. 30). The values are derived from the average of heptapeptide windows and are plotted at the midpoint of each segment;

FIG. 5, comprising three panels, contains a diagrammatic representation of the immunodominant B- and T-cell epitopes of Hib OMP P1;

FIG. 6, comprising three panels, contains a diagrammatic representation of the immunodominant B- and T-cell epitopes of Hib OMP P2;

FIG. 7, comprising three panels, contains a diagrammatic representation of the immunodominant B- and T-cell epitopes of Hib OMP P6;

FIGS. 8A, 8B and 8C show P6 peptides ELISA reactivity with guinea pig, rat and rabbit anti-P6 antisera;

FIG. 9 shows P1 peptides ELISA reactivity with three human convalescent sera;

FIG. 10 shows P2 peptides ELISA reactivity with three human convalescent sera;

FIGS. 11A, 11B and 11C show the proliferative response of P1-specific murine T-cell lines to P1 peptides with the immunodominant T-cell epitopes highlighted with an asterisk;

FIGS. 12A, 12B and 12C show the proliferative response of P1-specific murine T-cell lines to P1 peptides with the immunodominant T-cell epitopes highlighted with an asterisk;

FIGS. 13A, and 13B contain 1 flow chart of PRP synthesis using PEG as solid support;

FIGS. 14A, and 14B and 14C contain a flow chart of the synthesis of PRP intermediates. Bz, benzyl; Ac, acetyl; ETS, ethylthio; Me, methyl; Allyl, allyl; DMT, 4,4'-dimethoxytrityl; NCE, cyanoethyl; MMT, 4-methoxytrityl;

FIG. 15 shows the rabbit immune response to synthetic PRP dimer and trimer conjugated to tetanus toxoid;

FIG. 16 shows the rabbit immune response to different types of PRP-carrier conjugates; and FIG. 17 shows the rabbit immune response to different types of synthetic pentamer and hexamer to HibP1-4 and MAP of OMP.

DETAILED DESCRIPTION OF THE INVENTION

The present invention relates to the identification of immunogenic epitopes of Hib OMPS, novel synthetic PRP-peptide conjugates and vaccines made therefrom. These novel immunogenic agents are prepared by chemically synthesizing peptides sharing antigenic determinants with the Hib OMPS P1, P2 and P6. The peptides or lipopeptides are used either individually or linked to synthetic PRP oligomers as vaccines. They can also be polymerized to produce alternative vaccines. These vaccines can be used to immunize against Hi infection when administered to mammals, for example, by the intramuscular or parenteral route, or when delivered to the mucosal surface using microparticles, capsules, liposomes and targeting molecules, such as toxins and antibodies.

Reference will now be made in detail to the presently preferred embodiments of the invention, which together with the following Examples, serve to explain the principle of the invention. For clarity of disclosure, and not by way of limitation, the detailed description of the invention is divided into the following sections:

(i) Epitope Prediction and Peptide Synthesis;

(ii) Identification and Characterization of Immunodominant B-cell epitopes of Hi OMPs P1, P2 and P6 Using Synthetic Peptides;

(iii) Identification and Characterization of Immunodominant T-cell epitopes of Hi OmPs P1, P2 and P6 Using Synthetic Peptides;

(iv) Immunogenicity of Hib OMPs Peptides;

(v) Solid-phase Carbohydrate Synthesis of PRP Oligomers using PEG as Support;

(vi) Conjugation of synthetic PRP Oligomers to Hib OMP Peptides and Immunochemical Characterization of the Glycoconjugates; and (vii) Utility of Hi Synthetic PRP-peptide Conjugate vaccines.

Epitope Prediction and Pentide Synthesis

To map the immunodominant T-cell or B-cell epitopes of Hi OMPs, 13, 17 and 7 overlapping synthetic peptides covering most of the P1, P2 and P6 protein sequences (Tables 1, 2 and 3 below), respectively were synthesized using the t-Boc solid-phase peptide synthesis as described in detail in Example 12 below. The length of the peptides was chosen based on the high index of hydrophilic β-turns estimated by secondary structure prediction analysis according to conventional algorithms (refs. 29 to 31) (FIGS. 2, 3, and 4). Such peptides are likely to be surface-exposed and antigenic. Peptides more than 25 residues in length were selected to better mimic native epitopes as suggested by the work of Van Regenmortel (ref. 32). occasionally an additional cysteine residue was added to either the N-terminal or the C-terminal end of the peptides for site-specific conjugation purposes.

Identification and Characterization of Immunodominant Epitopes of Hi OMPs P1, P2 and P6 Using Synthetic Peptides To identify the immunodominant B-cell epitopes of Hib OMPs, rabbits, guinea pigs, and mice of different haplotypes ($H-2^a$, $H-2^b$, $H-2^d$, $H-2^k$, $H-2^q$, and $H-2^s$) were immunized with either purified P1, P2 or P6 proteins in the presence of Freund's adjuvant. After both primary and secondary immunizations, all animals mounted a strong and specific anti-OMP antibody response as judged by P1-, P2- and P6-specific ELISA (Tables 4, 5 and 6 below) and immunoblot analysis. As previously reported by Granoff and Munson (ref. 6), rabbit anti-P1, anti-P2 and anti-P6 antisera consistently protected infant rats against live Hib challenge. The guinea pig anti-P2 antisera were also protective in this model.

To map the linear B-cell epitopes of Hib OMPS, overlapping synthetic peptides covering most of the sequences of P1, P2 and P6 were individually coated onto ELISA plates and probed with the various anti-P1, anti-P2 and anti-P6 antisera as described in Example 17 below. The results are summarized in FIGS. 5, 6, and 7. The immunodominant linear B-cell epitopes of P1 were found to be located within the peptide sequences corresponding to amino acids 39 to 64, 103 to 137, 165 to 193, 248 to 283, 307 to 331, 400 to 437 and 179 to 218 of the mature P1 protein of the Hib MinnA strain (see Table 1, below). The P2 peptides containing immunodominant B-cell epitopes were identified as residues 53 to 81, 148 to 174, 241 to 265 and 314 to 342 of the mature P2 protein of the Hib MinnA strain (see Table 2 below). Similarly, the P6 peptides containing immunodominant B-cell epitopes were residues 73 to 96, 90 to 114 and 109 to 134 of the mature P6 protein of the Hib MinnA strain (see Table 3 below) (FIG. 8). Interestingly, three human convalescent sera also reacted strongly with the P1 and P2 immunodominant epitopes described above (FIGS. 9 and 10). In addition, a strain-specific P1 protective B-cell epitope was mapped to a region corresponding to residues 165–193 of the P1 protein. These results indicate that the B-cell epitopes described above can be used as target antigens in diagnostic kits to detect the presence of anti-Hi antibodies in biological fluids.

Identification and Characterization of Immunodominant T-cell Epitopes of Hi OMPs P1, P2 and P6 Using Synthetic Peptides The Hib OMPs-specific T-cell epitopes were determined using P1, P2 and P6 peptides and T-cell lines obtained from a panel of different strains of mice immunized with native OMPs. The lymphocyte proliferative responses of the OMP-specific T-cell lines to overlapping P1 peptides (13 peptides), P2 peptides (17 peptides) and P6 peptides (7 peptides) were determined in conventional proliferation assays as described in Example 19 below. The results (FIGS. 11 and 12 and Table 7 below) revealed that certain synthetic peptides only elicited proliferative responses, and that the recognition of T-cell epitopes was MHC-restricted. Synthetic peptides corresponding to residues 39 to 64, 226 to 253, 339 to 370 and 400 to 437 of P1; residues 125 to 150, 193 to 219, 219 to 244 and 241 to 264 of P2; residues 19 to 41, 35 to 58, 73 to 96 and 109 to 134 of P6, when presented in the appropriate murine MHC context, were shown to be highly stimulatory for their corresponding OMP-specific murine T-cell lines. Therefore, these immunodominant T-cell epitopes can be used as autologous carriers for PRP, and/or OMP B-cell epitopes to enhance their immunogenicity.

Immunogenicity of Hib OMPs Peptides

To determine whether synthetic OMP peptides were possible vaccine candidates, free peptides and peptide-KLH conjugates were assessed individually for their immunogenicity. Rabbit anti-peptide antisera were tested for their reactivity with the immunizing peptides and their parental proteins by ELISA and immunoblotting. As shown in Table 8 below, all anti-P1 peptide antisera except those raised against HIBP1-8 or HIBP1-8-KLH conjugate were shown to be specific for their respective immunizing peptides by ELISA. The induction of high titers of peptide-specific IgG antibodies by free peptide dearly indicates that the peptide comprises both a functional T-helper determinant and a B-cell epitope(s). In addition, anti-HIBP1-4, anti-HIBP1-5, anti-HIBP1-7, anti-HIBP1-9, anti-HIBP1-10, anti-HIBP1-11 and anti-HIBP1-14 antisera recognized P1 in all assays used, which indicates that these regions are antigenic and free to interact with antibodies. Since these peptides were shown to contain potent T-helper determinant and peptide-KLH conjugates induced strong IgG antibody responses in rabbits, it is obvious that they can act as antigens in a vaccine preparation.

It was of interest to determine whether Hib P1 peptide-specific antisera would cross-react with native P1 from non-typeable strains of *H. influenzae*. Rabbit antisera raised against the synthetic peptides HIBP1-1, HIBP1-3, HIBP1-5, HIBP1-6, HIBP1-7, HIBP1-9, HIBP1-12 and HIBP1-13 recognized the P1 protein from both typeable and non-typeable isolates. These results suggest that the peptides corresponding to residues 1 to 29, 39 to 64, 103 to 137, 189 to 218, 226 to 253, 248 to 283, 307 to 331, and 400 to 437 of the mature P1 protein, contain epitopes highly conserved among typeable and non-typeable strains of *H. influenzae*.

Rabbit antisera raised against P2 peptide-KLH conjugates were assayed for reactivity against native P2 in P2-specific ELISAs and by immunoblot analysis. Although all peptide-specific antisera, except antisera raised against HIBP2-26-KLH and OMP2-13-KLH conjugates, recognized P2 in the immunoblots, only Porin-1, OMP2-5, -7, -8, -10, -12, and CHIBP2 peptide-KLH conjugates were found to elicit antibodies that cross-reacted with native P2 in the P2-specific ELISA (Table 9 below). All unconjugated peptides except for Porin-1 and HIBP2-26 emulsified in complete Freund's adjuvant induced very strong peptide-specific antibody responses against P2 in immunoblots (Table 9 below). In addition, antisera raised against unconjugated peptides OMP2-4, -8, -10, -11, -12, and -13 reacted strongly with purified P2 in the P2-specific ELISA. These data indicate that these peptides contain potent functional T-helper cell epitopes and immungenic B-cell epitopes. Furthermore, P2 purified from three different non-typeable isolates SB30, SB32 and SB33 were used as target antigens in immunoblots. Rabbit anti-Porin-1, OMP2-5, -8, -10, -11, -12 and -13 antisera reacted strongly with P2 from all three non-typeable isolates. These results suggest that the peptides corresponding to residues 1–19, 125–150, 183–219, 241–265, 263–289, 285–306 and 302–319 contain epitopes conserved among typeable and non-typeable strains of *H. influenzae*.

Rabbit antisera raised against P6 peptides were assayed for reactivity against P6 in the P6-specific ELISA and by immunoblot analysis. All peptide-specific antisera, except those raised against P6-4, recognized native P6 in the P6-ELISA, and were found to cross-react with both typeable and non-typeable P6 in immunoblots (Table 10 below). These data indicate that P6 peptides contain potent functional T-helper cell epitopes and immunogenic B-cell epitopes. Furthermore, these results confirm that the P6 protein is highly conserved among typeable and non-typeable strains of *H. influenzae*. Therefore, these conserved epitopes of P1, P2 and P6 can be used either individually or in combination to prepare a cross-reactive (typeable and non-typeable strains of Hi) synthetic vaccine. Peptides described above can be further either polymerized, or modified with lipids as lipopeptides or linked to synthetic PRP as synthetic glycopeptide or lipoglycopeptide conjugates to produce alternate vaccines. These vaccines can be used to immunize against Hi infection when administered to mammals, for example, by the intramuscular or parenteral route, or when delivered to the mucosal surface using microparticles, capsules, liposomes and targeting molecules such as toxins and antibodies.

Further experiments were performed to determine whether synthetic chimeric peptides comprising identified immunodominant T-and B-cell epitopes from either P1 or P2 or P6 linked in tandem could elicit strong protective antibody responses against Hi infection. The peptides containing the amino acid sequences VKTIGDKRTLTLNTCAR-TRTTETGKGVKTEKEKSVGV GLRVYF, VKTIGDKNTLTLNTFGDGFYAQGYLETR-FVTKASENG SNFGDC, VXTIGDKNTLTLNTCGANYL-LAQKREGAKGENIRPND KAGEV, VKTIGD-KRTLTLNTDIVAKIAYGRTNYKYNESDEHKQ QLNGC, VKTIGDKRTLTLNTYAKTKNYKIKHEKRYFVSPGFQY ELC, GYLETRFVTKASENGSDFKEVKTIGD-KRTLTLNTTAN YTSQAHANLYGLNLNYSF, AKGEN-KRPNDKAGEVFKEVKTIGDKRTLTLNTTANY TSQAHANLYGLNLNYSF, and ARTRTTETGKGVK-TEKFKEVKTIGDKRTLTLNTTANYTSQA- HANLYGLNLNYSF (SEQ ID NOS: 42 to 49 respectively) were synthesized, purified and used to immunized rabbits in the presence of either CFA or alum. The results are summarized in Table 11 below. All anti-peptide antisera strongly reacted with the respective immunizing peptides, but not all chimeric peptides elicited antibodies against the native OMPs. The best immunogens were peptides 1P13-2P8 and 2P6-1P13, which elicited antibodies recognizing both the native P1 and P2 proteins when administered in the presence of alum. Since these peptides contain epitopes conserved among Hi strains, they can be used as additional antigen or modified as lipopeptides, or linked to synthetic PRP oligomers as vaccines. These vaccines can be used to immunize against Hi infection when administered to mammals, for example, by the intramuscular or parenteral route, or when delivered to the surface mucosal surface using microparticles, capsules, liposomes and targeting molecules such as toxins and antibodies.

Synthesis of PRP Oligosaccharide Fragments Using PEG

The synthetic PRP is prepared by a combination of solid/liquid-phase synthesis and the highly efficient phosphoramidite method, as outlined in FIGS. 13 and 14. It is a novel process that utilizes polyethylene glycol monomethyl ether (PEG) as solid support. The solid-phase support contains high number of chemically reactive functional groups ranging from about 200 to 500 μmol/g of support, as compared to the about 30 to 35 μmoles of reactive groups per g of conventional supports, such as controlled pore glass. The synthesis uses only stoichiometric amounts of synthetic PRP repeating unit in each coupling cycle, as compared to a 5 to 10 fold molar excess in the conventional solid-phase synthesis. Furthermore, PEG is soluble in the reaction solvents so that the coupling efficiency is about 95 to 98% for each cycle. At the end of the cycle, PEG-bound synthetic PRP is precipitated with ether to remove any by-products. For the synthetic PRP hexamer, the final yield was about 70%. Thus, the present synthesis process is very fast, cost-effective and simple to scale-up for commercial applications, in contrast to solution-phase synthesis which is laborious, expensive and time-consuming.

The following paragraphs describe the synthesis process in greater details. The PRP repeating unit for oligomer initiation is a compound represented by the formula:

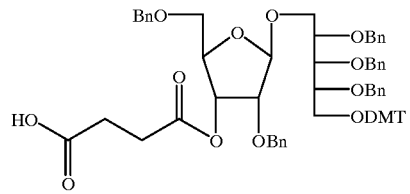

where Bn and DMT are benzyl and dimethoxytrityl groups, respectively. This repeating unit is coupled to PEG as described in Example 10 below, detritylated with trichloroacetic acid (TCA), and then coupled with another PRP repeating unit for chain elongation, represented by the formula:

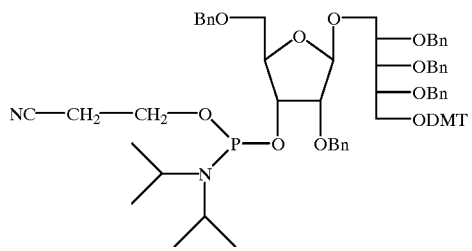

The resulting compound is then detritylated with TCA. In each cycle, the chain elongation is accomplished by coupling the detritylated chain in the presence of a catalyst, preferably tetrazole. After each coupling step the oxidation of phosphorous is accomplished using an oxidizing agent, preferably t-butyl hydroperoxide. The synthesis cycle (Detritylation, coupling, and oxidation steps) is repeated until an oligomer of the desired length is obtained. The PRP oligomer is terminated by reacting with a chain terminator represented by the following formula:

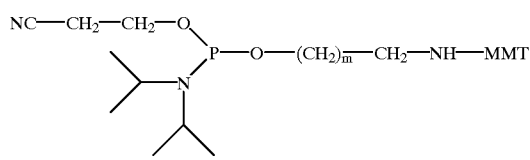

where m is an integer, preferably from 4 to 6, and MMT is monomethoxytrityl. After chain termination the resulting PEG-supported oligomer, which forms one aspect of this invention, is then cleaved from the solid support, preferably through cleavage by ammonolysis. The recovered material is represented by the formula:

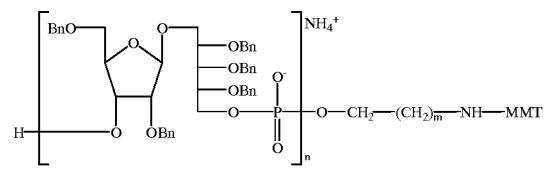

where n is an integer, preferably from 3 to 20, and m is an integer, preferably from 4 to 6, Bn is benzyl, and MMT is monomethoxytrityl. The compound is associated with a counter ion. Preferably, the ion is ammonium, as illustrated, or substituted ammonium.

The side-chain protecting groups are removed by hydrogenation with palladium on charcoal in the presence of water/acetic acid/t-butyl alcohol as described in Example 10 below. The resulting oligomer may be purified by standard techniques, preferably by combination of gel and anion exchange chromatography.

As described above, coupling the compound X6 (FIG. 14) at the last step before chain-termination, it is very easy to convert the synthetic PRP oligomer to comprise a chemically reactive functional group represented by the following formula:

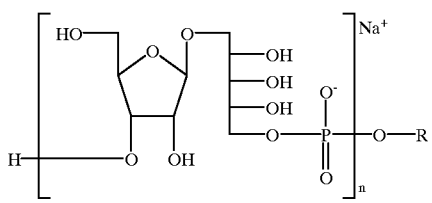

where n is an integer, preferably from 3 to 20, and R is a linker fragment defined by —CH$_2$—(CH$_2$)$_m$—X, wherein m is an integer, preferably from 3 to 5, inclusive, and X is a chemically reactive functional group, such as —CH$_2$NH$_2$, —CH$_2$SH, or an amino-reactive group such as an halogen, methanesulfonyl, triflouromethanesulfonyl or toluenesulfonyl, and the like, or a photoactivatable group, such as phenyl azide, nitrophenyl, benzylphenyl, and the like.

The compound containing the functional group may be formed in a conjugate in the most preferred embodiment of the invention, the conjugate being represented by the following formula:

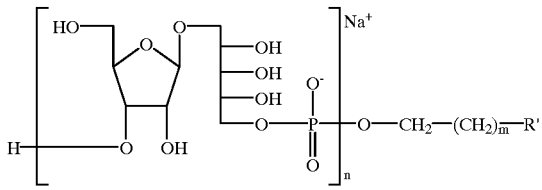

where n is an integer, preferably from 3 to 20, and m is an integer, preferably from 3 to 5, and R' is —(CH$_2$— carrier), wherein Y is a linker molecule which may be m-maleimidibenzoyl-N-hydroxysuccinimide and the carrier is a Hi peptide or MAP system thereof. The conjugate will be associated with a counter ion. Preferably, the ion is Na$^+$, as illustrated.

It is obvious that there are numerous ways to prepare synthetic PRP. The technology that includes those known in the art, for example, the European Patent Office Publications 0 320 942 (ref. 28) and 0 276 516 (ref. 27), as well as those ones that could be used in conjunction with the present invention, are well within the scope of the invention.

Immunochemical Characterization of Synthetic PRP Oligosaccharide Conjugated to Peptides Containiny T-helper Cell Epitope(s)

Figure 1:
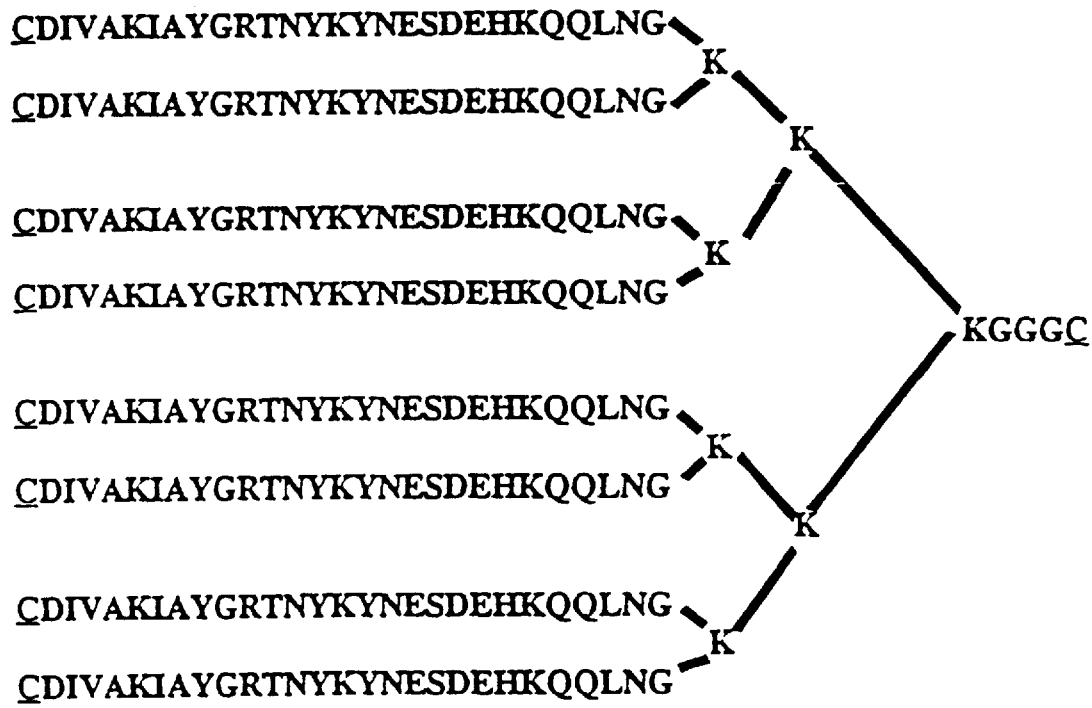
FIG. 1 shows the amino acid sequences of peptide carriers used in synthetic PRP-peptide conjugates studies reported herein. With respect to this Figure, the synthetic peptides identified therein have the following SEQ ID NOS.

Peptides which may be utilized according to the invention include any peptide which is safe when administered to young mammals and may serve as an immunologically effective T-cell epitope, for example, P24E, a human T-cell epitope from the HIV-1 gag protein p24 (FIG. 1). In particular embodiments, peptides from outer membrane proteins of Hib were used and the conjugation technology was fully described in Examples 11 and 13 below. To determine the minimum number of repeating units required to generate anti-PRP IgG antibody response, synthetic PRP oligomers (dimer and trimer) were coupled to tetanus toxoid and the glycoconjugates injected into rabbits in the presence of alum. The results presented in FIG. 15, indicate that, to be immunogenic the synthetic PRP oligomer requires at least three repeating units.

According to the invention, the fully synthetic PRP-peptide conjugate vaccine candidates were prepared by coupling synthetic PRP oligomers to well characterized synthetic T-cell epitopes of Hib OMPs through a cysteine residue added either at the N-terminal or the C-terminal end of the peptides, for example, peptide HIBP1-4 (residues 165–193 of the P1 protein) which had been identified to comprise a Hib strain-specific protective B-cell epitope and at least one functional T-helper cell epitope.

To prepare an effective synthetic PRP-peptide conjugate vaccine, several factors which may affect the immunogenicity of the carbohydrate antigen need to be carefully examined. These factors are (i) the chain length of the oligosaccharide; (ii) the site of conjugation of sugar moieties with respect to the T-cell epitope; (iii) the density of carbohydrate antigen on the peptide; (iv) the conjugation methodologies which influences the stability of the glycoconjugate; (v) the requirement of linkers or spacers between the carbohydrate moiety and the carrier peptide for opimal antigen presentation and processing. To this end, a pair of peptides, HIBP1-4 and CHIBP1-4 (FIG. 1) which differ only by an additional cysteine residue added either at the C-terminal end (HIBP1-4—SEQ ID NO: 51) and the N-terminal end (CHIBP1-4—SEQ ID NO: 52), respectively, were synthesized, purified, and used as T-cell epitope carriers to examine the effect of the orientation of sugar moiety relative to the T-cell epitope on the construct immunogenicity. A synthetic PRP trimer was used as carbohydrate antigen. The two PRP-peptide conjugates (PRP-CHIBP1-4 and HIBP1-4-PRP) were prepared and injected into rabbits in the presence of alum. After 3 immunizations, the rabbit antisera were assayed for anti-PRP and anti-peptide IgG antibody titers. Both conjugates elicited strong anti-peptide and anti-P1 antibody responses, but only the synthetic HIBP1-4-PRP elicited an anti-PRP IgG antibody response. These results suggest that the orientations of the sugar moiety relative to the T-cell epitope may significantly influence the host immune response to the carbohydrate antigen.

To determine whether all peptides containing functional T-cell epitope(s) could efficiently present synthetic PRP oligomers to the immune system, two more peptides (COMP2-8—SEQ ID NO: 53 and P24EC—SEQ ID NO: 56) known to contain functional T-cell epitope(s), were conjugated to the synthetic PRP trimer. The glycopeptide conjugates were absorbed to alum and used to immunize rabbits. The results are summarized in Table 12 below. Both glycopeptide conjugates (COMP2-8-PRP and P24EC-PRP) elicited anti-PRP IgG antibody responses.

To determine the effect of carbohydrate density on the immunogenicity of synthetic glycopeptide conjugate vaccines, the synthetic PRP trimer was conjugated to a multiple antigen peptide system (MAPs) containing eight branched OMP2-8 peptides(residues 193–219 of the P2 protein) (FIG. 1—SEQ ID NO: 54). Although nine cysteine residues were available for conjugation purposes, only five PRP trimer molecules were found to be coupled to one MAP molecule. Nevertheness, after three injections of 50 $\mu$g of the synthetic glycopeptide conjugate in the presence of alum, both rabbits mounted a strong anti-PRP IgG antibody response. The anti-PRP IgG antibody titer was about four-fold higher than those obtained with the linear peptide-PRP conjugate (Table 12 below). Furthermore, the anti-peptide and anti-P2 antibody reponses were 1 to 2 orders of magnitude higher than those obtained with the linear peptide-PRP conjugate. Further analysis of the results shown in FIG. 16 revealed that Hib MAPs conjugated to synthetic PRP oligomers are good vaccine candidates which can elicit high titers of anti-PRP IgG antibodies comparable to those obtained with native PRP coupled to either diphtheria toxoid or P1 or P2 proteins.

To determine whether the length of the carbohydrate repeating units affected the immunogenicity of the carbohydrate antigen in the glycoconjugate, the synthetic PRP dimer, trimer, pentamer, hexamer and native PRP (molecular weight 30 kDa) were coupled either to linear peptide HIBP1-4 and OMP2-8 MAP, respectively. Surprisingly, both peptides conjugated to native PRP failed to elicit anti-PRP IgG antibody responses. In contrast, both the PRP pentamer and hexamer conjugated to the linear peptide HIBP1-4 elicited a strong and consistent anti-PRP IgG antibody response (FIG. 17). The OMP2-8 MAP conjugated to the synthetic PRP hexamer was also highly immunogenic. The synthetic PRP dimer was not immunogenic and was consistent with previous results described above.

Utility of Synthetic Glycopeptide Conjugation Technology

In preferred embodiments of the present invention, the glycoconjugate technology can be generally utilized to prepare conjugate vaccines against pathogenic encapsulated bacteria. Thus, the glycoconjugate technology of the present inventions may be applied to vaccinations to confer protection against infection with any bacteria expressing potential protective polysaccharidic antigens, including *Haemophilus influenzae, Streptococcus pneumoniae, Escherichia coli, Neisseria meningitidis, Salmonella typhi, Streptococcus mutans, Cryptococcus neoformans, Klebsiella, Starhylococcus aureus* and *Pseudomonas aerogenosa.*

In particular embodiments, the synthetic glycoconjugate technology may be used to produce vaccines eliciting antibodies against proteins or oligosaccharide. Such vaccines may be used, for example, to induce immunity toward tumor cells, or to produce anti-tumor antibodies that can be conjugated to chemotherapeutic or bioactive agents.

It is understood that the application of the methology of the present invention is within the capabilities of those having ordinary skills in the art. Examples of the products of the present invention and processes for their preparation and use appear in the following Examples.

It is also understood that within the scope of the invention are any variants or functionally equivalent variants of the above peptides. The terms "variant" or "functionally equivalent variant" as used above, mean that if the peptide is modified by addition, deletion or derivatization of one or more of the amino acid residues, in any respect, and yet acts in a manner similar to that of P1, P2 and P6 peptides for any *Haemophilus influenzae* isolates, then it falls within the scope of the invention.

Given the amino acid sequence of these peptides (Tables 1 to 3 and 11) and any similar peptide, these are easily synthesized employing commercially available peptide synthesizers, such as the Applied Biosystems Model 430A, or may be produced by recombinant DNA technology.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Immunological methods may not be explicitly described in this disclosure but are well within the scope of those skilled in the art.

EXAMPLES

Example 1

Preparation of 2,3,4-Tri-O-benzyl-1-O-[2,5,-di-O-benzyl-β-D-ribofuranosyl]-5-O-(4,4'-dimethoxytrityl)-D-ribitol (compound 14, FIG. 14).

At room temperature, a 4,4'-dimethoxytrityl chloride (6.2 g) was added to a 200 mL of dichloromethane solution of containing 10.2 g of 2,5-di-O-benzyl-β-D-ribofuranosyl 2,3,4-tri-O-benzyl-D-ribitol (compound 13, in FIG. 14) prepared from D-ribose via 12 intermediate products as previously described (refs. 33 to 36), pyridine (3.4 mL) and 4-dimethylaminopyridine (860 mg). After stirring for 18–24 h, the reaction mixture was poured into a saturated solution of sodium bicarbonate. The aqueous layer was extracted with dichloromethane, dried and the solvents were evaporated. The product was purified using silica gel chromatography, and its structure was confirmed by NMR.

Example 2

Preparation of 2,3,4-Tri-O-benzyl-1-O-[2,5-di-O-benzyl-3-O-succinyl-β-D-ribofuranosyl]-5-O-(4,4'-dimethoxytrityl)-D-ribitol (Compound 16, FIG. 13)

To a solution of 1.34 g of the product from Example 1 in dry pyridine (4.5 mL) were added succinic anhydride (390 mg) and 4-dimethylaminopyridine (240 mg). The reaction mixture was stirred in a water bath at 50 to 80° C. for 3 to 10 h. After the addition of water (2.0 mL) the reaction mixture was concentrated by rotory evaporation. Chromatography of the mixture on a column of silica gel using dichloromethane:methanol: triethylamine in a ratio of 95:5:2.5 (V:V:V) provided the product as a triethylammonium salt whose structure was confirmed by NMR.

Example 3

Preparation of Ribosylribitol Phosphoramidite

To a solution of Compound 16 (1.2 g in 5 mL of dry dioxane), N,N-diisopropylethylamine (1.4 mL) and 2-cyanoethyl N,N-diisopropylchlorophosphoramidite (640 μL) were added. After stirring for 1–3 h, additional amounts of N,N-diisopropylethylamine (430 μL) and 2-cyanoethyl N,N-diisopropylchlorophosphoramidite (250 μL) were added. The reaction mixture was diluted 3-fold with dichloromethane and extracted with an equal volume of 1M triethylammonium bicarbonate solution, brine solution and dried with anhydrous sodium sulphate. The product was purified on silica gel, and its structure was confirmed by NMR.

Example 4

Preparation of 1-t-Butyldimethylsilyloxy-6-cyano-hexane (Compound X2, FIG. 14)

Sodium cyanide (1.2 g) dissolved in dimethylsulphoxide was heated at 90° C. for 30 min. Solid 1-t-butyldimethylsilyloxy-6-bromohexane (5.8 g, compound X1) prepared according to the method previously described (ref. 37), then was added into the sodium cyanide solution. After heating at 120–130° C. for 20–180 min, the reaction mixture was poured into ice-cold water and the aqueous layer was extracted with ether, washed with brine, dried and concentrated. The product was distilled at 0.5 Torr and 107° C. to give a colorless oil. High resolution mass spectrometer for C12 H24 O N Si: calculated 226.1627, found 226.1624.

Example 5

Preparation of 7-Amino-1-t-butyldimethylsilyloxy-heptane (Compound X3, FIG. 14)

To a solution of lithium aluminium hydride (600 mg, Aldrich) in ether (50 mL) was added dropwise the product (3.8 g) from Example 4 in ether (50 mL). After 1–3 h, the mixture was poured into water and stirred for 30 min. The insoluble aluminum hydroxide was filtered through a celite pad, and the aqueous layer was extracted with ether three times. The ether extracts were washed with brine solution, dried and concentrated. The crude product was distilled at 0.25 Torr and 82° C. High resolution mass spectrum for C13 H31 O N Si: calculated 245.2175, found 245.2159.

Example 6
Preparation of (N-Monomethoxytrityl)-7-amino-1-t-butyldimethylsilyloxy-heptane (Compound X4, FIG. 14)

Monomethoxytrityl chloride (3.7 g, Aldrich) was added to a solution of the product (2.3 g) from Example 5 in dichloromethane (40 mL). After stirring at room temperature for 10 to 24 h, the solution was poured into a solution of saturated sodium bicarbonate. The aqueous layer was extracted with dichloromethane. The dichloromethane extracts were washed with brine solution and dried. The solvent was evaporated and the product was purified on silica gel chromatography. The purified compound X4 was analysed by high resolution mass spectrometer. C33 H47 O2 N Si: calculated 517.3376, found 517.3355.

Example 7
Synthesis of N-Monomethoxytrityl-7-aminoheptanol (Compound X5, FIG. 14)

A 1M Solution of tetrabutylammonium fluoride (25.8 mL) was slowly added to a solution of the compound X4 (4.3 g) in tetrahydrofuran (46 mL). After stirring at room temperature for 4 to 18 h, the solution was poured into 100 mL of water and stirred for another 30 min. The organic phase was extracted with brine solution and dried. The crude product was then purified on silica gel. The purified product was analysed by high resolution mass spectrometry. C27 H33 O2 N: calculated 403.2511, found 403.2514.

Example 8
Preparation of N-Monomethoxytrityl-7-aminoheptyl (2-cyanoethyl)-N,N-diethylphosphoramidite (Compound X6, FIG. 14)

To a solution of compound X5 (240 mg) in dioxane (10 mL) was added diisopropylethylamine (840 μL) and 2-cyanoethyl-N,N-diisopropylchlorophosphoramidite (270 μL). After stirring for 1 h, the reaction mixture was diluted with dichloromethane and washed with 1M solution of triethylammonium bicarbonate and finally with brine solution. After drying and concentrating, the residue was purified by silica gel chromatography. The product was analysed by high resolution mass spectrometry. C36 H50 N3 O3 P:calculated 603.3620, found 603.3620. The structure of the product was also comfirmed by NMR analysis.

Example 9
Preparation of Succinyl Ribosylribitol-PEG (FIG. 14)

To a solution of compound 16 (1.8 g) in dichoromethane (18 mL), N-hydroxybenzotriazole (295 mg) and dicyclohexylcarbodiimide (450 mg) were added. The reaction mixture was stirred at room temperature. After 2–8 h, dicyclohexylurea was removed by filtration. The filtrate, N-methylimidazole (522 μL) and diisopropylethylamine (600 μL) were added to polyethylene glycol monomethyl ether, PEG (Average M.wt.5000; 2.1 g, Fluka). The mixture was stirred overnight at room temperature under argon. The functionalized PEG was precipitated with cold ether and filtered. The loading capacity was determined spectrophotometrically according to the method of Gait et al. (ref. 36) and found to be about 200 μmol/g. Free residual hydroxyl groups were capped with a mixture of 20% acetic anhydride/pyridine in dichloromethane for 1 to 3 h at room temperature. The support was then precipitated with cold ether, filtered and washed with cold ether.

Example 10
Preparation of Synthetic PRP Using Soluble-polymeric Support (FIG. 13)

One gram of PEG-PRP-DMT (product of Example 9) was evaporated twice with pyridine and dissolved in acetonitrile under argon. The PRP oligosaccharide was elongated in a cycle of four steps, each step being preceded by the precipitation of the functionalized PEG with cold ether to remove by-products, followed by crystallization from dichloromethane/ether. The first step of synthesis involved removal of dimethoxytrityl group using 3% toluene sulfonic acid in chloroform/methanol acid, followed by coupling with the ribosylribitol phosphoramidite product from Example 3 in the presence of tetrazole (180 min). The coupling efficiency was determined to be 95%. Oxidation (step 3) was performed using 70% t-butyl hydroperoxide solution (120 min), and finally capping (step 4) using 20% acetic anhydride/pyridine in dichloromethane (60 min). Two cycles of synthesis were performed, followed by coupling the spacer phosphoramidite product from Example 8. The resin was then heated with aqueous concentrated ammonia tetrahydrofuran for 17 to 24 h at 50 to 100° C. The mixture was filtered to remove PEG, washed and the solvents were evaporated. Hydrogenolysis of the product in the presence of 10% Pd/charcoal in t-butyl alcohol/water/acetic acid (4:3:1) using a medium pressure hydrogenation apparatus at 40 psi provided a homogeneous product after filtration. The product was lyophilized, and then purified by a combination of gel filtration over a column of Sephadex G-25 in 0.01M triethylammonium bicarbonate pH 7, followed by ion exchange chromatography on Sephadex C-25 using water. Lyophilization of the appropriate fractions provided a solid product whose structure was analysed by NMR. A spectrum of ribosylribitol phosphate trimer was obtained and found to be similar to that reported by Hoogerhout et al. (J. Carbohydr. Chem. 7, 399, 1988).

Example 11
Modification of Synthetic $(PRP)_3$ With m-Maleimidobenzoyl-N-hydroxysuccinimide A solution of m-Maleimidobenzoyl-N-hydroxysuccinimide (20 mg; 63.6 μmol) in tetrahydrofuran (1 mL) was added to a solution of synthetic $(PRP)_3$ (5.2 mg; 4.3 μmol) in 0.1 M phosphate buffer solution (1 mL), pH 7.5. After stirring the solution for 30 min at room temperature under argon, the reaction mixture was extracted with ether (4×5 mL), and the resulting aqueous layer was applied to a Sephadex G-25 (Pharmacia) column (2×30 cm) equilibrated with 0.1 M triethylammonium acetate buffer, pH 7.2, and eluted with the same buffer. Elution was monitored spectrophotometrically at 254 nm. The first eluted peak was pooled and lypholized. The amount of maleimide groups incorporated into $(PRP)_3$ was determined using a modified Ellman's method (ref. 39), and found to be 90% incorporation.

Example 12
Peptide Synthesis

Peptides from OMP P1, P2 and P6 (Tables 1 to 3) were synthesized using an ABI 430A peptide synthesizer and optimized t-Boc chemistry as described by the manufacturer, then cleaved from the resin by hydrofluoric acid (HF). The peptides were purified by reverse-phase high performance liquid chromatography (RP-HPLC) on a Vydac C4 semi-preparative column (1×30 cm) using a 15 to 55% acetonitrile gradient in 0.1% trifluoryl acetic acid (TFA) developed over 40 minutes at a flow rate of 2 mL/min. All synthetic peptides (Tables 1–3) used in biochemical and immunological studies were >95% pure as judged by analytical HPLC. Amino acid composition analyses performed on a Waters Pico-Tag system were in good agreement with the theoretical compositions. The synthetic MAP (OMP2-8)$_8$ was manually prepared using t-Boc solid-phase peptide synthesis chemistry according to the method previously described by Tam et al. (ref. 40). Cysteine residues were added at both N- and C-terminal ends of the peptide for PRP-conjugation purposes. The MAP peptide was purified by RP-HPLC as previously described.

Example 13
Preparation of Fully Synthetic Peptide-(PRP)$_3$ Conjugates

One to two milligrams of individual synthetic peptides (OMP2-8)$_8$ and HIBP1-4 were dissolved in 0.5 mL of well-degassed water, and 0.8 mL of MBS-(PRP)$_3$ (1.6 mg) in well-degassed water was added. The resulting mixture was stirred at room temperature under argon overnight. The insoluble precipitate was removed by centrifugation, and the supernatant subjected to gel filtration chromatography on a column of G-50 Sephadex (2×30 cm) equilibrated in 0.1 M triethylammonium acetate buffer, pH 7.2, to remove excess MBS-(PRP)$_3$. The synthetic peptide(PRP)$_3$ conjugates were collected and analysed by reversed phase HPLC, Orcinol test and amino acid analysis. The molar ratio of peptide to PRP was about 1:1 and 1:5 for HIBP1-4 and MAP peptide conjugates, respectively. The synthetic peptide-PRP conjugates were then absorbed onto alum for immunogenicity studies.

Example 14
Preparation of Native PRP-BSA Conjugate

A 0.5 mL of periodate-oxidized PRP (25 mg in 1 mL of 0.1 M sodium phosphate buffer, pH 6.0), prepared from native PRP treated with aqueous periodic acid (4), was added to bovine serum albumin (BSA) (1.32 mg; 0.02 $\mu$mol) in 0.5 mL of 0.2 M sodium phosphate buffer, pH 8.0, followed by the addition of sodium cyanoborohydride (14 $\mu$g; 0.22 $\mu$mol; 10 eqv. to BSA). After incubation at 37° C. for 5 days, the reaction mixture was dialysed against 0.1 M phosphate buffer (4×1 L), pH 7.5, and the resulting solution was applied onto an analytical Superose 12 column (15×300 mm, Pharmacia) equilibrated with 0.2 M sodium phosphate buffer, pH 7.2, and eluted with the same buffer. Fractions were monitored for absorbance at 230 nm. The major peak was pooled and concentrated in a Centriprep 30 (Pierce) to 2.2 ml. The amount of protein was determined using the Bio Rad protein assay, and was found to be 300 $\mu$g/ml. Derivatization with PRP was confirmed by the Orcinol test.

Example 15
Production of Anti-peptide and Anti-OMP Antisera

Rabbits, mice (Balb/C) and guinea pigs were immunized itramuscularly (im) with native P1 or P2 or P6 or individual peptides (5 to 100 $\mu$g) emulsified in complete Freund's adjuvant, and followed by two booster doses (half amount of the same immunogen in incomplete Freund's adjuvant) at 2 week intervals. Antisera were collected and stored as described above.

Exampel 16
Production of Anti-PRP Antisera

Rabbits were immunized intramuscularly with individual PRP-carrier conjugates (5–50 $\mu$g PRP equivalent) mixed with 3 mg AlPO$_4$ per mL, followed by two booster doses (half amount of the same immunogen) at 2 week intervals. Antisera were collected every 2 weeks after the first injection, heat-inactivated at 56° C. for 30 min and stored at −20° C.

Example 17
P1-, P2-, P6- and Peptide-specific ELISAs

Microtiter plate wells (Nunc-Immunoplate, Nunc, Denmark) were coated with 200 ng of purified OMPs or 500 ng of individual peptides in 50 $\mu$L of coating buffer (15 mM Na$_2$CO$_3$, 35 mM NaHCO$_3$, pH 9.6) for 16 hr at room temperature. The plates were then blocked with 0.1% (w/v) BSA in phosphate buffer saline (PBS) for 30 min at room temperature. Serially diluted antisera were added to the wells and incubated for 1 hr at room temperature. After removal of the antisera, the plates were washed five times with PBS containing 0.1% (w/v) Tween-20 and 0.1% (w/v) BSA. F(ab')$_2$ from goat anti-rabbit, guinea pig, mouse, or human IgG antibodies conjugated to horseradish peroxidase (Jackson ImmunoResearch Labs Inc., Pennsylvania) were diluted (1/8,000) with washing buffer, and added onto the microtiter plates. After 1 hr incubation at room temperature, the plates were washed five times with the washing buffer. The plates were then developed using tetramethylbenzidine (TMB) in H$_2$O$_2$ (ADI, Toronto) as substrate. The reaction was stopped with 1N H$_2$SO$_4$ and the optical density was measured at 450 nm using a Titretek Multiskan II (Flow Labs., Virginia). Two irrelevant pertussis toxin peptides NAD-S1 (19 residues and S3(123–154) (32 residues) were included as negative controls in the peptide-specific ELISAs. Assays were performed in triplicates, and the reactive titre of an antiserum was defined as the dilution consistently a showing two-fold increase in O.D. value over that obtained with the pre-immune serum.

Example 18
Anti-PRP Antibody Measurement

Microtiter plate wells (Nunc-Immunoplate, Nunc, Denmark) were coated with 200 ng of purified PRP-BSA in 200 $\mu$L of coating buffer (15 mM Na$_2$CO$_3$, 35 mM NaHCO$_3$, pH 9.6) for 16 hr at room temperature. The plates were then blocked with 0.1% (w/v) BSA in phosphate buffer saline (PBS) for 30 min at room temperature. Serially diluted antisera raised against PRP-carrier conjugates were added to the wells and incubated for 1 hr at room temperature. After removal of the antisera, the plates were washed five times with PBS containing 0.1% (w/v) Tween-20 and 0.1% (w/v) BSA. F(ab')$_2$ from goat anti-rabbit IgG antibodies conjugated to horseradish peroxidase (Jackson ImmunoResearch Labs Inc., Pennsylvania) were diluted (1/8,000) with washing buffer, and added onto the microtiter plates. After 1 hr incubation at room temperature, the plates were washed five times with the washing buffer. The plates were then developed using the substrate tetramethylbenzidine (TMB) in H$_2$O$_2$ (ADI, Toronto), the reaction was stopped with 1N H$_2$SO$_4$ and the optical density was measured at 450 nm using a Titretek Multiskan II (Flow Labs., Virginia). A standard anti-PRP antiserum was included as positive control. Assays were performed in triplicates, and the reactive titre of an antiserum was defined as the dilution consistently showing a two-fold increase in O.D. value over that obtained with the pre-immune sera.

Example 19
Proliferation Assay for Synthetic T-cell Epitopes

T-cell epitope mapping was performed by priming Balb/c, C57B1/6 and A/J mice with 5 $\mu$g of individual OMPs (P1, or P2 or P6). Three weeks later, the spleens were removed and the splenocytes cultured in RPMI 1640 (Flow Lab) supplemented with 10% heat-inactivated fetal calf serum (Gibco), 2 mM L-glutamine (Flow Lab), 100 U/mL penicillin (Flow Lab), 100 $\mu$g/mL streptomycin (Flow Lab), 10 unit/mL rIL-2 and 50 $\mu$M 2-mercaptoethanol (sigma) for 5 to 7 days. Proliferative responses of the primed splenocytes to the panel of OMP peptides were determined in a standard in vitro assay (ref. 41). Briefly, $10^6$ splenocytes were co-cultured in a 96-well microtiter plate with $5\times10^5$ irradiated (1700 Rad) fresh syngeneic spleen cells used as source of antigen presenting cells (APC) in the presence of increasing molar concentrations (0.03 to 3 µM of peptide dissolved in the culture medium without IL-2). Cultures were kept for 40 hr in a humidified 5% $CO_2$/air incubator maintained at 37° C. During the final 16 hr of culture, 0.5 µCi of [$^3$H]-Tdr (5 Ci/mmol, NEN) was added to each wells. The cells were then harvested onto glass fibre filters, and the incorporation of $^3$H-thymidine into cellular DNA was measured in a scintillation β-counter (Beckman). Results are expressed as the mean of triplicate determinations performed for each peptide concentration. The standard 5205 PCr/CA93/00041 deviation was always <15%. Proliferative responses were considered as positive when $^3$H-thymidine incorporation was three-fold above that obtained with either irrelevant peptides or the culture medium.

Example 20

Immunoblot Analysis

The immunospecificity of antisera raised against peptides and PRP-carrier conjugates were determined by immunoblot analysis as previously described (ref. 42).

SUMMARY OF DISCLOSURE

In summary of this disclosure, the present invention provides immunogenic synthetic peptides which are useful alone or in PRP-conjugates in vaccines gainst Hi infection. Modifications are possible within the scope of the invention.

REFERENCES

1. Tarr, P. I., and G. Peter. 1978. J. Pediatr. 92:884–888.
2. Turk, D. C. 1984. J. Med. Microbiol. 18:1–16.
3. Ward, J., and S. Cochi. 1988. *In Vaccines*, pp 300. Edited by S. A. Plotkin and E. A. Mortimer. Philadelphia: W. B. Saunders Company.
4. Gordon, L. K. 1984. *In Modern Approaches to Vaccines*. pp. 393–396. Edited by R. M. Chanock and R. A. Lerner. Cold Spring Harbor, N.Y. Cold Spring Harbor Press.
5. Kayhty, H., H. Peltola, J. Eskola, P. R. Ronnberg, E. Kela, V. Varanko, and P. H. Makela. 1989. Pediatrics 84:995–999.
6. Granoff, D. M., and R. S. Munson, Jr. 1986. J. Infect. Dis. 153:448–461.
7. Gonzales, F. R., S. Leachman, M. V. Nargard, J. D. Radolf, G. H. McCracken, Jr., C. Evans, and E. J. Hansen. 1987. Infect. Immun. 55:2993–3000.
8. Munson, R., Jr., S. Grass, M. Einhorn, C. Bailey, and C. Newell. 1989. Infect. Immun. 57:3300–3305.
9. Hansen, E. J., S. M. Robertson, P. A. Gulig, C. F. Trisch, and E. J. Haanes. 1982. Lancet i:366–368.
10. Munson Jr., R. S., S. Grass, M. Finhorn, C. Bailey and C. Newell. (1989) Infect. Immun. 57:3300.
11. Munson, R., Jr., C. Bailey, and S. Grass. (1989). Molec. Micro. 3:1797–1803.
12. Nelson et al. 1991. Infect. Immun. 59:2658–2663.
13. Loeb, M. R. 1987. Infect. Immun. 55:2612–2618.
14. Pelton, S. I., G. Bolduc, S. Gulati, Y. Liu, and P. A. Rice. 1990. 30th ICAAC, Atlanta, Ga. Abstr. #610.
15. Murphy, T. F. and L. C. Bartos. (1988) Infect. Immun. 56:1084–1089.
16. Martin et al. (1991) Infect. Immun. 59:1457–1460.
17. Van Alphen et al. (1991) Infect. Immun. 59:247–252.
18. Proulx, C., R. S. Munson, Jr., S. Grass, J. Hamel, D. Martin, and B. R. Brodeur. 1991. Infect. Immun. 59:963–970.
19. Harari, I., A. Donohue-Rolfe, G. Keusch, and R. Arnon. (1988). Infect. Immun. 56:1618.
20. Chong, P., M. Sydor, G. Zobrist, H. Boux, and M. Klein. (1991). Mole. Immunol. 28:239–245.
21. Jacob, C. O., M. Sela, and R. Arnon. (1983). Proc. Natl. Acad. Sci. USA 80:7611.
22. Steward, M. W. and C. R. Howard. (1987). Immunol. Today 8:57–58.
23. Milich, D. R., D. L. Peterson, G. G. Leroux- Roels., R. A. Lerner and F. V. Chisari. (1985). J. Immunol. 134:4203–4211.
24. Milich, D. R., A. McLachlan, G. B. Thornton and J. L. Hughes. (1987). Nature. 329:547–549.
25. Milich, D. R., J. L. Hughes, A . McLachlan, G. B. Thornton and A. Moriarty. (1988). Proc. Natl. Acad. Sci. USA. 85:1610–1614.
26. Milich, D. R. (1988). Adv. Immunol. 45:195–281.
27. Beuvery, E. C. et al. Eur. Patent Appl. EP 0276516
28. Just, G. E. and Upeslacis J. Eur. Patent Appl. EP 0320942
29. Chou, P. Y., and G. D. Fasman. (1978). Annu. Rev. Biochem. 47:251–276.
30. Hopp, T. P. (1986). J. Immunol. Methods. 88:1–18.
31. Parker, J. M. R., D. Guo, and R. S. Hodges. (1986). Biochemistry 25:5425–5432.
32. Van Regenmortel, M. H. V., S. Muller, V. F. Quesniaux, D. Altchuh, and J. P. Briand. (1988). In Vaccines: New Concepts and Developments, pp. 113–122. Edited by H. Kohler and P. T. LaVerde. London: Longman.
33. Leonard, N. J. and K. L. Carraway (1966). J. Heterocyclic Chemistry 3:485.
34. Hanessian, S. and J. Banoub (1975). J. Carbohydrate Res. 44: C147.
35. Chan, L. and G. Just (1988). Tetrahedron Lett. 4049.
36. Gait et al. (1982). Nucleic Acid Res. 10:6243.
37. Kandil, A and K. Slessor (1983) Can. J. Chem. 61:1166.
38. Hoogerhout et al. (1988) J. carbohydr. Chem. 7:399.
39. Riddles, P., R. L. Blakeley and B. Zerner (1983) Methods Enmol. 91:49.
40. Tam, J. P. (1988) Proc. Natl. Acad. Sci. U.S.A., 85:5409.
41. Sia, D. Y. and J. L. Chou. (1987). Scand. J. Immunol. 26:683–690.
42. Towbin, H., T. Staehelin, and J. Gordon. (1979) Proc. Natl. Acad. Sc. USA 76:4350–4354.

TABLE 1

OVERLAPPING PEPTIDES of Hib OMP P1

| PEPTIDES | SEQUENCES | SEQ ID NO: |
|---|---|---|
| HIBP1-1 (1–29) | AAFQLAEVSTSGLGRAYAGEAAIADNASV(C) | – SEQ ID NO: 1 |
| HIBP1-2 (60–88) | GDVTSYAQIITNQIGMKAIKDGSASQRNV(C) | – SEQ ID NO: 2 |
| HIBP1-3 (103–137) | (C)VNDKFALGAGMNVNFGLKSEYDDSYDAGVFGGKTD | – SEQ ID NO: 3 |
| HIBP1-4 (165–193) | YAKAQVERNAGLIADSVKDNQITSALSTQ(C) | – SEQ ID NO: 4 |
| HIBP1-5 (189–218) | ALSTQQEFRDLKKYLPSKDKSVVSLQDRA(C) | – SEQ ID NO: 5 |
| HIBP1-6 (226–253) | (C)AGVMYQFNEANRIGLAYHSKVDIDFADR | – SEQ ID NO: 6 |
| HIBP1-7 (248–283) | IDFADRTATSLEANVIKEGKKGNLTFTLPDYLELSG(C) | – SEQ ID NO: 7 |
| HIBP1-8 (279–312) | LELSGFHQLTDKLAVHYSYKYTHWSRLTKLHASF(C) | – SEQ ID NO: 8 |
| HIBP1-9 (307–331) | KLHASFEDGKKAFDKELQYSNNSRV(C) | – SEQ ID NO: 9 |
| HIBP1-10 (339–370) | LYEKLTLRAGIAYDQAASRHHRSAAIPDTDRT(C) | – SEQ ID NO: 10 |
| HIBP1-11 (384–412) | LSVDLGYAYLKGKKVHFKEVKTIGDKRTL(C) | – SEQ ID NO: 11 |
| HIBP1-12 (39–64) | LFKTAQFSTGGVYIDSRINMNGDVTS(C) | – SEQ ID NO: 12 |
| HIBP1-13 (400–437)1H | (C)FKEVKTIGDKRTLTLNTTANYTSQAHANLYGLNLNYSF | – SEQ ID NO: 13 |
| HIBP1-14 (400–37)6U | (C)FKEAQQAAGGFITTTANYTSQAHANLYGLNLNYSF <br> \*\*\*\*\*\*\*\*\*\* | – SEQ ID NO: 14 |
| HIBP1-15 (179–218) | DSVKONDITSALSTQQEFRDLKKYLPSKDKSVVSLQDRA | – SEQ ID NO: 15 |

*The asterisks points to residues which are different from those found in the P1 protein of the *H. influenzae* strain 1H (ref. 10)

TABLE 2

Hib OMP P2 OVERLAPPING EPITOPES

| PEPTIDES | | SEQUENCES | SEQ ID NO: |
|---|---|---|---|
| PORIN 1 | 1–14 | AVVYNNEGTNVELG(C) | – SEQ ID NO: 16 |
| HIBP2-26 | 8–19 | GTNVELGGRLSI | – SEQ ID NO: 17 |
| HIBP2-25 | 17–32 | LSIIAEQSNSTVDNQK | – SEQ ID NO: 18 |
| OMP2-1 | 28–55 | VDNQKQQHGALRNQGSRFHIKATHNFGD(C) | – SEQ ID NO: 19 |
| OMP2-2 | 53–81 | FGDGFYAQGYLETRFVTKASENGSDNFGD(C) | – SEQ ID NO: 20 |
| OMP2-3 | 79–106 | (C)FGDITSKYAYVTLGNKAFGEVKLGRAKT | – SEQ ID NO: 21 |
| OMP2-4 | 101–129 | GRAKTIADGITSAEDKEYGVLNNSDYIP(C) | – SEQ ID NO: 22 |
| OMP2-5 | 125–150 | SDYIPTSGNTVGYTFKGIDGLVLGAN(C) | – SEQ ID NO: 23 |
| OMP2-6 | 148–174 | (C)GANYLLAQKREGAKGENKRPNDKAGEV | – SEQ ID NO: 24 |
| OMP2-7 | 171–196 | AGEVRIGEINNGIQVGAKYDANDIVA(C) | – SEQ ID NO: 25 |

TABLE 2-continued

Hib OMP P2 OVERLAPPING EPITOPES

| PEPTIDES | | SEQUENCES | SEQ ID NO: |
|---|---|---|---|
| OMP2-9 | 219–244 | (C)GVLATLGYRFSDLGLLVSLDSGYAKT | - SEQ ID NO: 27 |
| OMP2-10 | 241–265 | YAKTKNYKIKHEKRYFVSPGFQYEL(C) | - SEQ ID NO: 28 |
| OMP2-11 | 263–289 | (C)YELMEDTNVYGNFKYERTSVDQGEKTR | - SEQ ID NO: 29 |
| OMP2-12 | 285–306 | GEKTREQAVLFGVDHKLHKQLL(C) | - SEQ ID NO: 30 |
| OMP2-13 | 302–319 | KQLLTYIEGAYARTRTT(C) | - SEQ ID NO: 31 |
| CHIBP | 314–341 | (C)ARTRTTETGKGVKTEKEKSVGVGLRVYF | - SEQ ID NO: 32 |
| OMP2-6U | 148–174 | (C)GANYLLAQKREGAKMANKLPNNKAGEV  ** * * | - SEQ ID NO: 33 |
| OMP2-6L | 148–174 | (C)GANYLLAQKREGAKGENKQPNDKAGEV  * | - SEQ ID NO: 34 |

*The asterisks point to residues which are different from those found in the P2 protein of the H. influenzae strain 1H (ref. 11).

TABLE 3

OVERLAPPING PEPTIDES OF Hib OMP P6

| PEPTIDES | SEQUENCES | SEQ ID NO: |
|---|---|---|
| P6-1 (1–22) | CSSSNNDAAGNGAAQTFGGYSV(C) | - SEQ ID NO: 35 |
| P6-2 (19–41) | (C)GYSVADLQQRYNTVYFGFDKYDI | - SEQ ID NO: 36 |
| P6-3 (35–58) | GFDKYDITGEYVQILDAHAAYLNA(C) | - SEQ ID NO: 37 |
| P6-4 (54–77) | (C)AYLNATPAAKVLVEGNTDERGTPE | - SEQ ID NO: 38 |
| P6-5 (73–96) | RGTPEYNIALGQRRADAVKGYLAG(C) | - SEQ ID NO: 39 |
| P6-6 (90–114) | VKGYLAGYLAGKGVDAGKLGTVSYG(C) | - SEQ ID NO: 40 |
| P6-7 (109–134) | (C)GTVSYGEEKPAVLGHDEAAYSKNRRAVLAY | - SEQ ID NO: 41 |

TABLE 4

Reactivity of antisera raised against OMP P1 determined by P1-specific ELISAs.

| SPECIES | IMMUNOGENS | REACTIVE TITER[1] |
|---|---|---|
| Human#1 | H. influenzae type b[2] | 3,200 |
| Human#2 | H. influenzae type b | 6,400 |
| Human#3 | H. influenzae type b | 3,200 |
| Guinea pig #390 | Native P1 | 204,800 |
| Guinea pig #392 | Native P1 | 204,800 |
| Mouse (A/J)[3] | Native P1 | 204,800 |
| Mouse (Balb/C) | Native P1 | 102,400 |
| Mouse (BL6) | Native P1 | 102,400 |
| Mouse (C3H) | Native P1 | 102,400 |
| Mouse (SWR/J) | Native P1 | 102,400 |
| Rabbit #247* | Native P1 | 12,800 |
| Rabbit #249 | Native P1 | 6,400 |
| Rabbit #250 | Native P1 | 6,400 |

[1]Pre-immunization titers were subtracted from post-immunization titers.
[2]Antisera were obtained from convalescent patients.
[3]Two mice per group were used in immunogenicity studies.
*Anti-P1 antisera were shown to be protective in the infant rat model of bacteremia.

TABLE 5

Reactivity of antisera raised against OMP P2 determined by P2-Specific ELISA

| SPECIES | IMMUNOGENS | REACTIVE TITER[1] |
|---|---|---|
| Human#1 | H. influenzae type b[2] | 25,600 |
| Human#2 | H. influenzae type b | 6,400 |
| Human#3 | H. influenzae type b | 1,600 |
| Guinea pig #52 | Native P2 | 409,000 |
| Guinea pig #RF3430 | Native P2 | 1,638,400 |
| Guinea pig #RF3438* | Native P2 | 6,553,600 |
| Mouse (A/J)[3] | Native P2 | 1,600 |
| Mouse (SJL/J) | Native P2 | 25,600 |
| Mouse (Balb/C) | Native P2 | 12,800 |
| Mouse (BL6) | Native P2 | 25,600 |
| Mouse (C3H) | Native P2 | 12,800 |
| Mouse (SWR/J) | Native P2 | 6,400 |
| Rabbit #RF3428* | Native P2 | 819,200 |
| Rabbit #493* | Native P2 | 6,533,600 |

[1]Pre-immunization titers were subtracted from post-immunization titers.
[2]Antisera were obtained from convalescent patients.
[3]Two mice per group were used in immunogenicity studies.
*Anti-P2 antisera were shown to be protective in the infant rat model.

TABLE 6

Reactivity of antisera raised against OMP P6 determined by P6-specific ELISA

| SPECIES | IMMUNOGENS | REACTIVE TITER[1] |
|---|---|---|
| Rat RF6843 | Native P6 | 128,000 |
| Rat RF6880H | Native P6 | 3,200 |
| Guinea pig #792 | Native P6 | 564,000 |
| Guinea pig #793 | Native P6 | 1,638,400 |
| Guinea pig #794 | Native P6 | 1,253,600 |
| Rabbit #274 | Native P6 | 819,200 |
| Rabbit #276* | Native P6 | 2,733,600 |

[1]Pre-immunization titers were subtracted from post-immunization titers.
*Anti-P6 antisera were shown to be protective in the infant rat model.

TABLE 7

Proliferative responses of T-cell lines generated from Balb/c mice immunized with P6 to P6 synthetic peptides

| Antigens | Cell Proliferation Index[1] |
|---|---|
| rP6 | 10.5 |
| Hib P1 | 1.2 |
| P6-1 | 1.2 |
| P6-2 | 20.5 |
| P6-3 | 10.3 |
| P6-4 | 1.3 |
| P6-5 | 5.8 |
| P6-6 | 0.9 |
| P6-7 | 22.4 |
| P24E | 1.4 |
| MEDIUM | 1.0 |

[1]Boldfaced numbers correspond to significant T-cell proliferative responses indicate that immunodominant T-cell epitopes are located within the immunostimulatory peptides.

TABLE 8

PROPERTIES OF RABBIT ANTISERA RAISED AGAINST P1 PEPTIDES

| | ANTISERA REACTIVITY AGAINST | | | |
|---|---|---|---|---|
| | SPECIFIC-ELISAs | | WESTERN BLOT AGAINST P1 | |
| IMMUNOGEN | PEPTIDE | P1 | Hib | Non-typeable |
| HIBP1-1 | YES | NO | YES | YES |
| HIBP1-1-KLH | YES | NO | YES | YES |
| HIBP1-2 | YES | NO | YES | NO |
| HIBP1-2-KLH | YES | NO | YES | NO |
| HIBP1-3 | YES | NO | YES | YES |
| HIBP1-3-KLH | YES | NO | YES | YES |
| HIBP1-4 | YES | YES | YES | YES* |
| HIBP1-4-KLH | YES | NO | YES | NO |
| HIBP1-5 | YES | YES | YES | YES |
| HIBP1-5-KLH | YES | YES | YES | YES |
| HIBP1-6 | YES | NO | YES | YES |
| HIBP1-6-KLH | YES | NO | NO | NO |
| HIBP1-7 | YES | NO | YES | YES |
| HIBP1-7-KLH | YES | YES | YES | YES |
| HIBP1-8 | NO | NO | NO | NO |
| HIBP1-8-KLH | NO | NO | NO | NO |
| HIBP1-9 | YES | YES | YES | YES |
| HIBP1-9-KLH | YES | NO | YES | YES |
| HIBP1-10 | YES | NO | YES | NO |
| HIBP1-10-KLH | YES | YES | YES | YES* |
| HIBP1-11 | YES | YES | YES | YES* |
| HIBP1-11-KLH | YES | YES | YES | NO |
| HIBP1-12 | YES | NO | YES | YES |
| HIBP1-12-KLH | YES | NO | YES | YES |
| HIBP1-13 | YES | NO | YES | YES |
| HIBP1-13-KLH | YES | NO | YES | YES |

*Rabbit antisera recognized one or two out of five non-typeable Hi isolates tested.

TABLE 9

Immunological properties of rabbit antisera raised against P2 peptides and peptide-KLH conjugates.

| IMMUNOGENS | RECIPROCAL REACTIVE TITRE AS DETERMINED BY ELISAS[1] | | RECOGNITION OF P2 IN IMMUNOBLOTS | |
| --- | --- | --- | --- | --- |
| | NATIVE P2 | SPECIFIC PEPTIDES | Hib | NON-TYPEABLE |
| PORIN 1-KLH | 3,200 | 104,800 | YES | YES |
| PORIN 1 | <200 | <200 | NO | NO |
| HIBP2-25-KLH | <200 | 25,600 | YES | NO |
| HIBP2-25 | <200 | 102,400 | YES | NO |
| HIBP2-26-KLH | <200 | <200 | NO | NO |
| HIBP2-26 | <200 | <200 | NO | NO |
| OMP2-2-KLH | <200 | 6,400 | YES | NO |
| OMP2-1 | <200 | 3,200 | YES | NO |
| OMP2-2-KLH | <200 | 409,600 | YES | NO |
| OMP2-2 | <200 | 204,800 | YES | NO |
| OMP2-3-KLH | <200 | 3,200 | YES | NO |
| OMP2-3 | <200 | 102,400 | YES | NO |
| OMP2-4-KLH | <200 | 6,400 | YES | NO |
| OMP2-4 | 12,800 | 102,400 | YES | NO |
| OMP2-5-KLH | 25,600 | 204,800 | YES | YES |
| OMP2-5 | <200 | 102,400 | YES | YES |
| OMP2-6-KLH | <200 | 6,400 | YES | NO |
| OMP2-6 | <200 | 204,800 | YES | NO |
| OMP2-7-KLH | 3,200 | 51,200 | YES | NO |
| OMP2-7 | <200 | 102,400 | YES | NO |
| OMP2-8-KLH | 6,400 | 51,200 | YES | YES |
| OMP2-8 | 51,200 | 3,276,800 | YES | YES |
| OMP2-9-KLH | <200 | 6,400 | YES | NO |
| OMP2-9 | <200 | 409,600 | YES | NO |
| OMP2-10-KLH | 3,200 | 51,200 | YES | YES |
| OMP2-10 | 12,800 | 409,600 | YES | YES |
| OMP2-11-KLH | <200 | 800 | YES | YES |
| OMP2-11 | 6,400 | 102,400 | YES | YES |
| OMP2-12-KLH | 51,200 | 3,276,800 | YES | YES |
| OMP2-12 | S1,200 | 32,000 | YES | YES |
| OMP2-13-KLH | <200 | <200 | NO | NO |
| OMP2-13 | 51,200 | 1,638,400 | YES | YES |
| CHIBP2-KLH | 12,800 | 204,800 | YES | NO |
| CHIBP2 | <200 | 1,600 | YES | NO |
| OMP2-6U-KLH | 204,800 | 3,276,800 | YES | YES |

The data shown are those obtained with rabbit antisera having The highest antibody titer.

TABLE 10

Immunological properties of rabbit antisera raised against P6 peptides.

| IMMUNOGENS | REACTIVE TITER AS DETERMINED BY ELISAS[1] | | RECOGNITION OF P6 IN IMMUNOBLOTS | |
| --- | --- | --- | --- | --- |
| | NATIVE P6 | SPECIFIC PEPTIDES | Hib | NON-TYPEABLE |
| P6-1 | 200 | 6,400 | YES | YES |
| P6-2 | 1,600 | 25,600 | YES | YES |
| P6-3 | 1,600 | 1,600 | YES | YES |
| P6-4 | <50 | 800 | YES | YES |
| P6-5 | 800 | 3,200 | YES | YES |
| P6-6 | 400 | 3,200 | YES | YES |
| P6-7 | 800 | 12,800 | YES | YES |

[1]The data shown are those obtained with rabbit antisera having the highest antibody titer.

TABLE 11

IMMUNOLOGICAL PROPERTIES OF P1-P2 HYBRID SYNTHETIC PEPTIDES

| IMMUNOGENS | PEPTIDE SEQUENCE | RABBIT ANTI-PEPTIDE AGAINST | |
|---|---|---|---|
| | | P1 | P2 |
| P1-CP2 | VKTIGDKRTLTLNTCARTRTTETGKGVKTEKEKSVGVGLRVYF | | |
| | <---C-P1-----><--------CHIBP2--------------> | | |
| IN CFA | | 1/2800(2/2) | 1/6400(2/2) |
| IN ALUM | SEQ ID NO: 42 | <1/200(2/2) | 1/1600(1/2) |
| 1P13-2P2 | VKTIGDKNTLTLNTFGDGFYAQGYLETRFVTKASENGSNFGDC | | |
| | <---C-P1-----><--------OMP2-2-------------> | | |
| IN CFA | | 1/12800(2/2) | <1/200(2/2) |
| IN ALUM | SEQ ID NO: 43 | 1/12800(1/2) | <1/200(2/2) |
| 1P13-2P6 | VKTIGDKNTLTLNTCGANYKKAQKREGAKGENKRPNDKAGEV | | |
| | <---C-P1-----><--------OMP2-6------------> | | |
| IN CFA | | 1/6400(2/2) | 1/12800(2/2) |
| IN ALUM | SEQ ID NO: 44 | <1/200(2/2) | <1/200(2/2) |
| 1P13-2P8 | VKTIGDKRTLTLNTDIVAKIAYGRTNYKYNESDEHKQQLNGC | | |
| | <---C-P1-----><--------OMP2-8------------> | | |
| IN CFA | | 1/6400(1/2) | 1/12800(2/2) |
| IN ALUM | SEQ ID NO: 45 | 1/3200(1/2) | 1/1600(1/2) |
| 1P13-2P10 | VKTIGDKRTLTLNTYAKTKNYKIKHEKRYFVSPGFQYELC | | |
| | <---C-P1-----><--------OMP2-10---------> | | |
| IN CFA | | <1/200(2/2) | 1/1600(1/2) |
| IN ALUM | SEQ ID NO: 46 | <1/200(2/2) | <1/200(2/2) |
| 2P2-1P13 | GYLETRFVTKASENGSDFKEVKTIGDKRTLTLNTTANYTSQAHANLYGLNLNYSF | | |
| | <-------2P2-----><-------HIBP1-13---------------------> | | |
| IN CFA | | 1/3200(1/2) | <1/200(2/2) |
| IN ALUM | SEQ ID NO: 47 | <1/200(2/2) | <1/200(2/2) |
| 2P6-1P13 | AKGENKRPNDKAGEVFKEVKTIGDKRTLTLNTTANYTSQAHANLYGLNLNYSF | | |
| | <-------2P6---><-------HIBP1-13---------------------> | | |
| IN CFA | | 1/12800(1/2) | 1/12800(1/2) |
| IN ALUM | SEQ ID NO: 48 | 1/1600(1/2) | 1/3200(2/2) |
| CP2-1P13 | ARTRTTETGKGVKTEKFKEVKTIGDKRTLTLNTTANYTSQAHANLYGLNLNYSF | | |
| | <-------CP2----><-------HIBP1-13---------------------> | | |
| IN CFA | | 1/12800(1/2) | <1/200(2/2) |
| IN ALUM | SEQ ID NO: 49 | 1/6400(1/2) | <1/200(2/2) |

TABLE 12

Rabbit Immune Response to Synthetic (PRP)$_3$-Peptide conjugates[1]

| | | Anti-PRP IgG ELISA | | |
|---|---|---|---|---|
| | | Reactive Titres | | |
| Immunogens | | Pre | 2nd Post | 3rd Post |
| HIBP1-4 | RB946 | <50 | <50 | 1600 |
| | RB947 | <50 | <50 | 200 |
| CHIBP1-4 | RB5-32 | <50 | <50 | <50 |
| | RB5-33 | <50 | <50 | <50 |
| COMP2-8 | RB2-26 | <50 | 800 | 800 |
| | RB2-27 | <50 | <50 | <50 |
| | RB950 | <50 | 400 | 3200 |
| MAP(COMP2-8) | RB951 | <50 | 800 | 3200 |
| | RB3-28 | <50 | 400 | 400 |
| P24EC | RB3-29 | <50 | <50 | <50 |

[1]The immunization protocols and the anti-PRP IgG ELISA were performed as described in Examples 16 and 18.

What we claim is:

1. A synthetic peptide having an amino acid sequence which includes at least one antigenic determinant of at least one outer membrane protein (OMP) of *Haemophilus influenzae*, wherein said OMP is selected from the group consisting of (a) the P1 protein of *Haemophilus influenzae* type b and said amino acid sequence is at least one selected from the amino acid sequences 39 to 64 (SEQ ID NO: 12) and 179 to 218 (SEQ ID NO: 15) as set forth in Table 1, (b) the P2 protein of *Haemophilus influenzae* type b and said amino acid sequence is at least one selected from any of the amino acid sequences 1 to 14 (SEQ ID NO: 16), 53 to 81 (SEQ ID NO: 20), 125 to 150 (SEQ ID NO: 23), 148 to 174 (SEQ ID NO: 24), 193 to 219 (SEQ ID NO: 26), 219 to 244 (SEQ ID NO: 27), 241 to 265 (SEQ ID NO: 28), 263 to 289 (SEQ ID NO: 29), 285 to 306 SEQ ID NO: 30), 302 to 319 (SEQ ID NO:31), and 314 to 341 (SEQ ID NO: 32) as set forth in Table 2, and (c) the P6 protein of *Haemophilus influenzae* type b and said amino acid sequence is at least one selected from any of the amino acid sequences set forth in Table 3.

2. The synthetic peptide of claim 1 wherein said OMP is the P2 protein of *Haemophilus influenzae* type b and said amino acid sequence is at least one selected from any of the amino acid sequences 53 to 81 (SEQ ID NO: 20), 148 to 174 (SEQ ID NO: 24), 241 to 265 (SEQ ID NO: 28) and 314 to 341 (SEQ ID NO: 32) set forth in Table 2.

3. The synthetic peptide of claim 1 wherein said OMP is the P6 protein of *Haemophilus influenzae* type b and said amino acid sequence is at least one selected from any of the amino acid sequences 73 to 96 (SEQ ID NO: 39), 90 to 114 (SEQ ID NO: 40) and 109 to 134 (SEQ ID NO: 41) set forth in Table 3.

4. The synthetic peptide of claim 1 wherein said OMP is the P2 protein of *Haemophilus influenzae* type b and said amino acid sequence is selected from any one of the amino acid sequences 125 to 150 (SEQ ID NO: 23), 193 to 219 (SEQ ID NO: 26), 219 to 244 (SEQ ID NO: 27) and 241 to 265 (SEQ ID NO: 28) as set forth in Table 2.

5. The synthetic peptide of claim 1 wherein said OMP is the P6 protein of *Haemophilus influenzae* type b and said amino acid sequence is at least one selected from any of the amino acid sequences 19 to 41 (SEQ ID NO: 36), 35 to 58 (SEQ ID NO: 37), 73 to 96 (SEQ ID NO: 39) and 109 to 134 (SEQ ID NO: 41) as set forth in Table 3.

* * * * *